(12) United States Patent
Bouma et al.

(10) Patent No.: US 12,122,828 B2
(45) Date of Patent: Oct. 22, 2024

(54) IL-7 BINDING PROTEINS AND THEIR USE IN MEDICAL THERAPY

(71) Applicant: GlaxoSmithKline Intellectual Property Development Limited, Stevenage (GB)

(72) Inventors: Gerben Bouma, Stevenage (GB); Edward Thomas Coulstock, Stevenage (GB); David Dixon, Stevenage (GB); Stephanie Hopley, Stevenage (GB); Alan Peter Lewis, Stevenage (GB); Jessica Lynn Neisen, Stevenage (GB)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 0 days.

(21) Appl. No.: 18/460,944

(22) Filed: Sep. 5, 2023

(65) Prior Publication Data
US 2024/0025988 A1    Jan. 25, 2024

Related U.S. Application Data

(63) Continuation of application No. 17/538,431, filed on Nov. 30, 2021, now Pat. No. 11,802,150.

(60) Provisional application No. 63/120,564, filed on Dec. 2, 2020.

(51) Int. Cl.
C07K 16/24    (2006.01)
A61K 39/00    (2006.01)

(52) U.S. Cl.
CPC ...... C07K 16/244 (2013.01); *A61K 2039/505* (2013.01); *C07K 2317/92* (2013.01); *C07K 2317/94* (2013.01)

(58) Field of Classification Search
CPC .......... A61K 2039/505; C07K 2317/76; A61P 37/00
See application file for complete search history.

(56) References Cited

PUBLICATIONS

Penaranda et al (IL-7 receptor blockade reverses autoimmune diabetes by promoting inhibition of effector/memory T cells. Proc Natl Acad Sci U S A. Jul. 31, 2012;109(31):12668-7) (Year: 2012).*
Belarif et al (IL-7 receptor influences anti-TNF responsiveness and T cell gut homing in inflammatory bowel disease. J Clin Invest. Apr. 2, 2019;129(5):1910-1925) (Year: 2019).*
Willis et al (Interleukin-7 receptor blockade suppresses adaptive and innate inflammatory responses in experimental colitis. J Inflamm (Lond). Oct. 12, 2012;9(1):39) (Year: 2012).*
McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Chen Zhenlong et al., "The Novel Role of IL-7 Ligation to IL-7 Receptor in Myeloid Cells of Rheumatoid Arthritis and Collagen-Induced Arthritis", The Journal of Immunology, vol. 190, No. 10, May 15, 2013, pp. 5256-5266.
Dooms, Hans, "Interleukin-7: Fuel for the autoimmune attack", Journal of Autoimmunity, London, GB, vol. 45, Jul. 4, 2013 (Jul. 4, 2013), pp. 40-48.
Grabstein K.H et al., "Inhibition of murine B and T lymphopoiesis in vivo by an anti-interleukin 7 monoclonal antibody", The Journal of Experimental Medicine, Jul. 1993, vol. 178, pp. 257-264.
Kondrack Robyn M. et al., "Interleukin 7 Regulates the Survival and Generation of Memory CD4 Cells", Journal of Experimental Medicine, vol. 198, No. 12, Dec. 15, 2003 (Dec. 15, 2003), pp. 1797-1806.
Mccarthy et al., "Altering the Fine Specificity of an Anti-Legionella Single Chain Antibody by a Single Amino Acid Insertion," J. Immuol. Methods, vol. 251, No. 1-2, (2001), pp. 137-149.
Boyman et al., "IL-7/Anti-IL-7 mAb Complexes Restore T Cell Development and Induce Homeostatic T Cell Expansion without Lymphopenia," J. Immunol., vol. 180, No. 11, (2008), pp. 7265-7275.

* cited by examiner

*Primary Examiner* — Elizabeth C. Kemmerer
*Assistant Examiner* — Ashley H. Gao
(74) *Attorney, Agent, or Firm* — Kelly A. Gauger

(57) ABSTRACT

Provided herein are interleukin 7 (IL-7) binding proteins, pharmaceutical compositions and their use in the treatment or prevention of a disease or condition.

Figure 1A:
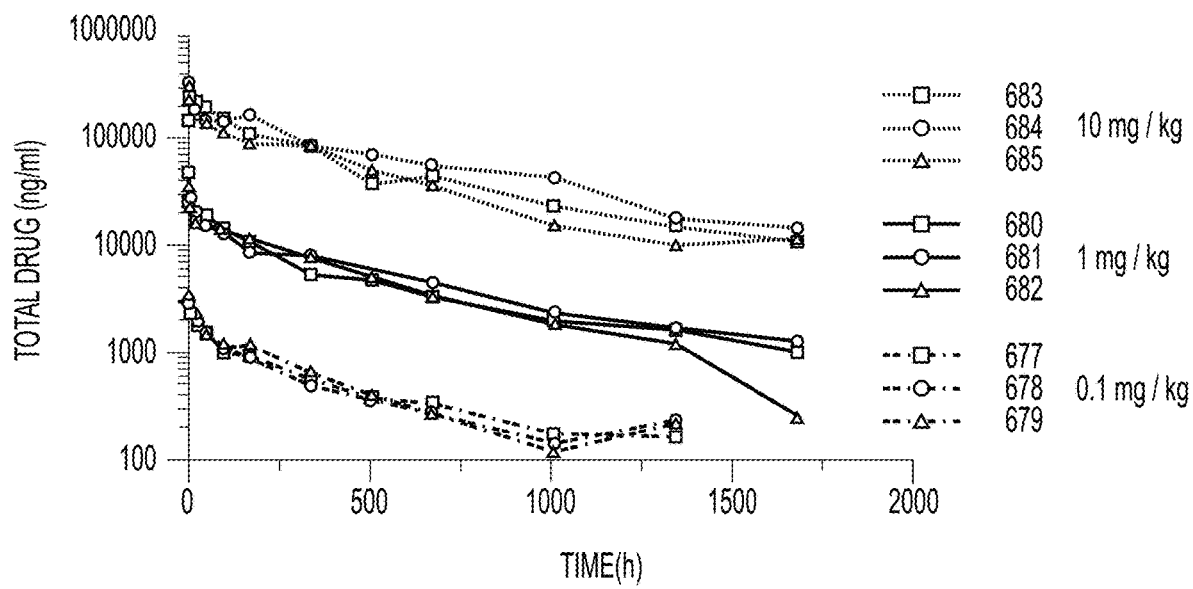

20 Claims, 14 Drawing Sheets
Specification includes a Sequence Listing.

IL-7 BINDING PROTEINS AND THEIR USE IN MEDICAL THERAPY

CROSS REFERENCE TO RELATED APPLICATIONS

This application is a continuation of U.S. application Ser. No. 17/538,431, filed 30 Nov. 2021, which claims the benefit of U.S. Provisional Application No. 63/120,564, filed 2 Dec. 2020, both of which are hereby incorporated by reference in their entireties.

REFERENCE TO SEQUENCE LISTING SUBMITTED ELECTRONICALLY

The instant application contains a Sequence Listing which has been submitted electronically in XML format and is hereby incorporated by reference in its entirety. Said XML copy, created on Aug. 18, 2023, is named PU66978US02_SL.xml and is 66,149 bytes in size.

FIELD OF THE DISCLOSURE

The present disclosure relates to interleukin 7 (IL-7) binding proteins. The disclosure also concerns methods of treating diseases or disorders with IL-7 binding proteins, uses of IL-7 binding proteins, pharmaceutical compositions comprising IL-7 binding proteins and methods of their manufacture. Other aspects of the disclosure will be apparent from the description below.

BACKGROUND TO THE DISCLOSURE

Both altered autoimmune T cell responses and dysfunction of the regulatory network of the immune system play an important role in human autoimmune pathologies, such as multiple sclerosis (MS) and rheumatoid arthritis (Kuchroo et al., (2002) Annu. Rev. Immunol. 20:101-123; Sospedra and Martin (2005) Annu. Rev. Immunol. 23: 683-747; Toh and Miossec (2007) Curr. Opin. Rheumatol. 19:284-288).

Although the etiology and pathogenesis of MS remain unknown, it is generally considered an autoimmune pathology in which autoreactive T cells of pathogenic potential, such as $T_H1$ and $T_H17$ cells, are thought to play an important role. There is evidence that these effector T cells are activated in vivo during the disease process and are attributable to the central nervous system (CNS) inflammation. There is also evidence that these T cells mediate destruction of myelin-expressing cells in lesions of experimental autoimmune encephalomyelitis (EAE) and MS during the active phase of the disease. On the other hand, regulatory T cells ($T_{reg}$) that normally keep pathogenic $T_H1$ and $T_H17$ cells in check are deficient in patients with MS, further tilting the immune system toward a pro-inflammatory state.

IL-7 and IL-7 receptor (IL-7R) are known to play an important role in T cell and B cell development and homeostasis mainly in a thymic environment. In humans, IL-7 is important for T cell development in the thymus and for survival of memory and naïve T cells in the periphery. Indeed, thymic stromal cells, fetal thymus, and bone marrow are sites of IL-7 production.

IL-7 is a four-helix bundle, displaying the conserved up-up-down-down cytokine architecture. Based on the work of McElroy et al. (Structure, 2009, 17:54-65), the helices of IL-7, starting with that closest to the N-terminus, stretch from amino acids 10-26 (Helix A), amino acids 53-63 (Helix B), amino acids 74-91 (Helix C) and amino acids 128-146 (Helix D). A mini-helix is believed to exist between Helix A and Helix B, and stretches from amino acids 40-44. For the purposes of the disclosure, Helices A, B, C and D are referred to as Helices 1, 3, 4 and 5, and the mini-helix is referred to as Helix 2. The loops interconnecting the helices therefore stretch from amino acids 27-39 ("Loop 1" between Helix 1 and 2), 45 to 52 ("Loop 2" between Helix 2 and 3), 64-73 ("Loop 3" between Helix 3 and 4), and 92-127 ("Loop 4" between Helix 4 and 5). The "N-terminal loop" runs from amino acids 1-9, and the "C-terminal loop" from amino acids 147-152.

The IL-7 receptor consists of two subunits, CD127 and a common chain (gamma chain or γc) which is shared by receptors of IL-2, IL-4, IL-9, IL-15, and IL-21. CD127 is also known as IL-7 receptor alpha (IL-7Ra) and p90 IL-7R. Human CD127 (Swiss Prot accession number P16871) has a total of 459 amino acids (20 signal sequence). It comprises a 219 amino acid extra cellular region, a 25 amino acid transmembrane region and a 195 amino acid intracellular region. Both IL-7Ra and γc are required for signal transduction. The crystal structure of an IL-7/IL-7Rα ECD (extracellular domain) complex has been resolved (McElroy et al., supra), but to date there is limited information about the interaction between IL-7 and the functional IL-7Rα/γc receptor complex. The residues of IL-7 importance in this interaction have not been determined, although predictions generally implicate Helix A (Helix 1, herein) and Helix D (Helix 5, herein) in the binding of IL-7 to γc.

Binding of IL-7 to the IL-7R complex activates multiple signaling pathways including the activation of JAK kinases 1 and 3 leading to the phosphorylation and activation of STAT5. This pathway is crucial to the survival of thymic developing T cell precursors because STAT5 activation is required in the induction of the anti-apoptotic protein Bcl-2 and the prevention of the pro-apoptotic protein Bax entry into the mitochondrion. Another IL-7R mediated pathway is the activation of PI3 kinase, resulting in the phosphorylation of the pro-apoptotic protein BAD (BCL2 associated agonist of cell death) and its cytoplasm retention.

Pathogenic CD4+ T cells in multiple sclerosis (MS) are largely from $T_H1$ and $T_H17$ subsets which is reflected by the pro-inflammatory cytokine production from these cells—IFN-γ, IL-17 and GM-CSF etc.

These cytokines contribute to blood-brain-barrier dysfunction, inflammation and activation of resident astrocytes and microglia cells. IL-7 can induce $Th_1$ and $Th_{17}$ phenotypes upon antigen stimulation and effector memory T cells rely on IL-7 for survival and proliferation. The pathogenic autoreactive T cells in MS are maintained by a pool of memory T cells and IL-7 is key for their development, proliferation and activation. Accordingly, it is desirable to develop antagonists of the IL-7/IL-7R pathway. Such antagonists may be therapeutically useful in the treatment of MS and other inflammatory and/or autoimmune diseases and disorders, particularly those in which raised $T_H1$ and/or $T_H17$ cells have been observed.

SUMMARY OF THE DISCLOSURE

Disclosed herein are IL-7 binding proteins, for example an IL-7 binding antibody or an antigen binding fragment thereof.

In one aspect of the invention, there is provided an IL-7 binding protein that binds to one or more amino acid residue within the amino acid sequence set forth in SEQ ID NO:12 of human IL-7. In one embodiment, the IL-7 binding protein protects residues 67 to 81 (SEQ ID NO:12) of IL-7 from deuterium exchange in HDX-MS analysis. In a further embodiment, the IL-7 binding protein protects residues 67 to 80 (SEQ ID NO:16) of IL-7 from deuterium exchange in HDX-MS analysis.

In another aspect of the invention, there is provided an IL-7 binding protein that binds to human IL-7 adjacent an IL-7Rα binding site, with a KD of 100 nM or less as measured by surface plasmon resonance assay. In some embodiments, the IL-7 binding protein inhibits IL-7 binding to IL-7R as measured in an in vitro competitive binding assay as determined using a surface plasmon resonance assay. In other embodiments, the IL-7 binding protein further comprises one or more of CDRH1 as set out in SEQ ID NO:6, CDRH2 as set out in SEQ ID NO:7, CDRH3 as set out in SEQ ID NO:8, CDRL1 as set out in SEQ ID NO:9, CDRL2 as set out in SEQ ID NO:10 and/or CDRL3 as set out in SEQ ID NO:11.

In a further aspect of the invention, the IL-7 binding protein comprises CDRH1 as set out in SEQ ID NO:6, CDRH2 as set out in SEQ ID NO:7, CDRH3 as set out in SEQ ID NO:8, CDRL1 as set out in SEQ ID NO:9, CDRL2 as set out in SEQ ID NO:10 and CDRL3 as set out in SEQ ID NO:11. In some embodiments, the IL-7 binding protein comprises a $V_H$ domain having at least 90% identity to the amino acid sequence set out in SEQ ID NO:4 and/or a $V_L$ domain having at least 90% identity to the amino acid sequence as set out in SEQ ID NO:5. In another embodiment, the IL-7 binding protein comprises a $V_H$ domain as set out in SEQ ID NO:4 and a $V_L$ domain as set out in SEQ ID NO:5. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and position 237 according to EU numbering. In other embodiments, the IL-7 binding protein comprises a scaffold selected from the group consisting of human IgG1 isotype and human IgG4 isotype. In one embodiment, the IL-7 binding protein is of human IgG1 isotype. In another embodiment, the IL-7 binding protein is a monoclonal antibody. In some embodiments, the monoclonal antibody is human, humanized or chimeric. In other embodiments, the IL-7 binding protein comprises a heavy chain having at least 90% identity to the amino acid sequence set out in SEQ ID NO:2 and a light chain having at least 90% identity to the amino acid sequence as set out in SEQ ID NO:3. In one embodiment, the IL-7 binding protein comprises a heavy chain as set out in SEQ ID NO:2 and a light chain as set out in SEQ ID NO:3. In some embodiments, the IL-7 binding protein binds to IL-7 with a KD of 50 nM or less, 10 nM or less, 1 nM or less, or 0.1 nM or less. In another embodiment, the IL-7 binding protein binds to IL-7 and (i) inhibits IL-7 dependent IFN-γ or IL-10 secretion from peripheral blood mononuclear cells with an $IC_{50}$ of 1 nM or less, and/or (ii) inhibits IL-7 dependent STAT5 phosphorylation in CD4+ T cells with an $IC_{50}$ of 1 nM or less. In some embodiments, the IL-7 binding protein inhibits signaling, activation, cytokine production and proliferation of $CD4^+$ T cells and/or CD8+ T cells.

In one aspect of the invention, there is provided a nucleic acid encoding an IL-7 binding protein. In another aspect of the invention, there is provided an expression vector comprising a nucleic acid sequence encoding the IL-7 binding protein. In a further aspect of the invention, there is provided a host cell comprising the nucleic acid sequence encoding the IL-7 binding protein or the expression vector comprising the nucleic acid sequence encoding the IL-7 binding protein.

In another aspect of the invention, there is provided an IL-7 binding protein expressed by the host cell.

In another aspect of the invention, there is provided a method of making an IL-7 binding protein, the method comprising maintaining a host cell comprising a nucleic acid sequence encoding the IL-7 binding protein or the expression vector comprising the nucleic acid sequence encoding the IL-7 binding protein, in a medium to produce the IL-7 binding protein and isolating or purifying the IL-7 binding protein produced by the host cell.

In a further aspect of the invention, there is provided an IL-7 binding protein that competes for binding to IL-7 with the IL-7 binding protein disclosed herein.

In yet another aspect of the invention, there is provided a pharmaceutical composition, comprising a pharmaceutically-acceptable carrier or excipient and an IL-7 binding protein that exhibits binding for IL-7 at an epitope comprising at least 5 contiguous amino acids of a sequence set out in SEQ ID NO:12 or SEQ ID NO:16. In a further aspect of the invention, there is provided a pharmaceutical composition comprising the IL-7 binding protein and a pharmaceutically acceptable carrier or excipient.

In another aspect of the invention, there is provided an IL-7 binding protein for use in therapy. In one aspect of the invention, there is provided a method for the treatment of an autoimmune and/or inflammatory condition in a subject in need thereof, comprising administering to the subject a therapeutically effective amount of the IL-7 binding protein or the pharmaceutical composition. In one aspect of the invention, there is provided an IL-7 binding protein for use in the treatment of an autoimmune and/or inflammatory condition. In another aspect of the invention, there is provided use of an IL-7 binding protein in the manufacture of a medicament for treatment of an autoimmune and/or inflammatory condition. In some embodiments, the autoimmune and/or inflammatory condition is multiple sclerosis, Sjögren's syndrome, rheumatoid arthritis, Crohn's disease, ulcerative colitis or lupus erythematosus. In some embodiments, the multiple sclerosis is clinically isolated syndrome, relapsing remitting, primary progressive or secondary progressive.

In a further aspect of the invention, there is provided a kit comprising the IL-7 binding protein and instructions for use.

In one aspect of the invention, there is provided an IL-7 binding protein comprising CDRH1 as set out in SEQ ID NO:26, CDRH2 as set out in SEQ ID NO:27, CDRH3 as set out in SEQ ID NO:28, CDRL1 as set out in SEQ ID NO:29, CDRL2 as set out in SEQ ID NO:30 and CDRL3 as set out in SEQ ID NO:31. In some embodiments, the IL-7 binding protein comprises a $V_H$ domain having at least 90% identity to the amino acid sequence set out in SEQ ID NO:25 and/or a $V_L$ domain having at least 90% identity to the amino acid sequence as set out in SEQ ID NO:24. In another embodiment, the IL-7 binding protein comprises a $V_H$ domain as set out in SEQ ID NO:25 and a $V_L$ domain as set out in SEQ ID NO:24.

In one aspect of the invention, there is provided an IL-7 binding protein comprising CDRH1 as set out in SEQ ID NO:34, CDRH2 as set out in SEQ ID NO:35, CDRH3 as set out in SEQ ID NO:36, CDRL1 as set out in SEQ ID NO:37, CDRL2 as set out in SEQ ID NO:38 and CDRL3 as set out in SEQ ID NO:39. In some embodiments, the IL-7 binding protein comprises a $V_H$ domain having at least 90% identity to the amino acid sequence set out in SEQ ID NO:33 and/or a $V_L$ domain having at least 90% identity to the amino acid sequence as set out in SEQ ID NO:32. In another embodiment, the IL-7 binding protein comprises a $V_H$ domain as set out in SEQ ID NO:33 and a $V_L$ domain as set out in SEQ ID NO:32.

In one aspect of the invention, there is provided an IL-7 binding protein comprising CDRH1 as set out in SEQ ID NO:42, CDRH2 as set out in SEQ ID NO:43, CDRH3 as set out in SEQ ID NO:44, CDRL1 as set out in SEQ ID NO:45, CDRL2 as set out in SEQ ID NO:46 and CDRL3 as set out in SEQ ID NO:47. In some embodiments, the IL-7 binding protein comprises a $V_H$ domain having at least 90% identity to the amino acid sequence set out in SEQ ID NO:41 and/or a $V_L$ domain having at least 90% identity to the amino acid sequence as set out in SEQ ID NO:40. In another embodiment, the IL-7 binding protein comprises a $V_H$ domain as set out in SEQ ID NO:41 and a $V_L$ domain as set out in SEQ ID NO:40.

In some embodiments, the IL-7 binding protein or an antigen binding fragment thereof binds to one or more residues within the amino acid sequence set forth in SEQ ID NO:12 of human IL-7. In some embodiments, the IL-7 binding protein protects residues 67 to 81 (SEQ ID NO:12) of IL-7 from deuterium exchange in HDX-MS analysis. In some embodiments, the IL-7 binding protein or an antigen binding fragment thereof binds to one or more residues within the amino acid sequence set forth in SEQ ID NO:16 of human IL-7. In some embodiments, the IL-7 binding protein protects residues 67 to 80 (SEQ ID NO:16) of IL-7 from deuterium exchange in HDX-MS analysis. In some embodiments, the IL-7 binding protein binds to an epitope comprising the amino acid sequence set forth in SEQ ID NO:12. In some embodiments, the IL-7 binding protein binds to an epitope comprising at least 50%, 60%, 70%, 80%, 90% or 95% identity to the amino acid sequence set out in SEQ ID NO:12. In some embodiments, the IL-7 binding protein comprises a variable region light chain having at least 80% identity to the amino acid sequence set out in SEQ ID NO:5. In some embodiments, the IL-7 binding protein comprises at least one of (a) a heavy chain CDR1 having at least 80% identity to the amino acid sequence set out in SEQ ID NO:6, (b) a heavy chain CDR2 having at least 80% identity to the amino acid sequence set out in SEQ ID NO:7 or (c) a heavy chain CDR3 having at least 80% identity to the amino acid sequence set out in SEQ ID NO:8. In some embodiments, the IL-7 binding protein comprises at least one of (a) a light chain CDR1 having at least 80% identity to the amino acid sequence set out in SEQ ID NO:9, (b) a light chain CDR2 having at least 80% identity to the amino acid sequence set out in SEQ ID NO:10 or (c) a light chain CDR3 having at least 80% identity to the amino acid sequence set out in SEQ ID NO:11. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to circulating IL-7. In some embodiments, the IL-7 binding protein binds to IL-7 and inhibits IL-7 depending IFN-γ or IL-10 secretion from peripheral blood mononuclear cells with an $IC_{50}$ of 1 nM or less. In some embodiments, the IL-7 binding protein is an isolated IL-7 binding protein. In some embodiments, the IL-7 binding protein binds to IL-7 and inhibits IL-7 depending STAT5 phosphorylation in CD4+ T cells with an $IC_{50}$ of 1 nM or less. In some embodiments, the IL-7 binding protein is a reversible dimer. In some embodiments, the IL-7 binding protein is a dimer. In some embodiments, the IL-7 binding protein is a monomer. In some embodiments, the IL-7 binding protein inhibits signaling, activation, cytokine production and proliferation of $CD4^+$ T cells and/or $CD8^+$ T cells. In some embodiments, the IL-7 binding protein is for use in a therapy. Further disclosed are nucleic acids encoding the IL-7 binding protein. In some embodiments, the nucleic acid comprises a sequence having at least 80% identity to the nucleic acid sequence set out in SEQ ID NO:13 encoding the light chain. In some embodiments, the nucleic acid comprises the nucleic acid sequence set out in SEQ ID NO:13 encoding the light chain. In some embodiments, the nucleic acid comprises a sequence having at least 80% identity to the nucleic acid sequence set out in SEQ ID NO:14 encoding the heavy chain. In some embodiments, the nucleic acid comprises the nucleic acid sequence set out in SEQ ID NO:14 encoding the heavy chain. In some embodiments, the nucleic acid further comprises a sequence having at least 80% identity to the nucleic acid sequence set out in SEQ ID NO:15 encoding a signal peptide. In some embodiments, disclosed herein are vectors comprising a nucleic acid. In some embodiments, the vector comprises a promoter functional in a mammalian cell. Also disclosed are host cells comprising the nucleic acid. In some embodiments, the host cell is a CHO cell. Further disclosed herein are methods for making the IL-7 binding protein comprising maintaining the host cell in a medium to produce the IL-7 binding protein and isolating or purifying the IL-7 binding protein produced by the host cell. In some embodiments, disclosed herein are pharmaceutical compositions comprising the IL-7 binding protein. In some embodiment, the pharmaceutical compositions comprises a pharmaceutically acceptable carrier or excipient. In some embodiments, the pharmaceutical composition further comprises at least one additional therapeutic agent. In some embodiments, the pharmaceutical composition has a pH of 4.5-7.0. In some embodiments, the pharmaceutical composition has a pH of 5.5, 6.0, 6.2 or 6.5. In some embodiments, the pharmaceutical composition or the IL-7 binding protein can be used in a method for the treatment of an autoimmune and/or inflammatory condition in a subject in need thereof, the method comprising administering to the subject a therapeutically effective amount of the pharmaceutical composition or the IL-7 binding protein. In some embodiments, the administering is transarterially, subcutaneously, intradermally, intratumorally, intranodally, intramedullary, intramuscularly, intravenously or intraperitoneally. In some embodiments, the administering is subcutaneously. In some embodiments, the therapeutically effective amount is at least about 0.1 mg/kg, 0.5 mg/kg, 1 mg/kg, 3 mg/kg, 5 mg/kg, 10 mg/kg, 20 mg/kg, 30 mg/kg, or 40 mg/kg. In some embodiments, the therapeutically effective amount is administered to the subject at least about twice every day or once every 1-60 days. In some embodiments, the therapeutically effective amount is administered to the subject once every 4 weeks. In some embodiments, the autoimmune and/or inflammatory condition is Sjögren's syndrome. In some embodiments, the autoimmune and/or inflammatory condition is rheumatoid arthritis. In some embodiments, the autoimmune and/or inflammatory condition is inflammatory bowel disease (IBD). In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes. In some embodiments, the IL-7 binding protein is used in the manufacture of a medicament for the treatment of the autoimmune and/or inflammatory condition. In some embodiments, compounds comprising the IL-7 binding protein are for use in the treatment of the autoimmune and/or inflammatory condition. In some embodiments, the IL-7 binding protein is used for diagnosis of a disease or condition. In some embodiments, the IL-7 binding protein is used for diagnosis of the autoimmune and/or inflammatory condition. In some embodiments, the IL-7 binding protein is bound to a moiety or an antigenic fragment thereof. In some embodiments, the moiety is IL-7 or a fragment thereof. In some embodiments, the IL-7 binding protein is attached directly or indirectly to a solid support. In some embodiments, the IL-7 binding protein is comprised in a kit with instruction for use. In some embodiments, the solid support is comprised in a kit.

Disclosed herein are IL-7 binding proteins or an antigen binding fragment thereof that binds to human IL-7 with a KD of 100 nM or less. In some embodiments, the IL-7 binding protein binds to human IL-7 adjacent IL-7Rα binding site. In some embodiments, the IL-7 binding protein inhibits IL-7 binding to IL-7R as measured in an in vitro competitive binding assay. In some embodiments, a competitive binding assay is an immunoassay. In some embodiment, a competitive binding assay is a surface plasmon resonance assay. In some embodiments, a competitive binding assay is for example ELISA or a radioimmunoassay. In some embodiments, the IL-7 binding protein comprises a variable region light chain having at least 80% identity to the amino acid sequence set out in SEQ ID NO:5. In some embodiments, the IL-7 binding protein comprises at least one of (a) a heavy chain CDR1 having at least 80% identity to the amino acid sequence set out in SEQ ID NO:6, (b) a heavy chain CDR2 having at least 80% identity to the amino acid sequence set out in SEQ ID NO:7 or (c) a heavy chain CDR3 having at least 80% identity to the amino acid sequence set out in SEQ ID NO:8. In some embodiments, the IL-7 binding protein comprises at least one of (a) a light chain CDR1 having at least 80% identity to the amino acid sequence set out in SEQ ID NO:9, (b) a light chain CDR2 having at least 80% identity to the amino acid sequence set out in SEQ ID NO:10 or (c) a light chain CDR3 having at least 80% identity to the amino acid sequence set out in SEQ ID NO:11. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to circulating IL-7. In some embodiments, the IL-7 binding protein is an isolated IL-7 binding protein. In some embodiments, the IL-7 binding protein binds to IL-7 and inhibits IL-7 depending IFN-γ or IL-10 secretion from peripheral blood mononuclear cells with an IC$_{50}$ of 1 nM or less. In some embodiments, the IL-7 binding protein binds to IL-7 and inhibits IL-7 depending STAT5 phosphorylation in CD4+ T cells with an IC$_{50}$ of 1 nM or less. In some embodiments, the IL-7 binding protein inhibits signaling, activation, cytokine production and proliferation of CD4$^+$ T cells and/or CD8$^+$ T cells. In some embodiments, the IL-7 binding protein is a reversible dimer. In some embodiments, the IL-7 binding protein is a dimer. In some embodiments, the IL-7 binding protein is a monomer. In some embodiments, the IL-7 binding protein is for use in a therapy. Further disclosed are nucleic acids encoding the IL-7 binding protein. In some embodiments, the nucleic acid comprises a sequence having at least 80% identity to the nucleic acid sequence set out in SEQ ID NO:13 encoding the light chain. In some embodiments, the nucleic acid comprises the nucleic acid sequence set out in SEQ ID NO:13 encoding the light chain. In some embodiments, the nucleic acid comprises a sequence having at least 80% identity to the nucleic acid sequence set out in SEQ ID NO:14 encoding the heavy chain. In some embodiments, the nucleic acid comprises the nucleic acid sequence set out in SEQ ID NO:14 encoding the heavy chain. In some embodiments, the nucleic acid further comprises a sequence having at least 80% identity to the nucleic acid sequence set out in SEQ ID NO:15 encoding a signal peptide. In some embodiments, disclosed herein are vectors comprising a nucleic acid. In some embodiments, the vector comprises a promoter functional in a mammalian cell. Also disclosed are host cells comprising the nucleic acid. In some embodiments, the host cell is a CHO cell. Further disclosed herein are methods for making the IL-7 binding protein comprising maintaining the host cell in a medium to produce the IL-7 binding protein and isolating or purifying the IL-7 binding protein produced by the host cell. In some embodiments, disclosed herein are pharmaceutical compositions comprising the IL-7 binding protein. In some embodiment, the pharmaceutical compositions comprises a pharmaceutically acceptable carrier or excipient. In some embodiments, the pharmaceutical composition further comprises at least one additional therapeutic agent. In some embodiments, the pharmaceutical composition has a pH of 4.5-7.0. In some embodiments, the pharmaceutical composition has a pH of 5.5, 6.0, 6.2 or 6.5. In some embodiments, the pharmaceutical composition or the IL-7 binding protein can be used in a method for the treatment of an autoimmune and/or inflammatory condition in a subject in need thereof, the method comprising administering to the subject a therapeutically effective amount of the pharmaceutical composition or the IL-7 binding protein. In some embodiments, the administering is transarterially, subcutaneously, intradermally, intratumorally, intranodally, intramedullary, intramuscularly, intravenously or intraperitoneally. In some embodiments, the administering is subcutaneously. In some embodiments, the therapeutically effective amount is at least about 0.1 mg/kg, 0.5 mg/kg, 1 mg/kg, 3 mg/kg, 5 mg/kg, 10 mg/kg, 20 mg/kg, 30 mg/kg, or 40 mg/kg. In some embodiments, the therapeutically effective amount is administered to the subject at least about twice every day or once every 1-60 days. In some embodiments, the therapeutically effective amount is administered to the subject once every 4 weeks. In some embodiments, the autoimmune and/or inflammatory condition is Sjögren's syndrome. In some embodiments, the autoimmune and/or inflammatory condition is IBD. In some embodiments, the autoimmune and/or inflammatory condition is rheumatoid arthritis. In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes. In some embodiments, the IL-7 binding protein is used in the manufacture of a medicament for the treatment of the autoimmune and/or inflammatory condition. In some embodiments, provided are compounds comprising the IL-7 binding protein are for use in the treatment of the autoimmune and/or inflammatory condition. In some embodiments, the IL-7 binding protein is used for diagnosis of a disease or condition. In some embodiments, the IL-7 binding protein is used for diagnosis of the autoimmune and/or inflammatory condition. In some embodiments, the IL-7 binding protein is bound to a moiety or an antigenic fragment thereof. In some embodiments, the moiety is IL-7 or a fragment thereof. In some embodiments, the IL-7 binding protein is attached directly or indirectly to a solid support. In some embodiments, the IL-7 binding protein is comprised in a kit with instruction for use. In some embodiments, the solid support is comprised in a kit.

Disclosed herein are IL-7 binding proteins comprising a variable region light chain having at least 95% identity to the amino acid sequence set out in SEQ ID NO:5. In some embodiments, the IL-7 binding protein comprises at least one of (a) a heavy chain CDR1 having at least 80% identity to the amino acid sequence set out in SEQ ID NO:6, (b) a heavy chain CDR2 having at least 80% identity to the amino acid sequence set out in SEQ ID NO:7 or (c) a heavy chain CDR3 having at least 80% identity to the amino acid sequence set out in SEQ ID NO:8. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid set sequence out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, the IL-7 binding protein binds to circulating IL-7. In some embodiments, the IL-7 binding protein binds to IL-7 and inhibits IL-7 depending IFN-γ or IL-10 secretion from peripheral blood mononuclear cells with an $IC_{50}$ of 1 nM or less. In some embodiments, the IL-7 binding protein is an isolated IL-7 binding protein. In some embodiments, the IL-7 binding protein binds to IL-7 and inhibits IL-7 depending STAT5 phosphorylation in CD4+ T cells with an $IC_{50}$ of 1 nM or less. In some embodiments, the IL-7 binding protein inhibits signaling, activation, cytokine production and proliferation of $CD4^+$ T cells and/or $CD8^+$ T cells. In some embodiments, the IL-7 binding protein is a reversible dimer. In some embodiments, the IL-7 binding protein is a dimer. In some embodiments, the IL-7 binding protein is a monomer. In some embodiments, the IL-7 binding protein is for use in a therapy. Further disclosed are nucleic acids encoding the IL-7 binding protein. In some embodiments, the nucleic acid comprises a sequence having at least 80% identity to the nucleic acid sequence set out in SEQ ID NO:13 encoding the light chain. In some embodiments, the nucleic acid comprises the nucleic acid sequence set out in SEQ ID NO:13 encoding the light chain. In some embodiments, the nucleic acid comprises a sequence having at least 80% identity to the nucleic acid sequence set out in SEQ ID NO:14 encoding the heavy chain. In some embodiments, the nucleic acid comprises the nucleic acid sequence set out in SEQ ID NO:14 encoding the heavy chain. In some embodiments, the nucleic acid further comprises a sequence having at least 80% identity to the nucleic acid sequence set out in SEQ ID NO:15 encoding a signal peptide. In some embodiments, disclosed herein are vectors comprising a nucleic acid. In some embodiments, the vector comprises a promoter functional in a mammalian cell. Also disclosed are host cells comprising the nucleic acid. In some embodiments, the host cell is a CHO cell. Further disclosed herein are methods for making the IL-7 binding protein comprising maintaining the host cell in a medium to produce the IL-7 binding protein and isolating or purifying the IL-7 binding protein produced by the host cell. In some embodiments, disclosed herein are pharmaceutical compositions comprising the IL-7 binding protein. In some embodiment, the pharmaceutical compositions comprises a pharmaceutically acceptable carrier or excipient. In some embodiments, the pharmaceutical composition further comprises at least one additional therapeutic agent. In some embodiments, the pharmaceutical composition has a pH of 4.5-7.0. In some embodiments, the pharmaceutical composition has a pH of 5.5, 6.0, 6.2 or 6.5. In some embodiments, the pharmaceutical composition or the IL-7 binding protein can be used in a method for the treatment of an autoimmune and/or inflammatory condition in a subject in need thereof, the method comprising administering to the subject a therapeutically effective amount of the pharmaceutical composition or the IL-7 binding protein. In some embodiments, the administering is transarterially, subcutaneously, intradermally, intratumorally, intranodally, intramedullary, intramuscularly, intravenously or intraperitoneally. In some embodiments, the administering is subcutaneously. In some embodiments, the therapeutically effective amount is at least about 0.1 mg/kg, 0.5 mg/kg, 1 mg/kg, 3 mg/kg, 5 mg/kg, 10 mg/kg, 20 mg/kg, 30 mg/kg, or 40 mg/kg. In some embodiments, the therapeutically effective amount is administered to the subject at least about twice every day or once every 1-60 days. In some embodiments, the therapeutically effective amount is administered to the subject once every 4 weeks. In some embodiments, the autoimmune and/or inflammatory condition is Sjögren's syndrome. In some embodiments, the autoimmune and/or inflammatory condition is rheumatoid arthritis. In some embodiments, the autoimmune and/or inflammatory condition is IBD. In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes. In some embodiments, the IL-7 binding protein is used in the manufacture of a medicament for the treatment of the autoimmune and/or inflammatory condition. In some embodiments, compounds comprising the IL-7 binding protein are for use in the treatment of the autoimmune and/or inflammatory condition. In some embodiments, the IL-7 binding protein is used for diagnosis of a disease or condition. In some embodiments, the IL-7 binding protein is used for diagnosis of the autoimmune and/or inflammatory condition. In some embodiments, the IL-7 binding protein is bound to a moiety or an antigenic fragment thereof. In some embodiments, theta moiety is IL-7 or a fragment thereof. In some embodiments, the IL-7 binding protein is attached directly or indirectly to a solid support. In some embodiments, the IL-7 binding protein is comprised in a kit with instruction for use. In some embodiments, the solid support is comprised in a kit.

Disclosed herein are IL-7 binding proteins or an antigen binding fragment thereof comprising a heavy chain CDR1 having at least 80% identity to the amino acid sequence set out in SEQ ID NO:6, a heavy chain CDR2 having at least 80% identity to the amino acid sequence set out in SEQ ID NO:7 and a heavy chain CDR3 having at least 80% identity to the amino acid sequence set out in SEQ ID NO:8. In some embodiments, the IL-7 binding protein comprises a variable region light chain having at least 80% identity to the amino acid sequence set out in SEQ ID NO:5 In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, the IL-7 binding protein binds to circulating IL-7. In some embodiments, the IL-7 binding protein is an isolated IL-7 binding protein. In some embodiments, the IL-7 binding protein binds to IL-7 and inhibits IL-7 depending IFN-γ or IL-10 secretion from peripheral blood mononuclear cells with an $IC_{50}$ of 1 nM or less. In some embodiments, the IL-7 binding protein binds to IL-7 and inhibits IL-7 depending STAT5 phosphorylation in CD4+ T cells with an $IC_{50}$ of 1 nM or less. In some embodiments, the IL-7 binding protein inhibits signaling, activation, cytokine production and proliferation of $CD4^+$ T cells and/or $CD8^+$ T cells. In some embodiments, the IL-7 binding protein is a reversible dimer. In some embodiments, the IL-7 binding protein is a dimer. In some embodiments, the IL-7 binding protein is a monomer. In some embodiments, the IL-7 binding protein is for use in a therapy. Further disclosed are nucleic acids encoding the IL-7 binding protein. In some embodiments, the nucleic acid comprises a sequence having at least 80% identity to the nucleic acid sequence set out in SEQ ID NO:13 encoding the light chain. In some embodiments, the nucleic acid comprises the nucleic acid sequence set out in SEQ ID NO:13 encoding the light chain. In some embodiments, the nucleic acid comprises a sequence having at least 80% identity to the nucleic acid sequence set out in SEQ ID NO:14 encoding the heavy chain. In some embodiments, the nucleic acid comprises the nucleic acid sequence set out in SEQ ID NO:14 encoding the heavy chain. In some embodiments, the nucleic acid further comprises a sequence having at least 80% identity to the nucleic acid sequence set out in SEQ ID NO:15 encoding a signal peptide. In some embodiments, disclosed herein are vectors comprising a nucleic acid. In some embodiments, the vector comprises a promoter functional in a mammalian cell. Also disclosed are host cells comprising the nucleic acid. In some embodiments, the host cell is a CHO cell. Further disclosed herein are methods for making the IL-7 binding protein comprising maintaining the host cell in a medium to produce the IL-7 binding protein and isolating or purifying the IL-7 binding protein produced by the host cell. In some embodiments, disclosed herein are pharmaceutical compositions comprising the IL-7 binding protein. In some embodiment, the pharmaceutical compositions comprises a pharmaceutically acceptable carrier or excipient. In some embodiments, the pharmaceutical composition further comprises at least one additional therapeutic agent. In some embodiments, the pharmaceutical composition has a pH of 4.5-7.0. In some embodiments, the pharmaceutical composition has a pH of 5.5, 6.0, 6.2 or 6.5. In some embodiments, the pharmaceutical composition or the IL-7 binding protein can be used in a method for the treatment of an autoimmune and/or inflammatory condition in a subject in need thereof, the method comprising administering to the subject a therapeutically effective amount of the pharmaceutical composition or the IL-7 binding protein. In some embodiments, the administering is transarterially, subcutaneously, intradermally, intratumorally, intranodally, intramedullary, intramuscularly, intravenously or intraperitoneally. In some embodiments, the administering is subcutaneously. In some embodiments, the therapeutically effective amount is at least about 0.1 mg/kg, 0.5 mg/kg, 1 mg/kg, 3 mg/kg, 5 mg/kg, 10 mg/kg, 20 mg/kg, 30 mg/kg, or 40 mg/kg. In some embodiments, the therapeutically effective amount is administered to the subject at least about twice every day or once every 1-60 days. In some embodiments, the therapeutically effective amount is administered to the subject once every 4 weeks. In some embodiments, the autoimmune and/or inflammatory condition is Sjögren's syndrome. In some embodiments, the autoimmune and/or inflammatory condition is rheumatoid arthritis. In some embodiments, the autoimmune and/or inflammatory condition is IBD. In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes. In some embodiments, the IL-7 binding protein is used in the manufacture of a medicament for the treatment of the autoimmune and/or inflammatory condition. In some embodiments, compounds comprising the IL-7 binding protein are for use in the treatment of the autoimmune and/or inflammatory condition. In some embodiments, the IL-7 binding protein is used for diagnosis of a disease or condition. In some embodiments, the IL-7 binding protein is used for diagnosis of the autoimmune and/or inflammatory condition. In some embodiments, the IL-7 binding protein is bound to a moiety or an antigenic fragment thereof. In some embodiments, the moiety is IL-7 or a fragment thereof. In some embodiments, the IL-7 binding protein is attached directly or indirectly to a solid support. In some embodiments, the IL-7 binding protein is comprised in a kit with instruction for use. In some embodiments, the solid support is comprised in a kit.

Disclosed herein are IL-7 binding proteins or an antigen binding fragment thereof comprising a light chain CDR1 having at least 80% identity to the amino acid sequence set out in SEQ ID NO:9, a light chain CDR2 having at least 80% identity to the amino acid sequence set out in SEQ ID NO:10 and a light chain CDR3 having at least 80% identity to the amino acid sequence set out in SEQ ID NO:11. In some embodiments, the IL-7 binding protein comprises a variable region light chain having at least 80% identity to the amino acid sequence set out in SEQ ID NO:5. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid set sequence out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, the IL-7 binding protein binds to circulating IL-7. In some embodiments, the IL-7 binding protein is an isolated IL-7 binding protein. In some embodiments, the IL-7 binding protein binds to IL-7 and inhibits IL-7 depending IFN-γ or IL-10 secretion from peripheral blood mononuclear cells with an $IC_{50}$ of 1 nM or less. In some embodiments, the IL-7 binding protein binds to IL-7 and inhibits IL-7 depending STAT5 phosphorylation in CD4+ T cells with an $IC_{50}$ of 1 nM or less. In some embodiments, the IL-7 binding protein inhibits signaling, activation, cytokine production and proliferation of $CD4^+$ T cells and/or $CD8^+$ T cells. In some embodiments, the IL-7 binding protein is a reversible dimer. In some embodiments, the IL-7 binding protein is a dimer. In some embodiments, the IL-7 binding protein is a monomer. In some embodiments, the IL-7 binding protein is for use in a therapy. Further disclosed are nucleic acids encoding the IL-7 binding protein. In some embodiments, the nucleic acid comprises a sequence having at least 80% identity to the nucleic acid sequence set out in SEQ ID NO:13 encoding the light chain. In some embodiments, the nucleic acid comprises the nucleic acid sequence set out in SEQ ID NO:13 encoding the light chain. In some embodiments, the nucleic acid comprises a sequence having at least 80% identity to the nucleic acid sequence set out in SEQ ID NO:14 encoding the heavy chain. In some embodiments, the nucleic acid comprises the nucleic acid sequence set out in SEQ ID NO:14 encoding the heavy chain. In some embodiments, the nucleic acid further comprises a sequence having at least 80% identity to the nucleic acid sequence set out in SEQ ID NO:15 encoding a signal peptide. In some embodiments, disclosed herein are vectors comprising a nucleic acid. In some embodiments, the vector comprises a promoter functional in a mammalian cell. Also disclosed are host cells comprising the nucleic acid. In some embodiments, the host cell is a CHO cell. Further disclosed herein are methods for making the IL-7 binding protein comprising maintaining the host cell in a medium to produce the IL-7 binding protein and isolating or purifying the IL-7 binding protein produced by the host cell. In some embodiments, disclosed herein are pharmaceutical compositions comprising the IL-7 binding protein. In some embodiment, the pharmaceutical compositions comprises a pharmaceutically acceptable carrier or excipient. In some embodiments, the pharmaceutical composition further comprises at least one additional therapeutic agent. In some embodiments, the pharmaceutical composition has a pH of 4.5-7.0. In some embodiments, the pharmaceutical composition has a pH of 5.5, 6.0, 6.2 or 6.5. In some embodiments, the pharmaceutical composition or the IL-7 binding protein can be used in a method for the treatment of an autoimmune and/or inflammatory condition in a subject in need thereof, the method comprising administering to the subject a therapeutically effective amount of the pharmaceutical composition or the IL-7 binding protein. In some embodiments, the administering is transarterially, subcutaneously, intradermally, intratumorally, intranodally, intramedullary, intramuscularly, intravenously or intraperitoneally. In some embodiments, the administering is subcutaneously. In some embodiments, the therapeutically effective amount is at least about 0.1 mg/kg, 0.5 mg/kg, 1 mg/kg, 3 mg/kg, 5 mg/kg, 10 mg/kg, 20 mg/kg, 30 mg/kg, or 40 mg/kg. In some embodiments, the therapeutically effective amount is administered to the subject at least about twice every day or once every 1-60 days. In some embodiments, the therapeutically effective amount is administered to the subject once every 4 weeks. In some embodiments, the autoimmune and/or inflammatory condition is Sjögren's syndrome. In some embodiments, the autoimmune and/or inflammatory condition is rheumatoid arthritis. In some embodiments, the autoimmune and/or inflammatory condition is IBD. In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes. In some embodiments, the IL-7 binding protein is used in the manufacture of a medicament for the treatment of the autoimmune and/or inflammatory condition. In some embodiments, compounds comprising the IL-7 binding protein are for use in the treatment of the autoimmune and/or inflammatory condition. In some embodiments, the IL-7 binding protein is used for diagnosis of a disease or condition. In some embodiments, the IL-7 binding protein is used for diagnosis of the autoimmune and/or inflammatory condition. In some embodiments, the IL-7 binding protein is bound to a moiety or an antigenic fragment thereof. In some embodiments, the moiety is IL-7 or a fragment thereof. In some embodiments, the IL-7 binding protein is attached directly or indirectly to a solid support. In some embodiments, the IL-7 binding protein is comprised in a kit with instruction for use. In some embodiments, the solid support is comprised in a kit.

Disclosed herein are pharmaceutical compositions, comprising a pharmaceutically-acceptable carrier and an IL-7 binding protein or an antigen binding fragment thereof that exhibits binding specificity for IL-7 at an epitope comprising at least 5 contiguous amino acids of a sequence set out in SEQ ID NO:12. In some embodiments, the IL-7 binding protein exhibits binding specificity for IL-7 at an epitope comprising at least 5 contiguous amino acids of a sequence having at least about 50%, 60%, 70%, 80%, 90% or 95% identity to the amino acid sequence set out in SEQ ID NO:12. In some embodiments, the IL-7 binding proteins comprises a light chain CDR1 having at least 80% identity to the amino acid sequence set out in SEQ ID NO:9, a light chain CDR2 having at least 80% identity to the amino acid sequence set out in SEQ ID NO:10 and a light chain CDR3 having at least 80% identity to the amino acid sequence set out in SEQ ID NO:11. In some embodiments, the IL-7 binding protein comprises a variable region light chain having at least 80% identity to the amino acid sequence set out in SEQ ID NO:5. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, the pharmaceutical composition further comprises at least one additional therapeutic agent. In some embodiments, the pharmaceutical composition has a pH of 4.5-7.0. In some embodiments, the pharmaceutical composition has a pH of 5.5, 6.0, 6.2 or 6.5. In some embodiments, the pharmaceutical composition can be used in a method for the treatment of an autoimmune and/or inflammatory condition in a subject in need thereof, the method comprising administering to the subject a therapeutically effective amount of the pharmaceutical composition. In some embodiments, the administering is transarterially, subcutaneously, intradermally, intratumorally, intranodally, intramedullary, intramuscularly, intravenously or intraperitoneally. In some embodiments, the administering is subcutaneously. In some embodiments, the therapeutically effective amount is at least about 0.1 mg/kg, 0.5 mg/kg, 1 mg/kg, 3 mg/kg, 5 mg/kg, 10 mg/kg, 20 mg/kg, 30 mg/kg, or 40 mg/kg. In some embodiments, the therapeutically effective amount is administered to the subject at least about twice every day or once every 1-60 days. In some embodiments, the therapeutically effective amount is administered to the subject once every 4 weeks. In some embodiments, the autoimmune and/or inflammatory condition is Sjögren's syndrome. In some embodiments, the autoimmune and/or inflammatory condition is rheumatoid arthritis. In some embodiments, the autoimmune and/or inflammatory condition is IBD. In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes. In some embodiments, the pharmaceutical composition is comprised in a kit with instruction for use. In some embodiments, the pharmaceutical composition is a stable liquid aqueous pharmaceutical formulation comprising an anti-human IL-7 binding protein described herein at a concentration of 20 to 150 mg/ml, a tonicity agent, a surfactant, and a buffer system having a pH of 4.0 to 8.0.

Disclosed herein are methods for treating an autoimmune and/or inflammatory condition by administering to a subject an IL-7 binding protein or an antigen binding fragment thereof. In some embodiments, the IL-7 binding protein comprises a light chain CDR1 having at least 80% identity to the amino acid sequence set out in SEQ ID NO:9, a light chain CDR2 having at least 80% identity to the amino acid sequence set out in SEQ ID NO:10, and a light chain CDR3 having at least 80% identity to the amino acid sequence set out in SEQ ID NO:11. In some embodiments, the IL-7 binding protein comprises a variable region light chain having at least 80% identity to the amino acid sequence set out in SEQ ID NO:5. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, the administering is transarterially, subcutaneously, intradermally, intratumorally, intranodally, intramedullary, intramuscularly, intravenously or intraperitoneally. In some embodiments, the administering is subcutaneously. In some embodiments, the therapeutically effective amount is at least about 0.1 mg/kg, 0.5 mg/kg, 1 mg/kg, 3 mg/kg, 5 mg/kg, 10 mg/kg, 20 mg/kg, 30 mg/kg, or 40 mg/kg. In some embodiments, the therapeutically effective amount is administered to the subject at least about twice every day or once every 1-60 days. In some embodiments, the therapeutically effective amount is administered to the subject once every 4 weeks. In some embodiments, the autoimmune and/or inflammatory condition is Sjögren's syndrome. In some embodiments, the autoimmune and/or inflammatory condition is rheumatoid arthritis. In some embodiments, the autoimmune and/or inflammatory condition is IBD. In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes.

Disclosed herein are use of an IL-7 binding protein or an antigen binding fragment thereof in the manufacture of a medicament for the treatment of an autoimmune and/or inflammatory condition. In some embodiments, the IL-7 binding protein comprises a light chain CDR1 having at least 80% identity to the amino acid sequence set out in SEQ ID NO:9, a light chain CDR2 having at least 80% identity to the amino acid sequence set out in SEQ ID NO:10 and a light chain CDR3 having at least 80% identity to the amino acid sequence set out in SEQ ID NO:11. In some embodiments, the IL-7 binding protein comprises a variable region light chain having at least 80% identity to the amino acid sequence set out in SEQ ID NO:5. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, the autoimmune and/or inflammatory condition is Sjögren's syndrome. In some embodiments, the autoimmune and/or inflammatory condition is rheumatoid arthritis. In some embodiments, the autoimmune and/or inflammatory condition is IBD. In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes.

Disclosed herein are IL-7 binding proteins or an antigen binding fragment thereof for use in the treatment of an autoimmune and/or inflammatory condition. In some embodiments, the IL-7 binding proteins comprises a light chain CDR1 having at least 80% identity to the amino acid sequence set out in SEQ ID NO:9, a light chain CDR2 having at least 80% identity to the amino acid sequence set out in SEQ ID NO:10 and a light chain CDR3 having at least 80% identity to the amino acid sequence set out in SEQ ID NO:11. In some embodiments, the IL-7 binding protein comprises a variable region light chain having at least 80% identity to the amino acid sequence set out in SEQ ID NO:5.

In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, the autoimmune and/or inflammatory condition is Sjögren's syndrome. In some embodiments, the autoimmune and/or inflammatory condition is rheumatoid arthritis. In some embodiments, the autoimmune and/or inflammatory condition is IBD. In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes.

Disclosed herein are use of an IL-7 binding protein or an antigen binding fragment thereof for diagnosis of a disease or condition. In some embodiments, the IL-7 binding proteins comprises a light chain CDR1 having at least 80% identity to the amino acid sequence set out in SEQ ID NO:9, a light chain CDR2 having at least 80% identity to the amino acid sequence set out in SEQ ID NO:10 and a light chain CDR3 having at least 80% identity to the amino acid sequence set out in SEQ ID NO:11. In some embodiments, the IL-7 binding protein comprises a variable region light chain having at least 80% identity to the amino acid sequence set out in SEQ ID NO:5. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, the disease or condition is an autoimmune and/or inflammatory condition. In some embodiments, the autoimmune and/or inflammatory condition is Sjögren's syndrome. In some embodiments, the autoimmune and/or inflammatory condition is rheumatoid arthritis. In some embodiments, the autoimmune and/or inflammatory condition is IBD. In some embodiments, the autoimmune and/or inflammatory condition is multiple sclerosis. In some embodiments, the multiple sclerosis is clinically isolated syndrome, relapsing-remitting, primary progressive or secondary progressive. In some embodiments, the autoimmune and/or inflammatory condition is Crohn's disease. In some embodiments, the autoimmune and/or inflammatory condition is ulcerative colitis. In some embodiments, the autoimmune and/or inflammatory condition is lupus erythematosus. In some embodiments, the autoimmune and/or inflammatory condition is diabetes, for example type I diabetes. In some embodiments, detection of binding of an IL-7 binding protein disclosed herein is indicative of a presence of IL-7. In some embodiments, a level of IL-7 is measured in a subject or on/in a sample obtained from a subject. In some embodiments, measuring a level of IL-7 can be performed by a method and assay known in the art. In some embodiments, a level of IL-7 is compared to a reference level of IL-7. In some embodiments, a references level is indicative of a normal, non-diseases, disease, or disease stage. In some embodiments, a level of IL-7 is measured multiple times in a subject or from multiple samples obtained from a subject.

Disclosed herein is a solid support comprising an IL-7 binding protein or an antigen binding fragment thereof. In some embodiments, the solid support is an array. In some embodiments, the IL-7 binding protein is attached directly or indirectly to a solid support. In some embodiments, the IL-7 binding proteins comprises a light chain CDR1 having at least 80% identity to the amino acid sequence set out in SEQ ID NO:9, a light chain CDR2 having at least 80% identity to the amino acid sequence set out in SEQ ID NO:10 and a light chain CDR3 having at least 80% identity to the amino acid sequence set out in SEQ ID NO:11. In some embodiments, the IL-7 binding protein comprises a variable region light chain having at least 80% identity to the amino acid sequence set out in SEQ ID NO:5. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, a device comprises the solid support and a processor for detecting a signal, the signal is indicative of a binding of a moiety to the IL-7 binding protein. In some embodiments, the IL-7 binding protein is comprised in a kit with instruction for use. In some embodiments, the solid support is comprised in a kit.

Further disclosed herein is a syringe or autoinjector device comprising an IL-7 binding protein or an antigen binding fragment thereof. In some embodiments, the IL-7 binding proteins comprises a light chain CDR1 having at least 80% identity to the amino acid sequence set out in SEQ ID NO:9, a light chain CDR2 having at least 80% identity to the amino acid sequence set out in SEQ ID NO:10 and a light chain CDR3 having at least 80% identity to the amino acid sequence set out in SEQ ID NO:11. In some embodiments, the IL-7 binding protein comprises a variable region light chain having at least 80% identity to the amino acid sequence set out in SEQ ID NO:5. In some embodiments, the IL-7 binding protein comprises a variable region light chain having the amino acid sequence set out in SEQ ID NO:5. In some embodiments, the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8. In some embodiments, the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11. In some embodiments, the IL-7 binding protein comprises a variable region heavy chain having at least 80% identity to the amino acid sequence set out in SEQ ID NO:4. In some embodiments, the IL-7 binding protein comprises a variable region heavy chain comprising the amino acid sequence set out in SEQ ID NO:4. In some embodiments, the IL-7 binding protein comprises a light chain having at least 80% identity to the amino acid sequence set out in SEQ ID NO:3. In some embodiments, the IL-7 binding protein comprises a light chain comprising the amino acid sequence set out in SEQ ID NO:3. In some embodiments, the IL-7 binding protein comprises a heavy chain having at least 80% identity to the amino acid sequence set out in SEQ ID NO:2. In some embodiments, the IL-7 binding protein comprises a heavy chain comprising the amino acid sequence set out in SEQ ID NO:2. In some embodiments, the IL-7 binding protein comprises a heavy chain comprising the amino acid sequence set out in SEQ ID NO:2 and a light chain comprising the amino acid sequence set out in SEQ ID NO:3. In some embodiments, the IL-7 binding protein is an antibody or an antigen-binding portion thereof. In some embodiments, the antibody is a monoclonal antibody. In some embodiments, the monoclonal antibody is an IgG antibody. In some embodiments, the antibody is an IgG1 isotype antibody. In some embodiments, the monoclonal antibody is an IgG4 isotype antibody. In some embodiments, the IL-7 binding protein comprises a constant region such that the IL-7 binding protein has reduced ADCC and/or complement activation or effector functionality. In some embodiments, the IL-7 binding protein comprises a heavy chain Fc domain having an alanine residue at position 235 and/or position 237 according to EU numbering. In some embodiments, the IL-7 binding protein is human, humanized or chimeric. In some embodiments, the IL-7 binding protein is humanized. In some embodiments, the IL-7 binding protein is human. In some embodiments, the IL-7 binding protein binds to and neutralizes IL-7. In some embodiments, the IL-7 binding protein binds to native IL-7. In some embodiments, the syringe or autoinjector device is comprised in a kit with instruction for use.

Other aspects and embodiments of the disclosure will be apparent from the detailed description that follows.

DESCRIPTION OF DRAWINGS/FIGURES

Figure 1B:
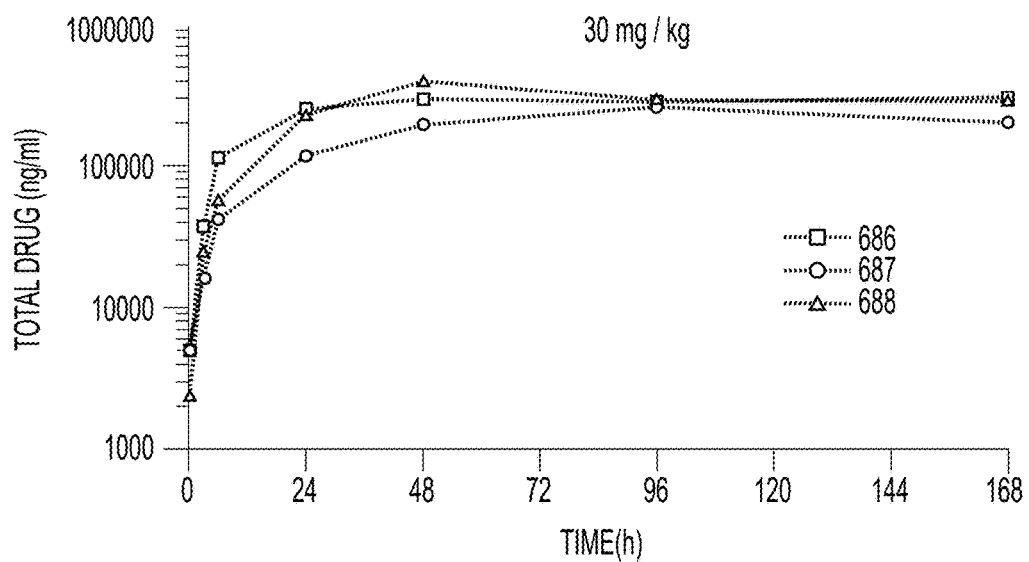
Figure 1C:
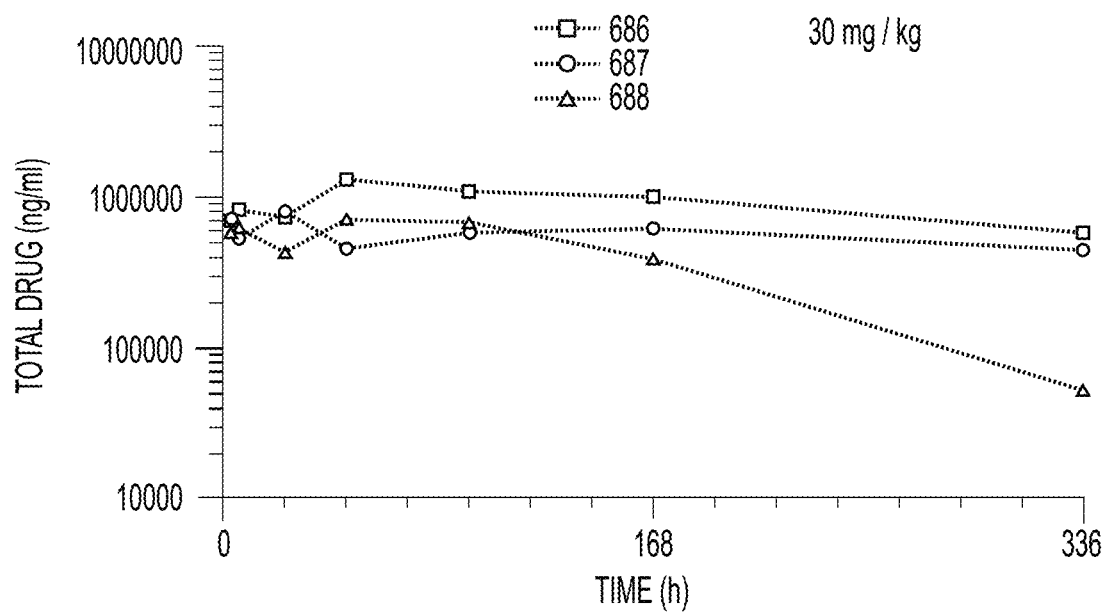

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A: illustrates the concentration of DRSPAI-L7B in animals dosed (i.v.) with a DRSPAI-L7B target dose of 0.1 mg/kg, 1 mg/kg or 10 mg/kg. FIG. 1B and FIG. 1C illustrate the concentration of subcutaneous weekly doses with a repeat target dose of 30 mg/kg, FIG. 1B following dose 1 and FIG. 1C following doses 4. Serum samples were collected at the indicated timepoints and DRSPAI-L7B was quantified by Gyrolab immunoassay.

Figure 2A:
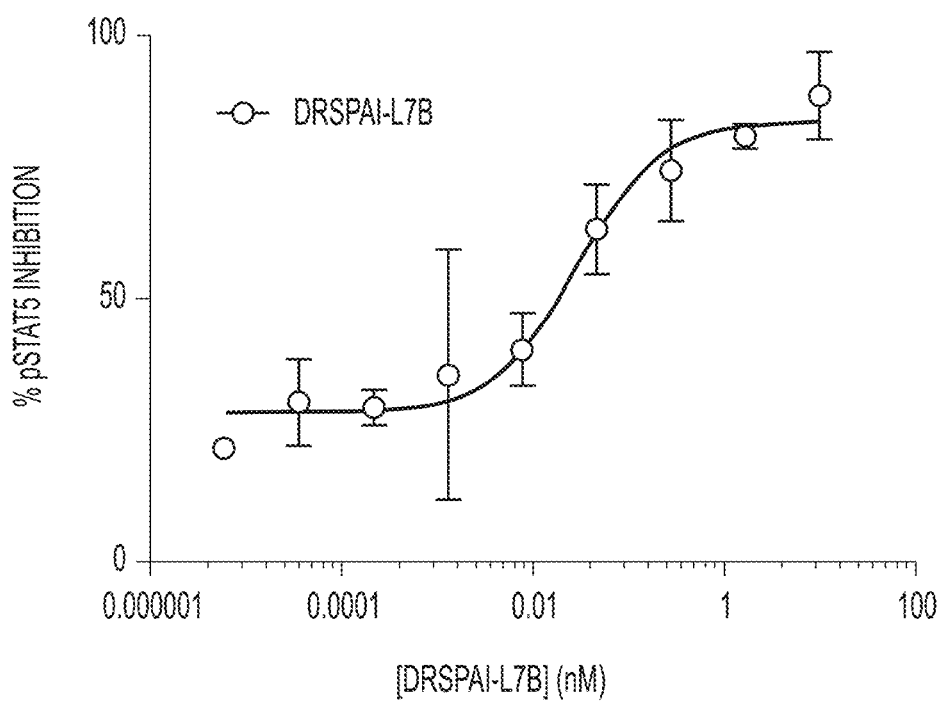
Figure 2B:
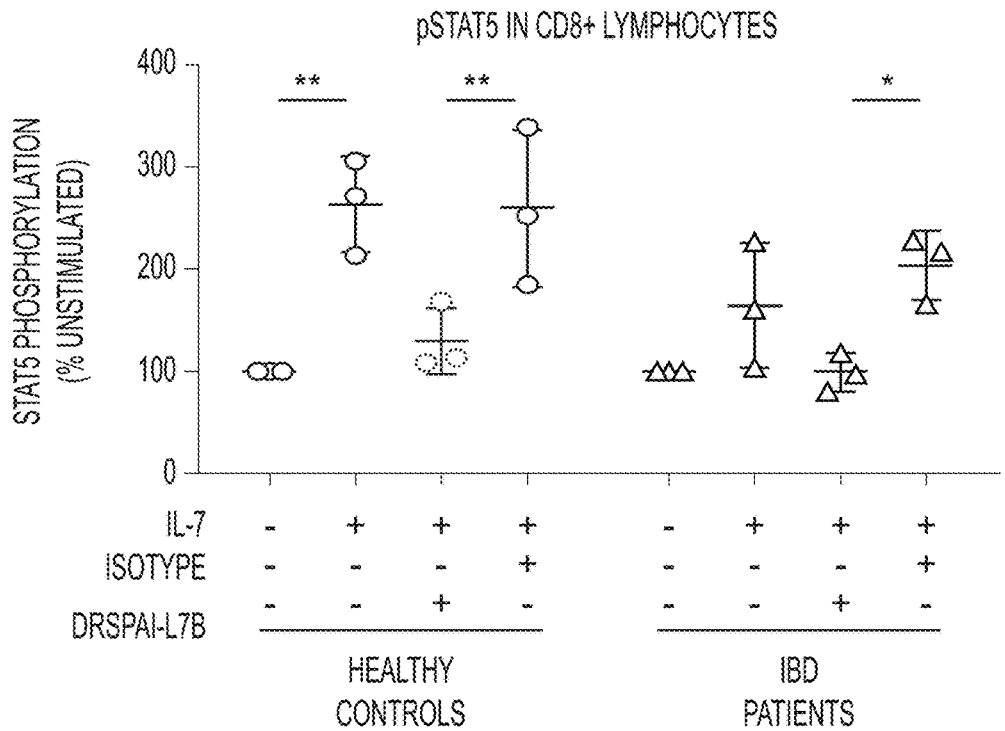

FIG. 2A: illustrates % pSTAT5 inhibition of whole blood obtained from healthy donors that was stimulated with IL-7 in the presence of DRSPAI-L7B. FIG. 2B illustrates STAT5 phosphorylation in CD8+ T cells, FIG. 2C CD4+ T cells, FIG. 2D CD3+ T cells, from peripheral blood mononuclear cells (PBMCs) obtained from healthy donors or IBD patients, stimulated with rhIL-7 in the presence of DRSPAI-L7B or anti-RSV antibody (isotype control).

Figure 3A:
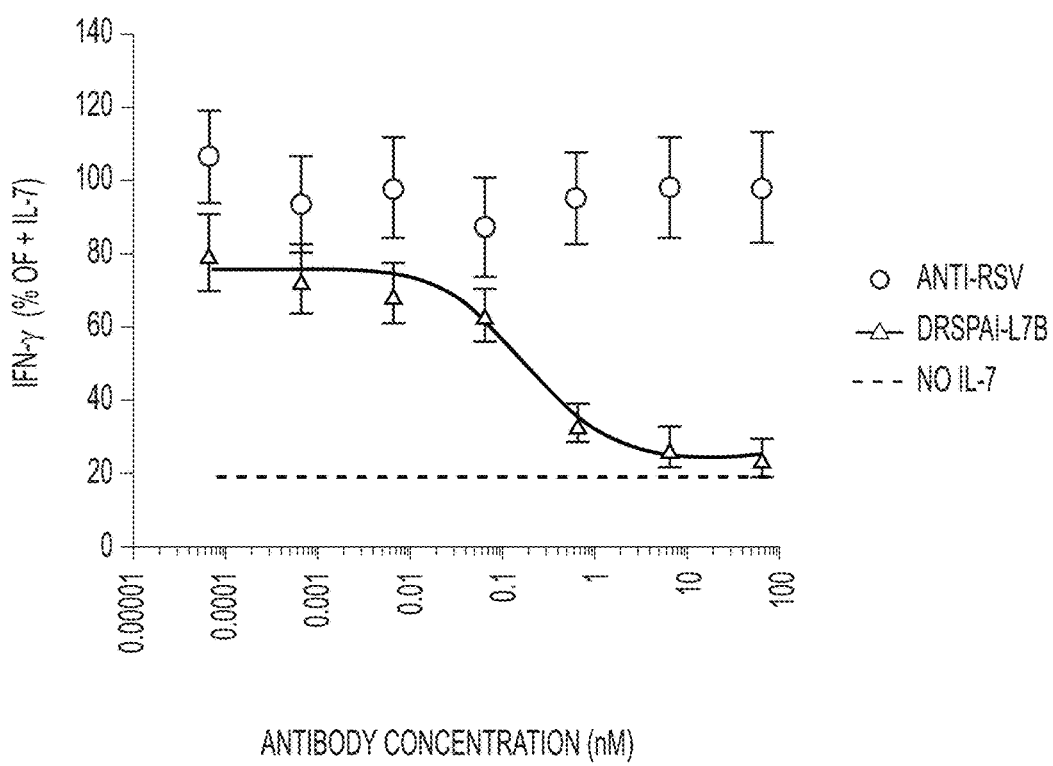
Figure 3B:
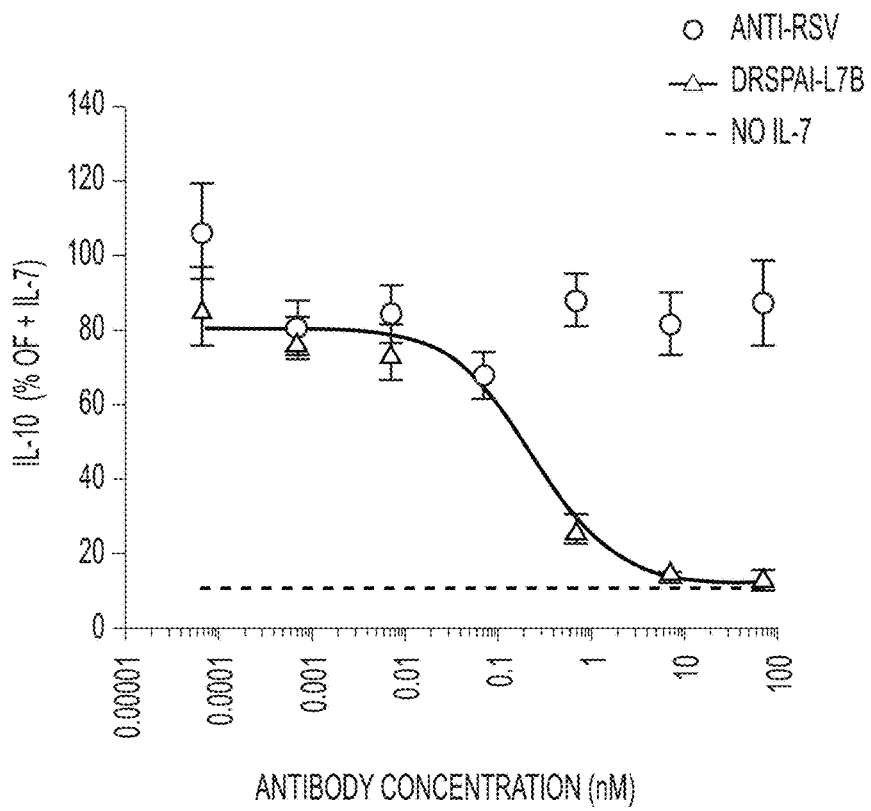
Figure 3C:
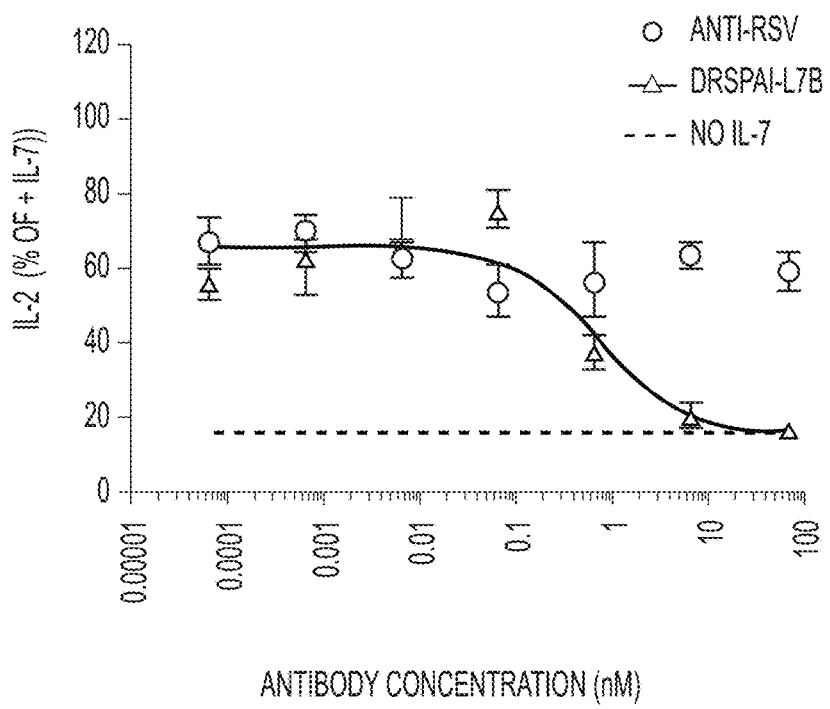
Figure 3D:
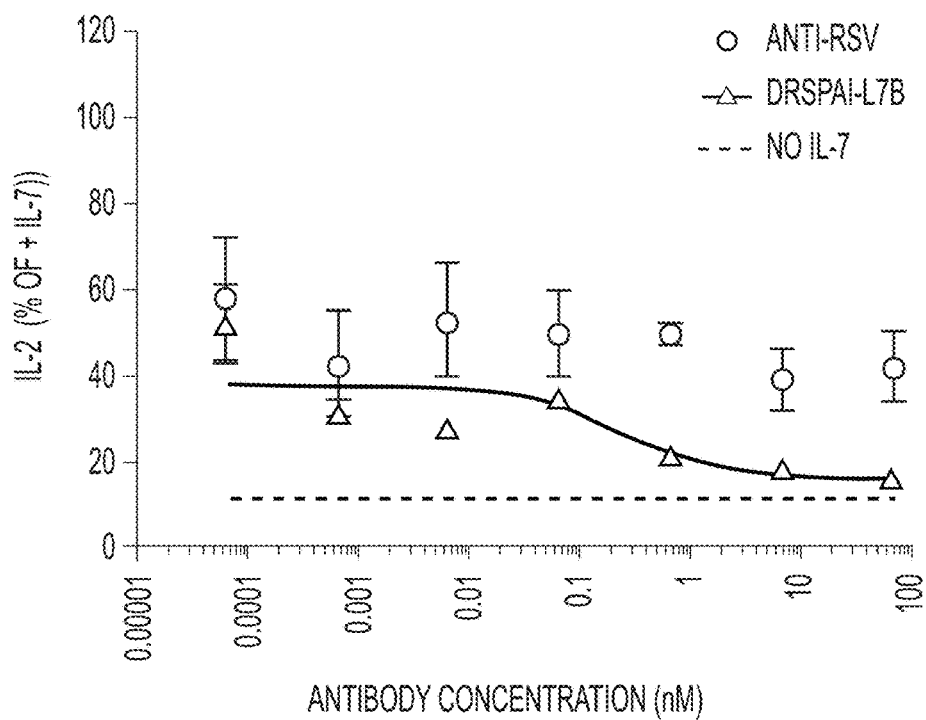
Figure 3E:
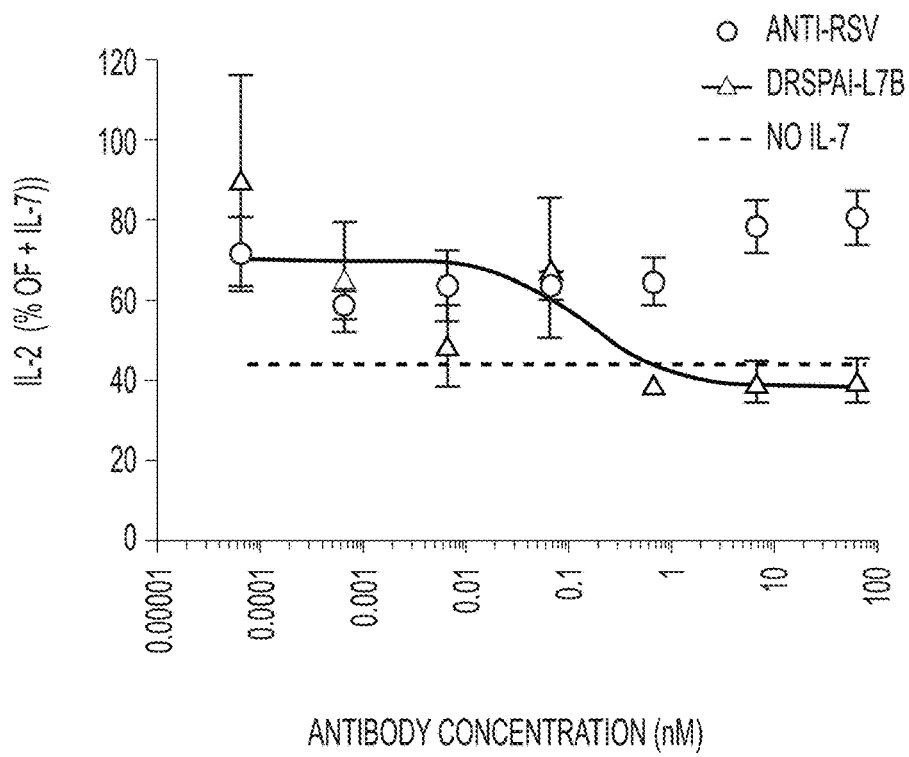
Figure 3F:
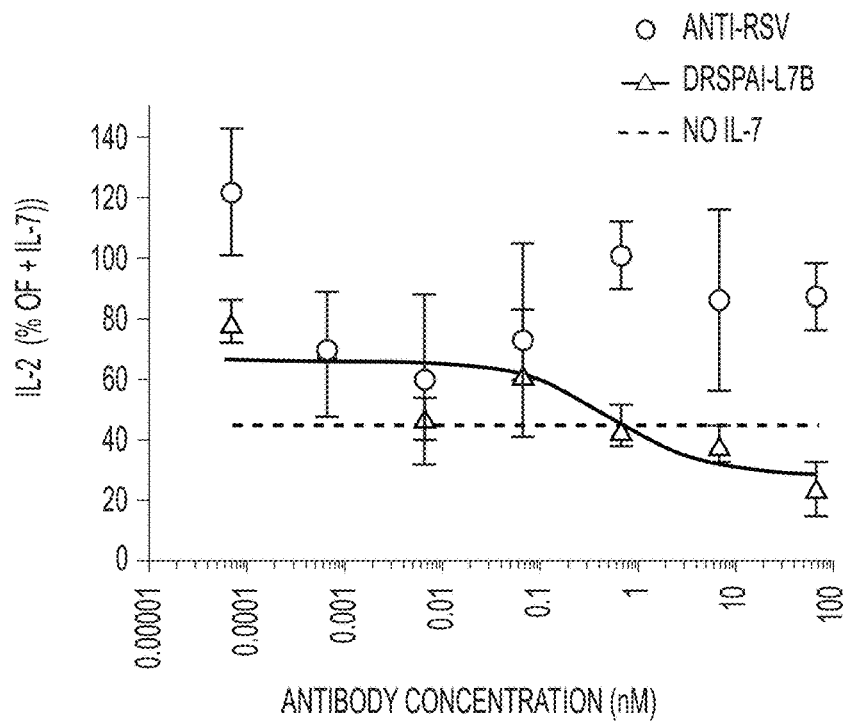
Figure 3G:
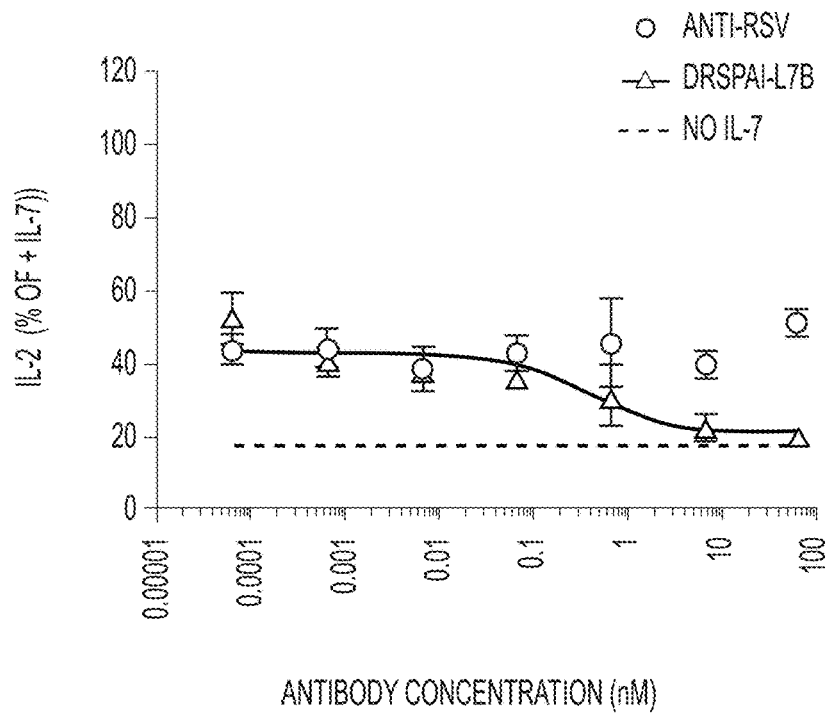

FIG. 3A: illustrates inhibition of IFN-γ secretion by healthy donor PBMCs treated with increasing concentrations of DRSPAI-L7B in the presence of rhIL-7 and anti-CD3. FIG. 3B illustrates inhibition of IL-10 secretion by healthy donor PBMCs treated with increasing concentrations of DRSPAI-L7B in the presence of rhIL-7 and anti-CD3. FIG. 3C, FIG. 3D, FIG. 3E, FIG. 3F, FIG. 3G illustrates inhibition of IL-2 by DRSPAI-L7B in the presence of rhIL-7 and anti-CD3.

Figure 4A:
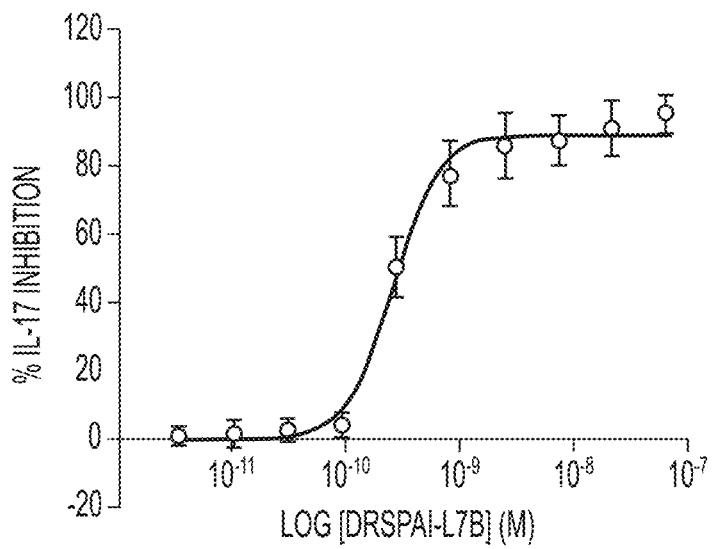
Figure 4B:
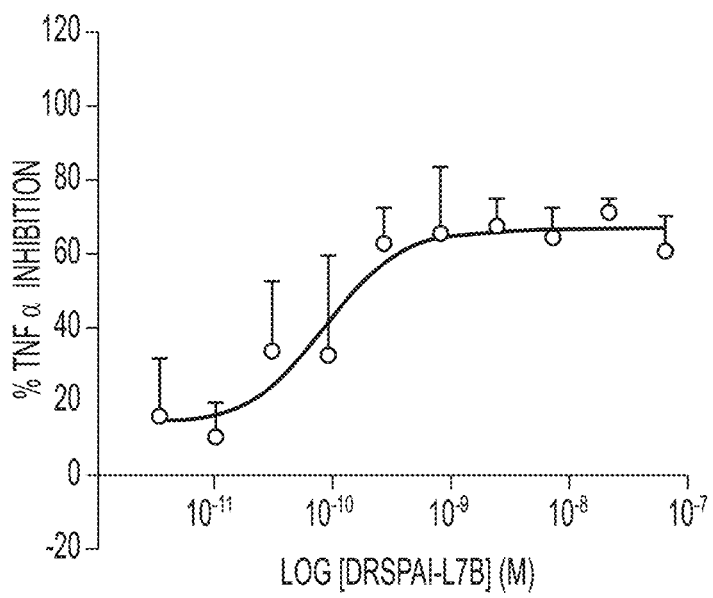
Figure 4C:
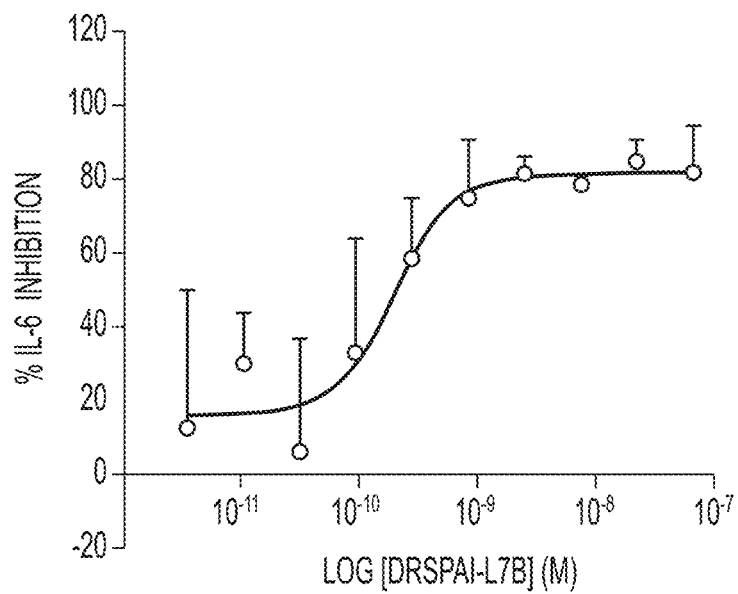
Figure 4D:
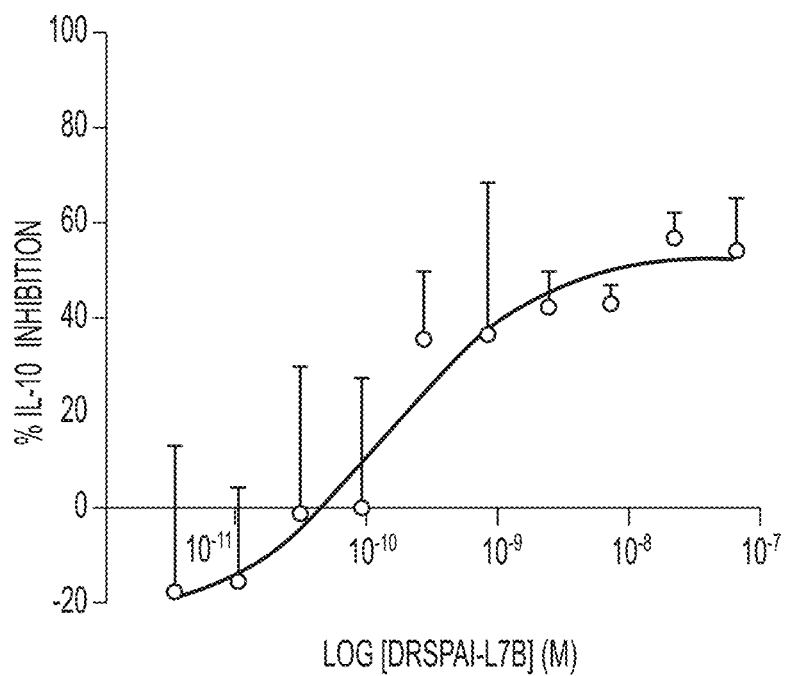
Figure 4E:
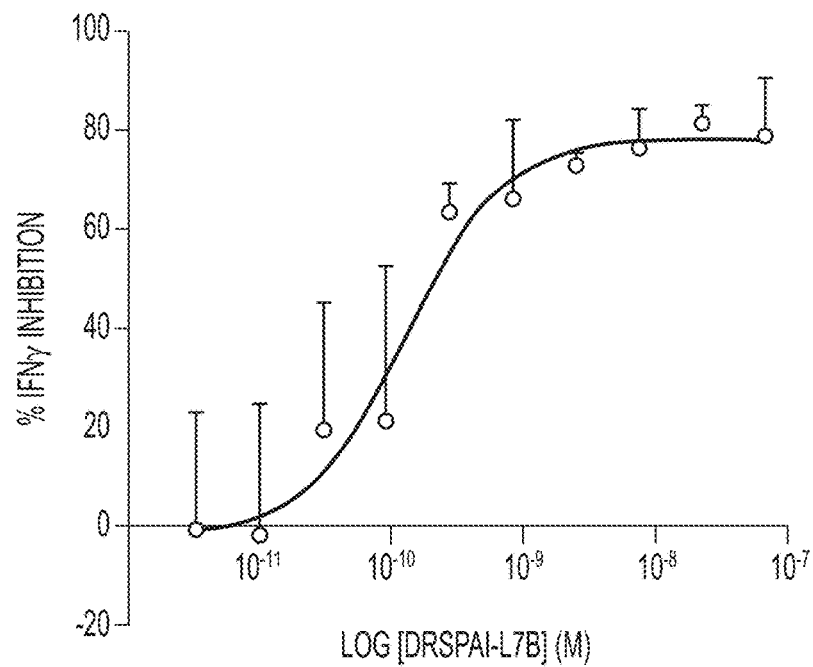
Figure 4F:
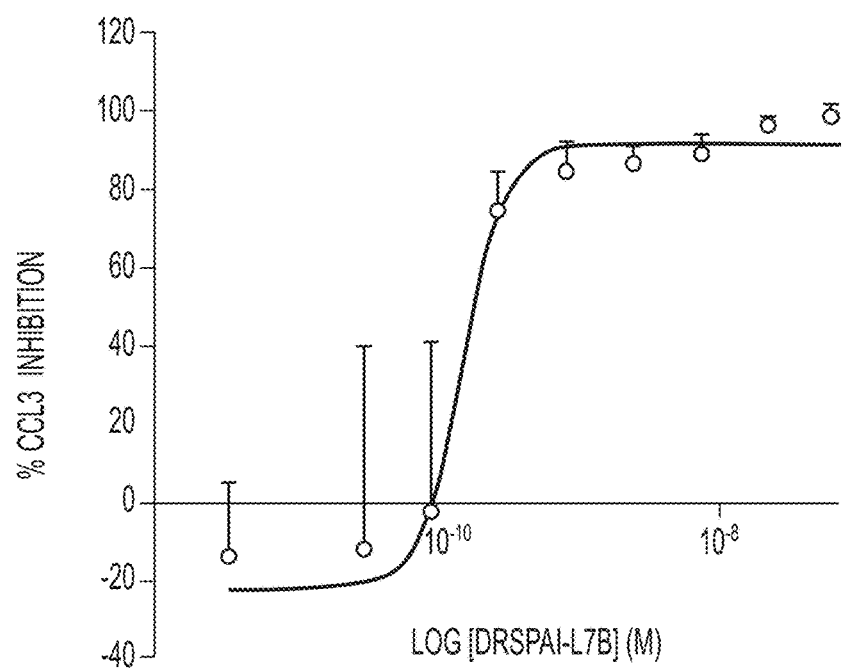

FIG. 4A: illustrates IL-17 inhibition in CD4$^+$ T$_{mem}$ cells that were isolated from healthy donor blood, incubated with IL-7 in the presence of DRSPAI-L7B after being spiked with phorbol myristate acetate (PMA)/ionomycin. FIG. 4B illustrates TNFα inhibition in CD4$^+$ T$_{mem}$ cells that were isolated from healthy donor blood, incubated with IL-7 in the presence of DRSPAI-L7B after being spiked with PMA/ionomycin. FIG. 4C: illustrates IL-6 inhibition in CD4+ $T_{mem}$ cells that were isolated from healthy donor blood, incubated with IL-7 in the presence of DRSPAI-L7B after being spiked with PMA/ionomycin. FIG. 4D: illustrates IL-10 inhibition in CD4+ $T_{mem}$ cells that were isolated from healthy donor blood, incubated with IL-7 in the presence of DRSPAI-L7B after being spiked with PMA/ionomycin. FIG. 4E: illustrates INFγ inhibition in CD4+ $T_{mem}$ cells that were isolated from healthy donor blood, incubated with IL-7 in the presence of DRSPAI-L7B after being spiked with PMA/ionomycin. FIG. 4F: illustrates CCL3 inhibition in CD4+ $T_{mem}$ cells that were isolated from healthy donor blood, incubated with IL-7 in the presence of DRSPAI-L7B after being spiked with PMA/Ionomycin.

Figure 5A:
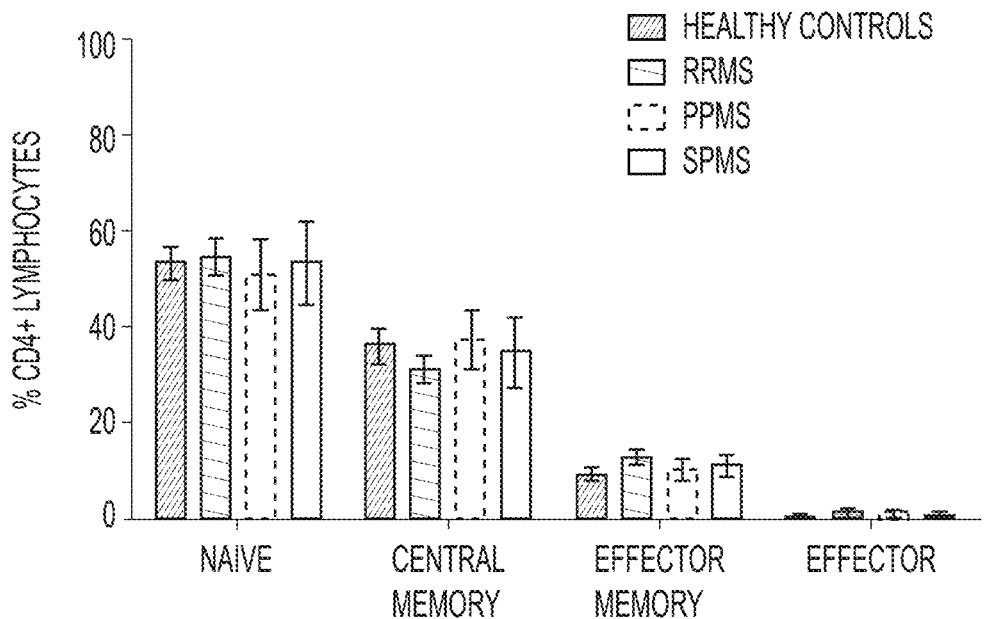
Figure 5B:
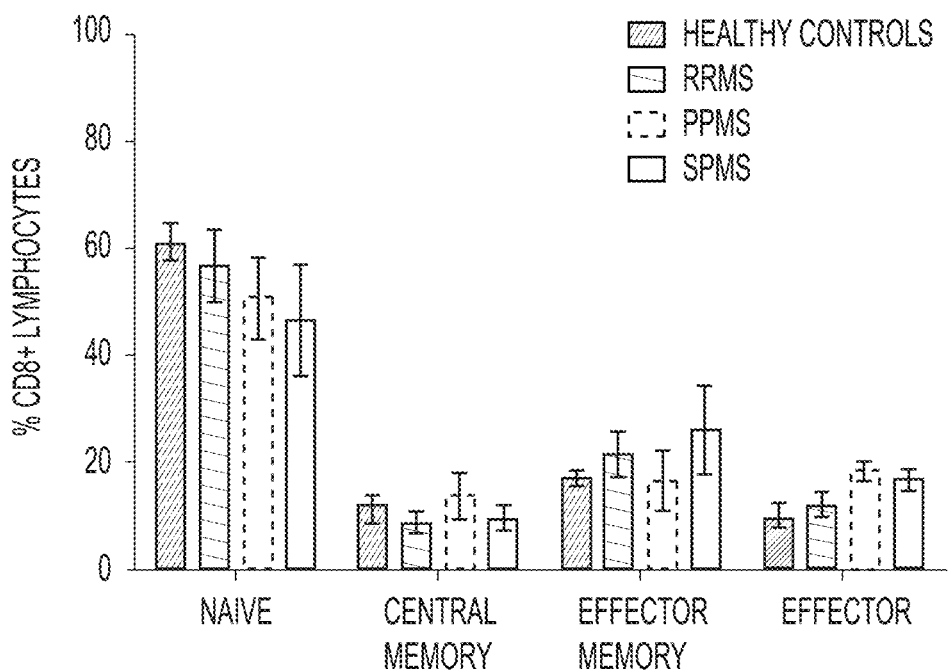
Figure 5C:
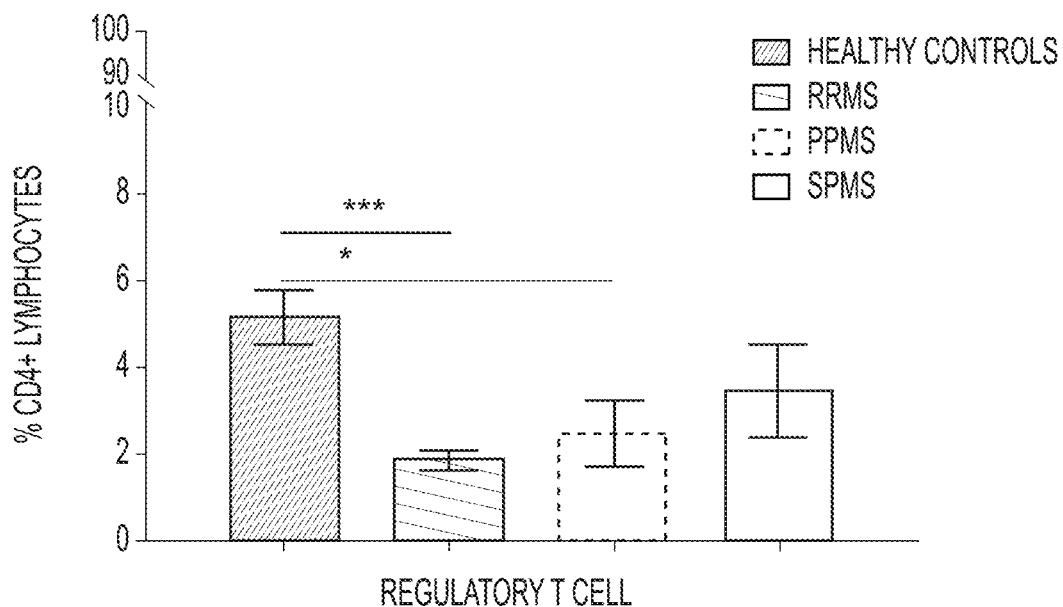

FIG. 5A: illustrates the profile of CD4+ lymphocytes from healthy controls and MS patients profiled by flow cytometry based on CD45RO, CCR7, CD127 and CD25 expression on the cell surface. FIG. 5B illustrates the profile of CD8+ lymphocytes from healthy controls and MS patients profiled by flow cytometry based on CD45RO, CCR7, CD127 and CD25 expression on the cell surface. FIG. 5C illustrates the profile of regulatory T cells from healthy controls and MS patients profiled by flow cytometry based on CD45RO, CCR7, CD127 and CD25 expression on the cell surface.

Figure 6A:
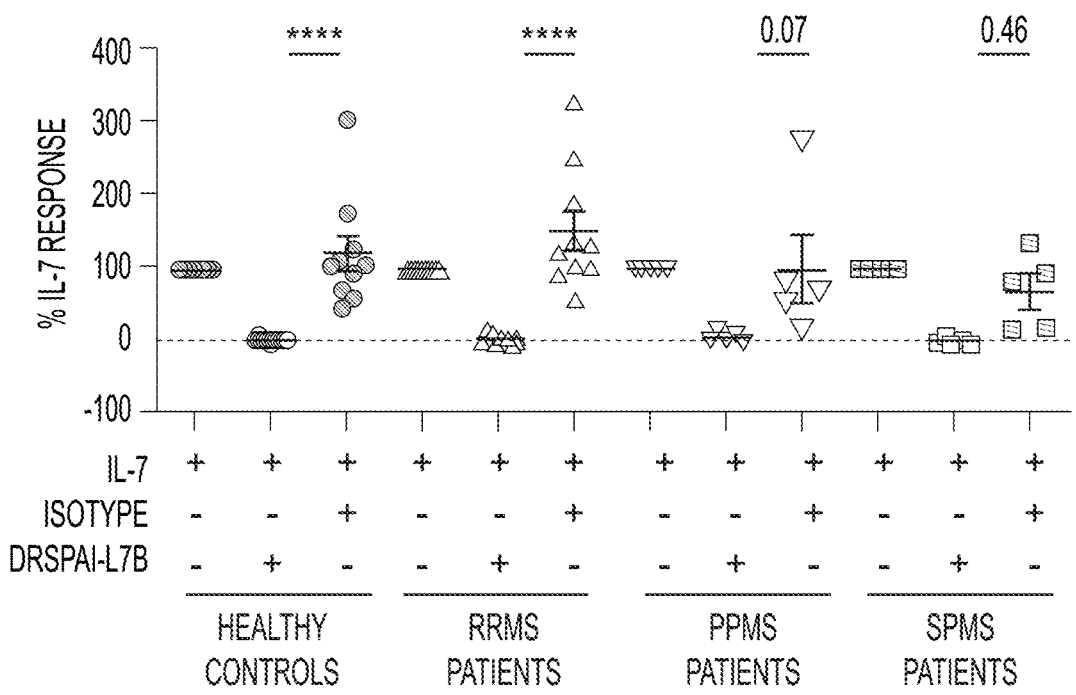
Figure 6B:
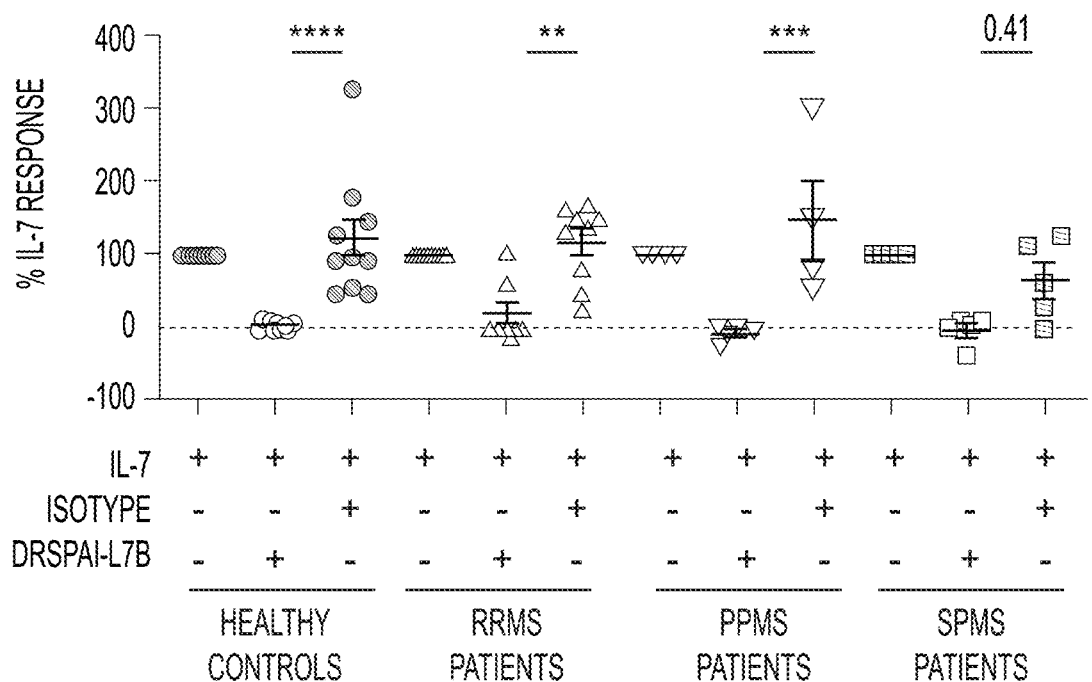

FIG. 6A: illustrates STAT5 phosphorylation in CD4+ T cells from PBMCs obtained from healthy donors or MS patients stimulated with rhIL-7 in the presence of DRSPAI-L7B or anti-RSV antibody (isotype control). FIG. 6B illustrates STAT5 phosphorylation in CD8+ T cells from PBMCs obtained from healthy donors or MS patients stimulated with rhIL-7 in the presence of DRSPAI-L7B or anti-RSV antibody (isotype control).

Figure 7A:
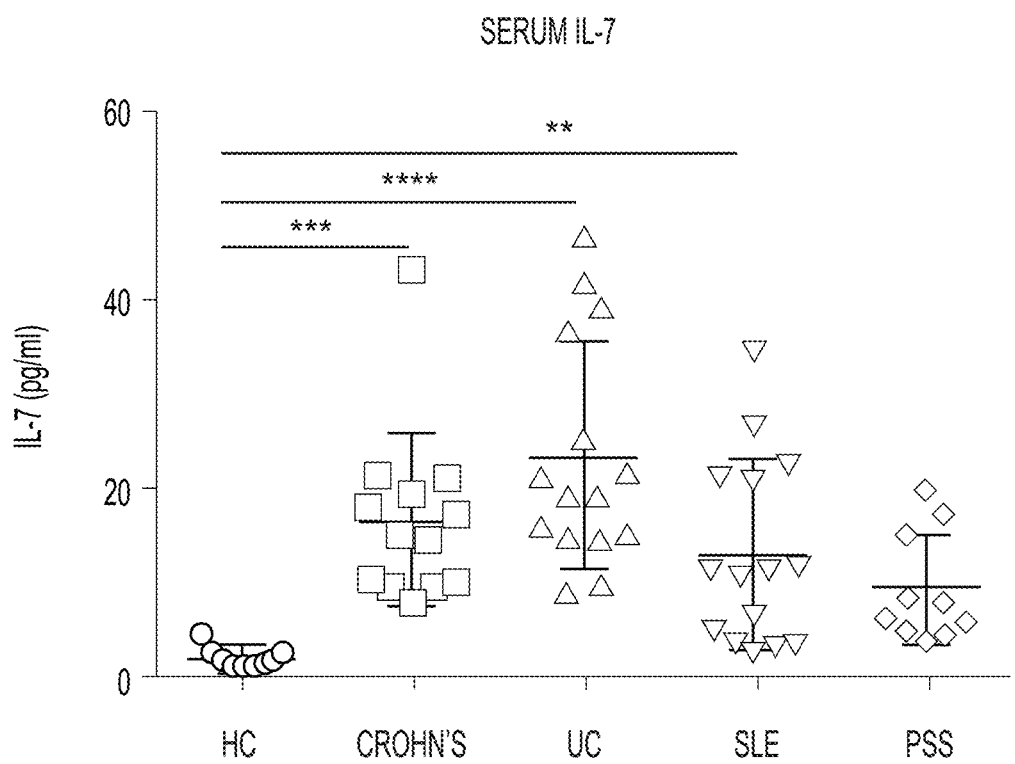
Figure 7B:
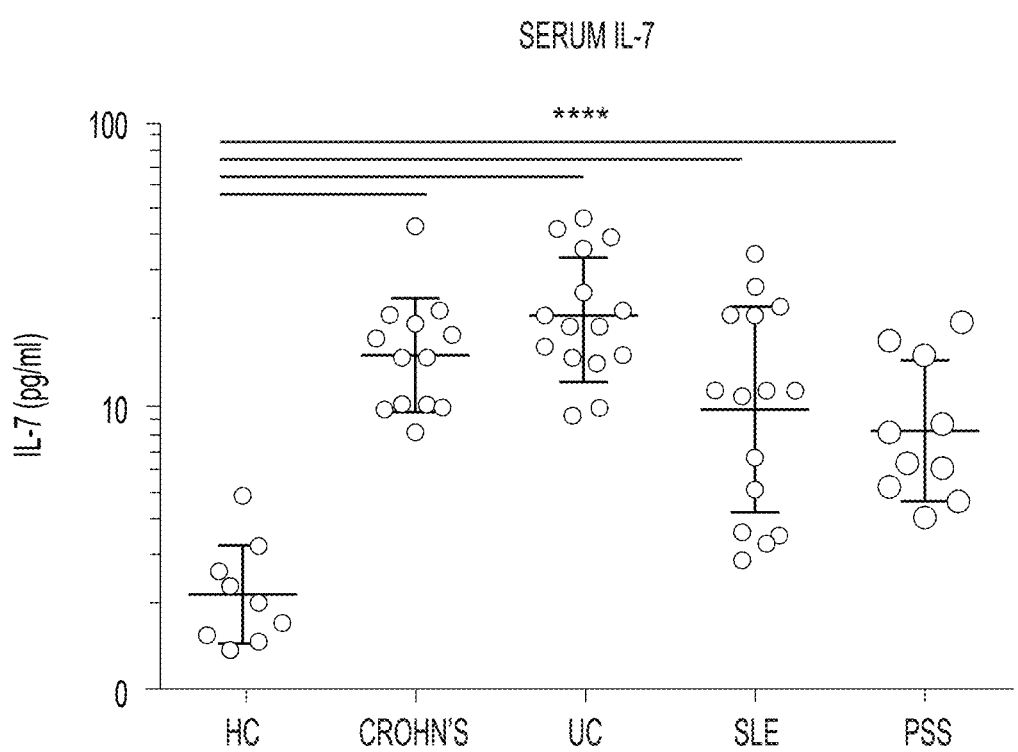

FIG. 7A: illustrates linear plot and FIG. 7B illustrates logarithmic plot of IL-7 levels in serum samples from healthy controls (HC, n=10), Crohn's disease (n=15), ulcerative colitis (UC, n=15), systemic lupus erythematosus (SLE, n=15) and primary Sjögren's syndrome (pSS, n=15) patients.

DETAILED DESCRIPTION OF THE DISCLOSURE

Inhibition of IL-7 receptor mediated signaling provides a promising therapeutic intervention for the treatment of autoimmune and/or inflammatory diseases. In some embodiments, disclosed herein are IL-7 binding proteins that reduces B cell activation, decreased autoantibody production and/or decreased B cell antigen presentation. In some embodiments, an IL-7 binding protein disclosed herein binds IL-7, inhibits IL-7 receptor mediated signaling and will not limit development or function of regulatory T cells ($T_{regs}$). In some embodiments, an IL-7 binding protein disclosed herein inhibits signaling, activation, cytokine production and proliferation of both CD4+ and CD8+ T cells. In some embodiments, the IL-7 binding protein blockade of IL-7 mediated signaling decreases an inflammatory response.

IL-7 Binding Protein

The term "IL-7 mediated signaling", as used herein, means the biological effect instigated by the IL-7 receptor complex when bound by its ligand, IL-7. IL-7 mediated signaling therefore includes, but is not necessarily limited to, one or more, or all, of IL-7 induced phosphorylation of STAT-5, IL-7 induced expansion of $T_H17$ cells and IL-7 induced survival of $T_H17$ cells.

The term "IL-7 binding protein" as used herein refers to antibodies and other protein constructs, such as domains, which are capable of binding to IL-7. The terms "IL-7 binding protein" and "anti-IL-7 antigen binding protein" are used interchangeably herein. This does not include the natural cognate receptor.

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanized, multispecific antibodies, including bispecific antibodies, and heteroconjugate antibodies; a single variable domain (e.g., a domain antibody (DAB)), antigen binding antibody fragments, Fab, F(ab')$_2$, Fv, disulphide linked Fv, single chain Fv, disulphide-linked scFv, diabodies, TAND-ABS, etc. and modified versions of any of the foregoing (for a summary of alternative "antibody" formats see Holliger and Hudson, *Nature Biotechnology,* 2005, Vol 23, No. 9, 1126-1136).

In some embodiments, an IL-7 binding protein disclosed herein may be derived from rat, mouse, primate (e.g. cynomolgus, Old World monkey or Great Ape) or human. The IL-7 binding protein may be a human, humanized or chimeric antibody. The IL-7 binding protein may comprise a constant region, which may be of any isotype or subclass. The constant region may be of the IgG isotype, for example IgG1, IgG2, IgG3, IgG4 or variants thereof. The IL-7 binding protein constant region may be IgG1. In some embodiment, the IL-7 binding protein is an IgG1k antibody.

As used herein, "about" means plus or minus 10%.

The term, "full", "whole" or "intact" antibody, used interchangeably herein, refers to a heterotetrameric glycoprotein. An intact antibody is composed of two identical heavy chains (HCs) and two identical light chains (LCs) linked by covalent disulphide bonds. This $H_2L_2$ structure folds to form three functional domains comprising two antigen-binding fragments, known as 'Fab' fragments, and a 'Fc' crystallisable fragment. The Fab fragment is composed of the variable domain at the amino-terminus, variable heavy ($V_H$) or variable light ($V_L$), and the constant domain at the carboxyl terminus, CH1 (heavy) and CL (light). The Fc fragment is composed of two domains formed by dimerization of paired CH2 and CH3 regions. The Fc may elicit effector functions by binding to receptors on immune cells or by binding C1q, the first component of the classical complement pathway. The five classes of antibodies IgM, IgA, IgG, IgE and IgD are defined by distinct heavy chain amino acid sequences, which are called μ, α, γ, ε and δ respectively, each heavy chain can pair with either a κ or λ light chain. The majority of antibodies in the serum belong to the IgG class, there are four isotypes of human IgG (IgG1, IgG2, IgG3 and IgG4), the sequences of which differ mainly in their hinge region. In some embodiments, an IL-7 binding protein disclosed herein is a human IgG1. In some embodiments, an IL-7 binding protein disclosed herein is a disulfide-linked α2β2 tetramer. In some embodiments, an IL-7 binding protein disclosed herein comprises two light (kappa) and two heavy (IgG1) chains.

Fully human antibodies can be obtained using a variety of methods, for example using yeast-based libraries or transgenic animals (e.g. mice) that can produce repertoires of human antibodies. Yeast presenting human antibodies on their surface that bind to an antigen of interest can be selected using FACS (Fluorescence-Activated Cell Sorting) based methods or by capture on beads using labelled antigens. Transgenic animals that have been modified to express human immunoglobulin genes can be immunized with an antigen of interest and antigen-specific human antibodies isolated using B-cell sorting techniques. Human antibodies produced using these techniques can then be characterized for desired properties such as affinity, developability and selectivity.

In some embodiments, alternative antibody formats can be used. Alternative antibody formats include alternative scaffolds in which the one or more CDRs of the IL-7 antibody can be arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain.

The term "domain" refers to a folded polypeptide structure which retains its tertiary structure independent of the rest of the polypeptide. Generally, domains are responsible for discrete functional properties of polypeptides and in many cases may be added, removed or transferred to other polypeptides without loss of function of the remainder of the protein and/or of the domain.

The term "single variable domain" refers to a folded polypeptide domain comprising sequences characteristic of antibody variable domains. It therefore includes complete antibody variable domains such as VH, VHH and VL and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain can bind an antigen or epitope independently of a different variable region or domain. A "domain antibody" or "DAB" may be considered the same as a "single variable domain". A single variable domain may be a human single variable domain, but also includes single variable domains from other species such as rodent (for example, as disclosed in WO 00/29004 A1), nurse shark and Camelid VHH DABs. Camelid VHH are immunoglobulin single variable domain polypeptides that are derived from species including camel, llama, alpaca, dromedary, and guanaco, which produce heavy chain antibodies naturally devoid of light chains. Such VHH domains may be humanized according to standard techniques available in the art, and such domains are considered to be "single variable domains". As used herein, VH includes camelid VHH domains.

An antigen binding fragment, IL-7 binding protein fragment, functional fragment, biologically active fragment or an immunologically effective fragment may comprise partial heavy or light chain variable sequences. Fragments are at least 5, 6, 8 or 10 amino acids in length. Alternatively, the fragments are at least 15, at least 20, at least 50, at least 75, or at least 100 amino acids in length.

An antigen binding fragment may be provided by means of arrangement of one or more CDRs on non-antibody protein scaffolds. "Protein Scaffold" as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions.

The protein scaffold may be an Ig scaffold, for example an IgG, or IgA scaffold. The IgG scaffold may comprise some or all the domains of an antibody (i.e. CH1, CH2, CH3, VH, VL). The IL-7 binding protein may comprise an IgG scaffold selected from IgG1, IgG2, IgG3, IgG4 or IgG4PE. For example, the scaffold may be IgG1. The scaffold may consist of, or comprise, the Fc region of an antibody, or is a part thereof.

The protein scaffold may be a derivative of a scaffold selected from the group consisting of CTLA-4, lipocalin, Protein A derived molecules such as Z-domain of Protein A (Affibody, SpA), A-domain (Avimer/Maxibody); heat shock proteins such as GroEI and GroES; transferrin (trans-body); ankyrin repeat protein (DARPin); peptide aptamer; C-type lectin domain (Tetranectin); human g-crystallin and human ubiquitin (affilins); PDZ domains; scorpion toxin kunitz type domains of human protease inhibitors; and fibronectin/adnectin; which has been subjected to protein engineering in order to obtain binding to an antigen other than the natural ligand.

The term "antagonist antibody" as used herein refers to an antibody or fragment thereof that is capable of fully or partially inhibiting the biological activity of the antigen, e.g. IL-7, to which it binds for example by fully or partially blocking binding to a ligand or reducing the biological activity of the antigen.

"Antigen binding site" refers to a site on an antigen binding protein which is capable of specifically binding to an antigen, this may be a single variable domain, or it may be paired $V_H/V_L$ domains as can be found on a standard antibody. Single-chain Fv (ScFv) domains can also provide antigen-binding sites.

The term "chimeric antigen receptor" ("CAR") as used herein, refers to an engineered receptor which consists of an extracellular antigen binding domain (which is usually derived from a monoclonal antibody, or fragment thereof, e.g. a VH domain and a VL domain in the form of a scFv), optionally a spacer region, a transmembrane region, and one or more intracellular effector domains. CARs have also been referred to as chimeric T cell receptors or chimeric immunoreceptors (CIRs). CARs are genetically introduced into hematopoietic cells, such as T cells, to redirect T cell specificity for a desired cell-surface antigen, resulting in a CAR-T therapeutic.

A "humanized antibody" refers to a type of engineered antibody having its CDRs derived from a non-human donor immunoglobulin, the remaining immunoglobulin-derived parts of the molecule being derived from one or more human immunoglobulin(s). In addition, framework support residues may be altered to preserve binding affinity (see, e.g. Queen et al. Proc. Natl Acad Sci USA, 86:10029-10032 (1989), Hodgson et al. *Bio/Technology*, 9:421 (1991)). A suitable human acceptor antibody may be one selected from a conventional database, e.g. the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

The prior art describes several ways of producing such humanized antibodies—see, for example, EP-A-0239400 and EP-A-054951.

The term "spacer region" as used herein, refers to an oligo- or polypeptide that functions to link the transmembrane domain to the target binding domain. This region may also be referred to as a "hinge region" or "stalk region". The size of the spacer can be varied depending on the position of the target epitope in order to maintain a set distance (e.g. 14 nm) upon CAR:target binding.

The term "transmembrane domain" as used herein refers to the part of the CAR molecule which traverses the cell membrane.

The term "intracellular effector domain" (also referred to as the "signaling domain") as used herein refers to the domain in the CAR which is responsible for intracellular signaling following the binding of the antigen binding domain to the target. The intracellular effector domain is responsible for the activation of at least one of the normal effector functions of the immune cell in which the CAR is expressed. For example, the effector function of a T cell can be a cytolytic activity or helper activity including the secretion of cytokines.

It will be appreciated by a person skilled in the art that VH and/or VL domains disclosed herein may be incorporated, e.g. in the form of a scFv, into CAR-T therapeutics.

In some embodiments, IL-7 binding proteins of the present disclosure show cross-reactivity between human IL-7 and IL-7 from another species, such as cynomolgus macaque IL-7. In an embodiment, the IL-7 binding proteins of the invention specifically bind human and macaque IL-7. This is particularly useful, since drug development typically requires testing of lead drug candidates in mouse systems before the drug is tested in humans. The provision of a drug that can bind human and macaque species allows one to test results in these systems and make side-by-side comparisons of data using the same drug. This avoids the complication of needing to find a drug that works against a macaque IL-7 and a separate drug that works against human IL-7, and also avoids the need to compare results in humans and macaque using non-identical drugs. Cross reactivity between other species used in disease models such as dog or mice is also envisaged.

Optionally, the binding affinity of the IL-7 binding protein for at least cynomolgus macaque IL-7 and the binding affinity for human IL-7 differ by no more than a factor of 2 or 5. In some embodiments, an IL-7 binding protein disclosed herein is species specific.

Affinity, also referred to as "binding affinity", is the strength of binding at a single interaction site, i.e. of one molecule, e.g. an IL-7 binding protein of the disclosure, to another molecule, e.g. its target antigen, at a single binding site. The binding affinity of an IL-7 binding protein to its target may be determined by equilibrium methods (e.g. enzyme-linked immunoabsorbent assay (ELISA) or radio-immunoassay (RIA)), or kinetics (e.g. surface plasmon resonance analysis using a BIACORE instrument). For example, the BIACORE method described in Example 2 may be used to measure binding affinity.

Avidity, also referred to as functional affinity, is the cumulative strength of binding at multiple interaction sites, e.g. the sum total of the strength of binding of two molecules (or more, e.g. in the case of a bispecific or multispecific molecule) to one another at multiple sites, e.g. taking into account the valency of the interaction.

In an embodiment, the equilibrium dissociation constant (KD) of the IL-7 binding protein-IL-7 interaction is about 100 nM or less, about 10 nM or less, about 2 nM or less or about 1 nM or less. Alternatively, the KD may be between about 5 and about 10 nM; or between about 1 and about 2 nM. The KD may be between about 1 pM and about 500 pM; or between about 500 pM and about 1 nM. In an embodiment, the equilibrium dissociation constant (KD) of the IL-7 binding protein-IL-7 interaction is 100 nM or less, 10 nM or less, 2 nM or less or 1 nM or less. Alternatively, the KD may be between 5 and 10 nM; or between 1 and 2 nM. The KD may be between 1 pM and 500 pM; or between 500 pM and 1 nM. A skilled person will appreciate that the smaller the KD numerical value, the stronger the binding. The reciprocal of KD (i.e. 1/KD) is the equilibrium association constant (KA) having units $M^{-1}$. A skilled person will appreciate that the larger the KA numerical value, the stronger the binding. In some embodiments, the KD of the IL-7 binding protein disclosed herein is about 30 to 90 pM. In some embodiments, the KD of the IL-7 binding protein disclosed herein is about 30 to about 80 pM, about 30 to about 70 pM, about 30 to about 60 pM, about 30 to about 50 pM, about 30 to about 55 pM or about 30 to about 40 pM. In some embodiments, the KD of the IL-7 binding protein disclosed herein is about 40 to about 80 pM, about 40 to about 70 pM, about 40 to about 60 pM, about 40 to about 50 pM, about 40 to about 55 pM. In some embodiments, the KD of the IL-7 binding protein disclosed herein is about 30 to about 55 pM. In some embodiments, the KD of the IL-7 binding protein disclosed herein is about 31, about 34, about 46, about 53, about 69, about 73, about 75 or about 87 pM. In some embodiments, the KD of the IL-7 binding protein disclosed herein is about 31, about 34, about 46, about 53, about 69, about 73, about 75 or about 87 pM. In some embodiments, the KD of the IL-7 binding protein disclosed herein is about 34 pM. In some embodiments, the KD of the IL-7 binding protein disclosed herein is about 67 pM. In some embodiments, the KD of the IL-7 binding protein disclosed herein is about 30 to about 55 pM at 25° C. In some embodiments, the KD of the IL-7 binding protein disclosed herein is about 36 pM at about 25° C. In some embodiments, the KD of the IL-7 binding protein disclosed herein is about 45 to about 90 pM. In some embodiments, the KD of the IL-7 binding protein disclosed herein is about 45 to about 90 pM at 37° C. In some embodiments, the KD of the IL-7 binding protein disclosed herein is about 67 pM at 37° C. In some embodiments, the KD of the IL-7 binding protein disclosed herein is 30 to 90 pM. In some embodiments, the KD of the IL-7 binding protein disclosed herein is 30 to 80 pM, 30 to 70 pM, 30 to 60 pM, 30 to 50 pM, 30 to 55 pM or 30 to 40 pM. In some embodiments, the KD of the IL-7 binding protein disclosed herein is 40 to 80 pM, 40 to 70 pM, 40 to 60 pM, 40 to 50 pM, 40 to 55 pM. In some embodiments, the KD of the IL-7 binding protein disclosed herein is 30 to 55 pM. In some embodiments, the KD of the IL-7 binding protein disclosed herein is 31, 34, 46, 53, 69, 73, 75 or 87 pM. In some embodiments, the KD of the IL-7 binding protein disclosed herein is 31, 34, 46, 69, 75 or 87 pM. In some embodiments, the KD of the IL-7 binding protein disclosed herein is 34 pM. In some embodiments, the KD of the IL-7 binding protein disclosed herein is 67 pM. In some embodiments, the KD of the IL-7 binding protein disclosed herein is 30 to 55 pM at 25° C. In some embodiments, the KD of the IL-7 binding protein disclosed herein is 36 pM at 25° C. In some embodiments, the KD of the IL-7 binding protein disclosed herein is 45 to 90 pM. In some embodiments, the KD of the IL-7 binding protein disclosed herein is 45 to 90 pM at 37° C. In some embodiments, the KD of the IL-7 binding protein disclosed herein is 67 pM at 37° C.

In some embodiments, the KD of the IL-7 binding protein disclosed herein is 31, 34, 46, 53, 69, 73, 75 or 87 pM, plus or minus 15%. In some embodiments, the KD of the IL-7 binding protein disclosed herein is 31, 34, 46, 69, 75 or 87 pM, plus or minus 15%. In some embodiments, the KD of the IL-7 binding protein disclosed herein is 34 pM plus or minus 15%. In some embodiments, the KD of the IL-7 binding protein disclosed herein is 67 pM plus or minus 15%. In some embodiments, the KD of the IL-7 binding protein disclosed herein is 30 to 55 pM at 25° C. In some embodiments, the KD of the IL-7 binding protein disclosed herein is 36 pM, plus or minus 15%, at 25° C. In some embodiments, the KD of the IL-7 binding protein disclosed herein is 45 to 90 pM. In some embodiments, the KD of the IL-7 binding protein disclosed herein is 45 to 90 pM at 37° C. In some embodiments, the KD of the IL-7 binding protein disclosed herein is 67 pM plus or minus 15% at 37° C.

A skilled person will appreciate that surface plasmon resonance (SPR) is a suitable method to measure binging affinity and also determine binding kinetics, see, e.g. Day et al., Direct comparison of binding equilibrium, thermodynamic, and rate constants determined by surface- and solution-based biophysical methods, Protein Science (2002), 11:1017-1025; and, Hearty et al, "Measuring antibody-antigen binding kinetics using surface plasmon resonance" Methods Mol Biol (2012) 907:411-4.

The dissociation rate constant (kd) or "off-rate" describes the stability of the IL-7 binding protein-IL-7 complex, i.e. the fraction of complexes that decay per second. For example, a kd of 0.01 $s^{-1}$ equates to 1% of the complexes decaying per second. In an embodiment, the dissociation rate constant (kd) is about $1 \times 10^{-3}$ $s^{-1}$ or less, about $1 \times 10^{-4}$ $s^{-1}$ or less, about $1 \times 10^{-5}$ $s^{-1}$ or less, or about $1 \times 10^{-6}$ $s^{-1}$ or less. The kd may be between about $1 \times 10^{-5}$ $s^{-1}$ and about $1 \times 10^{-4}$ $s^{-1}$; or between about $1 \times 10^{-4}$ $s^{-1}$ and about $1 \times 10^{-3}$ $s^{-1}$. In some embodiments, the kd of an IL-7 binding protein disclosed herein is about $2.06 \times 10^{-4}$ $s^{-1}$ or less, about $1.58 \times 10^{-4}$ $s^{-1}$ or less, about $1.7 \times 10^{-4}$ $s^{-1}$ or less, or about $5.68 \times 10^{-4}$ $s^{-1}$ or less, about $6.78 \times 10^{-4}$ $s^{-1}$ or less, about $8.26 \times 10^{-4}$ $s^{-1}$ or less, about $5.15 \times 10^{-4}$ $s^{-1}$ or less. In some embodiments, the kd of an IL-7 binding protein disclosed herein is about $1.58 \times 10^{-4}$ $s^{-1}$ or less. In some embodiments, the kd of an IL-7 binding protein disclosed herein is about $5.68 \times 10^{-4}$ $s^{-1}$ or less. In some embodiments, the kd of an IL-7 binding protein disclosed herein is about $2.06 \times 10^{-4}$ $s^{-1}$ or less, about $1.58 \times 10^{-4}$ $s^{-1}$ or less, or about $1.7 \times 10^{-4}$ $s^{-1}$ or less at 25° C. In some embodiments, the kd of an IL-7 binding protein disclosed herein is about $5.68 \times 10^{-4}$ $s^{-1}$ or less, about $6.78 \times 10^{-4}$ $s^{-1}$ or less, about $8.26 \times 10^{-4}$ $s^{-1}$ or less, or about $5.15 \times 10^{-4}$ $s^{-1}$ or less at 37° C.

In an embodiment, the dissociation rate constant (kd) is $1 \times 10^{-3}$ $s^{-1}$ or less, $1 \times 10^{-4}$ $s^{-1}$ or less, $1 \times 10^{-5}$ $s^{-1}$ or less, or $1 \times 10^{-6}$ $s^{-1}$ or less. The kd may be between $1 \times 10^{-5}$ $s^{-1}$ and $1 \times 10^{-4}$ $s^{-1}$; or between $1 \times 10^{-4}$ $s^{-1}$ and $1 \times 10^{-3}$ $s^{-1}$. In some embodiments, the kd of an IL-7 binding protein disclosed herein is $2.06 \times 10^{-4}$ $s^{-1}$ or less, $1.58 \times 10^{-4}$ $s^{-1}$ or less, $1.7 \times 10^{-4}$ $s^4$ or less, or $5.68 \times 10^{-4}$ $s^{-1}$ or less, $6.78 \times 10^{-4}$ $s^{-1}$ or less, $8.26 \times 10^{-4}$ $s^{-1}$ or less, or $5.15 \times 10^{-4}$ $s^{-1}$ or less. In some embodiments, the kd of an IL-7 binding protein disclosed herein is $1.58 \times 10^{-4}$ $s^{-1}$ or less. In some embodiments, the kd of an IL-7 binding protein disclosed herein is $5.68 \times 10^{-4}$ $s^{-1}$ or less. In some embodiments, the kd of an IL-7 binding protein disclosed herein is $2.06 \times 10^{-4}$ $s^{-1}$ or less, $1.58 \times 10^{-4}$ $s^{-1}$ or less, or $1.7 \times 10^{-4}$ $s^{-1}$ or less at 25° C. In some embodiments, the kd of an IL-7 binding protein disclosed herein is $5.68 \times 10^{-4}$ $s^{-1}$ or less, $6.78 \times 10^{-4}$ $s^{-1}$ or less, $8.26 \times 10^{-4}$ $s^{-1}$ or less, or $5.15 \times 10^{-4}$ $s^{-1}$ or less at 37° C.

The association rate constant (ka) or "on-rate" describes the rate of IL-7 binding protein-IL-7 complex formation. In an embodiment, the association rate constant (ka) is about $6.49 \times 10^6$ $M^{-1}s^{-1}$, about $4.65 \times 10^6$ $M^{-1}$ $s^{-1}$, about $3.17 \times 10^6$ $M^{-1}$ $s^{-1}$, about $8.28 \times 10^6$ $M^{-1}s^{-1}$, about $1.47 \times 10^7$ $M^{-1}s^{-1}$, about $1.10 \times 10^7$ $M^{-1}s^{-1}$, or about $5.90 \times 10^6$ $M^{-1}s^{-1}$. In an embodiment, the association rate constant (ka) is about $6.49 \times 10^6$ $M^{-1}s^{-1}$, $4.65 \times 10^6$ $M^{-1}s^{-1}$ or about $3.17 \times 10^6$ $M^{-1}s^{-1}$ at 25° C. In an embodiment, the association rate constant (ka) is about $8.28 \times 10^6$ $M^{-1}s^{-1}$, about $1.47 \times 10^7$ $M^{-1}s^{-1}$, about $1.10 \times 10^7$ $M^{-1}s^{-1}$, or about $5.90 \times 10^6$ $M^{-1}s^{-1}$ at 37° C. In an embodiment, the association rate constant (ka) is $6.49 \times 10^6$ $M^{-1}s^{-1}$, $4.65 \times 10^6$ $M'$s$^{-1}$, $3.17 \times 10^6$ $M^{-1}$ $s^{-1}$, $8.28 \times 10^6 M^{-1}s^{-1}$, $1.47 \times 10^7 M^{-1}$ $s^{-1}$, $1.10 \times 10^7 M^{-1}s^{-1}$, or $5.90 \times 10^6 M's^{-1}$. In an embodiment, the association rate constant (ka) is $6.49 \times 10^6$ $M^{-1}s^{-1}$, $4.65 \times 10^6$ $M^{-1}s^{-1}$ or $3.17 \times 10^6$ $M^{-1}$ $s^{-1}$ at 25° C. In an embodiment, the association rate constant (ka) is $8.28 \times 10^6$ $M^{-1}$ $s^{-1}$, $1.47 \times 10^7$ $M^{-1}s$, $1.10 \times 10^7$ $M^{-1}$ $s^{-1}$, or $5.90 \times 10^6$ $M^{-1}s^{-1}$ at 37° C.

The term "neutralizes" as used throughout the present specification means that the biological activity of IL-7 is reduced in the presence of an IL-7 binding protein as described herein in comparison to the activity of IL-7 in the absence of the IL-7 binding protein, in vitro or in vivo. Neutralization may be due to one or more of blocking IL-7 binding to its receptor, preventing IL-7 from activating its receptor, down regulating IL-7 or its receptor, or affecting effector functionality.

The reduction or inhibition in biological activity may be partial or total. A neutralizing IL-7 binding protein may neutralize the activity of IL-7 by lowering the threshold for B cell activation by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to IL-7 activity in the absence of the IL-7 binding protein. Neutralization may be determined or measured using one or more assays known to the skilled person or as described herein. For example, FIGS. 2B, 2C, and 2D.

It will be apparent to those skilled in the art that the term "derived" is intended to define not only the source in the sense of it being the physical origin for the material but also to define material which is structurally identical to the material but which does not originate from the reference source.

By "isolated" it is intended that the molecule, such as an IL-7 binding protein, is removed from the environment in which it may be found in nature. For example, the molecule may be purified away from substances with which it would normally exist in nature. For example, the IL-7 binding protein can be purified to at least 95%, 96%, 97%, 98% or 99%, or greater with respect to a culture media containing the IL-7 binding protein. The IL-7 binding proteins and antibodies disclosed herein may be isolated IL-7 binding proteins and antibodies.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and variable domain regions within full-length antigen binding sequences, e.g. within an antibody heavy chain sequence or antibody light chain sequence, are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

Variants

It will be apparent to those skilled in the art that there are alternative numbering conventions for amino acid residues in variable domain sequences and full-length antibody sequences. There are also alternative numbering conventions for CDR sequences, for example those set out in Chothia et al. (1989) Nature 342: 877-883. The structure and protein folding of the IL-7 binding protein may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1

|    | Kabat CDR | Chothia CDR | AbM CDR | Contact CDR | Minimum Binding Unit |
|----|-----------|-------------|---------|-------------|----------------------|
| H1 | 31-35/ 35A/35B | 26-32/ 33/34 | 26-35/ 35A/35B | 30-35/ 35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

Accordingly, an IL-7 binding protein is provided, which comprises any one or a combination of the following CDRs: CDRH1 of SEQ ID NO: 6, CDRH2 of SEQ ID NO: 7, CDRH3 of SEQ ID NO: 8, CDRL1 of SEQ ID NO: 9, CDRL2 of SEQ ID NO: 10, CDRL3 of SEQ ID NO: 11. CDRs may be modified by at least one amino acid substitution, deletion or addition, wherein the variant IL-7 binding protein substantially retains the biological characteristics of the unmodified protein, such as binding to IL-7.

It will be appreciated that each of CDR H1, H2, H3, L1, L2, L3 may be modified alone or in combination with any other CDR, in any permutation or combination. In one embodiment, a CDR is modified by the substitution, deletion or addition of up to 3 amino acids, for example 1 or 2 amino acids, for example 1 amino acid. Typically, the modification is a substitution, particularly a conservative substitution, for example as shown in Table 2 below.

TABLE 2

| Side chain | Members |
|------------|---------|
| Hydrophobic | Met, Ala, Val, Leu, Ile |
| Neutral hydrophilic | Cys, Ser, Thr |
| Acidic | Asp, Glu |

TABLE 2-continued

| Side chain | Members |
|------------|---------|
| Basic | Asn, Gln, His, Lys, Arg |
| Residues that influence chain orientation | Gly, Pro |
| Aromatic | Trp, Tyr, Phe |

For example, in a variant CDR, the flanking residues that comprise the CDR as part of alternative definition(s) e.g. Kabat or Chothia, may be substituted with a conservative amino acid residue. In some embodiments, IL-7 binding proteins comprising variant CDRs as described above may be referred to herein as "functional CDR variants".

Accordingly, in another embodiment, IL-7 binding proteins provided herein are IL-7 binding proteins which binds to IL-7 and comprises CDRH3 of SEQ ID NO:8 or a variant CDRH3 thereof. In an embodiment, the IL-7 binding protein comprises CDRH1 of SEQ ID NO:6 or a variant CDRH1 thereof, CDRH2 of SEQ ID NO:7 or a variant CDRH2 thereof, CDRH3 of SEQ ID NO:8 or a variant CDRH3 thereof, CDRL1 of SEQ ID NO:9 or a variant CDRL1 thereof, CDRL2 of SEQ ID NO:10 or a variant CDRL2 thereof, and CDRL3 of SEQ ID NO:11 or a variant CDRL3 thereof. In some embodiments, IL-7 binding proteins disclosed herein, including those with one or more variant CDRs, may bind to IL-7 and may also neutralize IL-7 activity.

Disclosed herein are IL-7 binding proteins which binds to IL-7 and comprises a heavy chain variable region of SEQ ID NO:4. The IL-7 binding protein may comprise a light chain variable region of SEQ ID NO:5. In some embodiments, the IL-7 binding protein binds to and neutralizes IL-7. In one embodiment, the IL-7 binding protein comprises a heavy chain variable region of SEQ ID NO:4 and a light chain variable region of SEQ ID NO:5.

The CDRs L1, L2, L3, H1, H2 and H3 tend to structurally exhibit one of a finite number of main chain conformations (canonicals). The particular canonical structure class of a CDR is defined by both the length of the CDR and by the loop packing, determined by residues located at key positions in both the CDRs and the framework regions (structurally determining residues or SDRs). Martin and Thornton (1996; J Mol Biol 263:800-815) have generated an automatic method to define the "key residue" canonical templates. Cluster analysis is used to define the canonical classes for sets of CDRs, and canonical templates are then identified by analyzing buried hydrophobics, hydrogen-bonding residues, and conserved glycines and prolines. The CDRs of antibody sequences can be assigned to canonical classes by comparing the sequences to the key residue templates and scoring each template using identity or similarity matrices.

Based on the canonical class of the DRSPAI-L7B antibody, functional antibody binding could be predicted to be maintained in the presence of the following CDR substitutions, where the amino acid before the Kabat number is the original amino acid sequence of and the amino acid sequence at the end of the Kabat number is the substituted amino acid:

CDRL1 canonicals:
K24R

S27aN, S27aD, S27aT, S27aE, S31,N, S31T, S31K, S31G

L27bV

D27cL, D27cY, D27cV, D27cl, D27cS, D27cN, D27sF, D27cH, D27cG, D27cT

Y32F, Y32N, Y32A, Y32H, Y32S, Y32R 133M, 133L, 133V, 133R
N34H
CDRL2 canonicals:
G51A
CDRL3 canonicals:
Q89S, Q89G, Q89F, Q89L, Q90N, Q90H
S91N, S91F, 591G, S91R, S91D, S91H, S91T, S91Y, S91V
N92Y, N92 W, N92T, N92S, N92R, N92Q, N92Q, N92H, N92A, N92D
V93E, V93N, V93G, V93H, V93T, V93S, V93R, V93A
D94Y, D94T, D94V, D94L, D94H, D94N, D941, D94 W, D94P, D94S
L96P, L96Y, L96R, L961, L96 W, L96F
CDRH1 canonicals:
Y321, Y32H, Y32F, Y32T, Y32N, Y32C, Y32E, Y32D
G33Y, G33A, G33 W, G33T, G33L, G33V
V34M, V341, V34L, V34T, V34 W
H35E, H35N, H35Q, H35S, H35Y, H35T
CDRH2 canonicals:
151L, 151V, 151T, 151S, i51N, 151M
G55D
Y59L
CDRH3 canonicals:
Y102H, Y102V, Y1021, Y102S, Y102D,Y102G As discussed above, the particular canonical structure class of a CDR is defined by both the length of the CDR and by the loop packing, determined by residues located at key positions in both the CDRs and the framework regions. Thus, substitutions may also be made in the framework residues of an IL-7 binding protein of the invention, based on the canonical class, while retaining a functional antibody. Such substitutions may include (using Kabat numbering):

Light chain: I, L or V at position 2; Q, L or E at position 3; M or L at position 4; I or V at position 48; and/or Heavy chain: V, I or L at position 2; L or V at position 4; L, I, M or V at position 20; T, A, V, G or S at position 24; F, Y, T or G at position 27; F, L, I, V or S at position 29; W or Y at position 47; I, M, L, or V at position 48; I, L, F, M or V at position 69; R, K, V or I at position 71, A, L, V, Y or F at position 78; L or M at position 80, Y or F at position 90, R, K, G, S, H, N, T, A and/or L at position 94.

Thus, the IL-7 binding protein may have any of the above substitutions within the stated positions. There may be multiple substitutions per variant CDR, per heavy or light chain variable region, per heavy or light chain, and per IL-7 binding protein, and therefore any combination of substitution may be present in the IL-7 binding protein of the invention, provided that the canonical structure of the CDR is maintained. For the avoidance of doubt, the above-described substitutions should not be construed as limiting the possible CDR substitutions which may be performed whilst still retaining a functional anti-IL-7 antibody.

The VH or VL (or HC or LC) sequence disclosed herein may be a variant sequence with up to 10 amino acid substitutions, additions or deletions. For example, the variant sequence may have up to 9, 8, 7, 6, 5, 4, 3, 2 or 1 amino acid substitution(s), addition(s) or deletion(s). The sequence variation may exclude one or more or all of the CDRs, for example the CDRs are the same as the VH or VL (or HC or LC) sequence and the variation is in the remaining portion of the VH or VL (or HC or LC) sequence, so that the CDR sequences are fixed and intact.

Alternatively, the heavy chain variable region may have 75% or greater, 80% or greater, 85% or greater, 90% or greater, 95% or greater, 98% or greater, 99% or greater or 100% identity to the amino acid sequence set forth in SEQ ID NO:4; and the light chain variable region may have 75% or greater, 80% or greater, 85% or greater, 90% or greater, 95% or greater, 98% or greater, 99% or greater, or 100% identity to the amino acid sequence set forth in SEQ ID NO:5.

The heavy chain variable region may be a variant of the amino acid sequence set forth in SEQ ID NO:4 which may contain 30, 25, 20, 15, 10, 9, 8, 7, 6, 5, 4, 3, 2 or 1 amino acid substitutions, insertions or deletions. The light chain variable region may be a variant of the amino acid sequence set forth in SEQ ID NO:5 which may contain 30, 25, 20, 15, 10, 9, 8, 7, 6, 5, 4, 3, 2 or 1 amino acid substitutions, insertions or deletions.

In a particular embodiment, the IL-7 binding protein described herein binds to IL-7 and comprises a heavy chain and light chain variable domain combination of (SEQ ID NO:4) and (SEQ ID NO:5), or an IL-7 binding protein which has a heavy and light chain variable domains having at least about 75%, 80%, 85%, 90%, 95%, 96%, 97%, 98% or 99% identity to SEQ ID NO:4 and SEQ ID NO:5, respectively. In an embodiment, the IL-7 binding protein binds to and neutralizes IL-7.

Any of the heavy chain variable regions of the IL-7 binding protein described herein may be combined with a suitable constant region. Any of the light chain variable regions of the IL-7 binding protein may be combined with a suitable constant region. A constant region disclosed herein can be a human constant region.

The present disclosure also provides a nucleic acid molecule which encodes the polypeptide sequence(s) of any one of the IL-7 binding proteins described herein. The nucleic acid molecule may comprise a sequence encoding (i) one or more CDRHs, the heavy chain variable sequence, or the full length heavy chain sequence; and (ii) one or more CDRLs, the light chain variable sequence, or the full length light chain sequence, with (i) and (ii) on the same nucleic acid molecule. Alternatively, the nucleic acid molecule which encodes an IL-7 binding protein described herein may comprise sequences encoding (a) one or more CDRHs, the heavy chain variable sequence, or the full length heavy chain sequence; or (b) one or more CDRLs, the light chain variable sequence, or the full length light chain sequence, with (a) and (b) on separate nucleic acid molecules. In some embodiments, the nucleic acid comprises a sequence having at least about 80%, 90%, 95%, 96%, 97%, 98%, 99%, or 100% identity to the nucleic acid sequence set out in SEQ ID NO:13 encoding the light chain. In some embodiments, the nucleic acid comprises the nucleic acid sequence set out in SEQ ID NO:13 encoding the light chain. In some embodiments, the nucleic acid comprises a sequence having at least about 80%, 90%, 95%, 96%, 97%, 98%, 99%, or 100% identity to the nucleic acid sequence set out in SEQ ID NO:14 encoding the heavy chain. In some embodiments, the nucleic acid comprises the nucleic acid sequence set out in SEQ ID NO:14 encoding the heavy chain. In some embodiments, the nucleic acid further comprises a sequence having at least about 80%, 90%, 95%, 96%, 97%, 98%, 99%, or 100% identity to the nucleic acid sequence set out in SEQ ID NO:15 encoding a signal peptide.

IL-7 binding proteins as described above, for example variants with a partial alteration of the sequence by chemical modification and/or insertion, deletion or substitution of one or more amino acid residues, or those with 75% or greater, 80% or greater, 85% or greater, 90% or greater, 95% or greater, 98% or greater, or 99% or greater identity to any of the sequences described above, may display a potency for binding to IL-7, as demonstrated by EC50 or surface plasmon resonance analysis, of within 10 fold, or within 5 fold of the potency demonstrated by DRSPAI-L7B. DRSPAI-L7B is a human IgG1 that potently (Kd 67 pM) inhibits IL-7 mediated signalling by binding to interleukin 7 (IL-7). DRSPAI-L7B is a disulfide-linked $\alpha2\beta2$ tetramer consisting of two light (kappa) and two heavy (IgG1) chains. The heavy chain constant region contains two point mutations, L235A and G237A (LAGA), which reduce binding of the mAb to Fcγ receptors and prevent Fc-mediated effector function including CDC and ADCC. DRSPAI-L7B comprises a heavy chain having the amino acids set out in SEQ ID NO:2 and a light chain having the amino acids set out in SEQ ID NO:3.

In some embodiments, an IL-7 binding protein described herein comprises a heavy chain having at least 80%, 85%, 90% or 95% sequence identity to the amino acids set out in SEQ ID NO:19, 21, or 23. In some embodiments, an IL-7 binding protein described herein comprises a heavy chain having the amino acids set out in SEQ ID NO:19, 21, or 23. In some embodiments, an IL-7 binding protein described herein comprises a light chain having at least 80%, 85%, 90% or 95% sequence identity to the amino acids set out in SEQ ID NO: 18, 20, or 22. In some embodiments, an IL-7 binding protein described herein comprises a light chain having the amino acids set out in SEQ ID NO: 18, 20, or 22. In some embodiments, an IL-7 binding protein disclosed herein comprises a heavy chain having the amino acids set out in SEQ ID NO:19 and a light chain having the amino acids set out in SEQ ID NO:18. In some embodiments, an IL-7 binding protein disclosed herein comprises a heavy chain having the amino acids set out in SEQ ID NO:21 and a light chain having the amino acids set out in SEQ ID NO:20. In some embodiments, an IL-7 binding protein disclosed herein comprises a heavy chain having the amino acids set out in SEQ ID NO:23 and a light chain having the amino acids set out in SEQ ID NO:22.

In some embodiments, DRSPAI-L7B reduces survival and activation of pathogenic and memory T cells in the periphery, block establishment and maintenance of tertiary lymphoid organs (TLO) via its role in development of lymphoid tissue inducer cells (Lti) and ILC3, and does not impact regulatory T cell number or function. In some embodiments, DRSPAI-L7B functions peripherally and will reduce T cell trafficking to TLOs and the brain and thus does not require CNS penetration. With regard to MS, in some embodiments, DRSPAI-L7B will reduce inflammation and reduce chronic autoimmunity leading to reduction in relapse rate and delay in progression in both relapse remitting MS (RRMS) and primary progressive MS (PPMS).

The term "epitope" as used herein refers to that portion of the antigen that makes contact with a particular binding domain of the IL-7 binding protein, also known as the paratope. An epitope may be linear or conformational/discontinuous. A conformational or discontinuous epitope comprises amino acid residues that are separated by other sequences, i.e. not in a continuous sequence in the antigen's primary sequence assembled by tertiary folding of the polypeptide chain. Although the residues may be from different regions of the polypeptide chain, they are in close proximity in the three dimensional structure of the antigen. In the case of multimeric antigens, a conformational or discontinuous epitope may include residues from different peptide chains. Particular residues comprised within an epitope can be determined through computer modelling programs or via three-dimensional structures obtained through methods known in the art, such as X-ray crystallography. Epitope mapping can be carried out using various techniques known to persons skilled in the art as described in publications such as *Methods in Molecular Biology 'Epitope Mapping Protocols'*, Mike Schutkowski and Ulrich Reineke (volume 524, 2009) and Johan Rockberg and Johan Nilvebrant (volume 1785, 2018). Exemplary methods include peptide based approaches such as pepscan whereby a series of overlapping peptides are screened for binding using techniques such as ELISA or by in vitro display of large libraries of peptides or protein mutants, e.g. on phage. Detailed epitope information can be determined by structural techniques including X-ray crystallography, solution nuclear magnetic resonance (NMR) spectroscopy and cryogenic-electron microscopy (cryo-EM). Mutagenesis, such as alanine scanning, is an effective approach whereby loss of binding analysis is used for epitope mapping. Another method is hydrogen/deuterium exchange (HDX) combined with proteolysis and liquid-chromatography mass spectrometry (LC-MS) analysis to characterize discontinuous or conformational epitopes.

In one aspect, provided is an IL-7 binding protein which binds to human IL-7 at one or more amino acid residues within SEQ ID NO:1. In one embodiment, provided is an IL-7 binding protein which binds to human IL-7 at one or more amino acid residues within SEQ ID NO:12. In another embodiment, provided is an IL-7 binding protein which binds to human IL-7 at one or more amino acid residues within SEQ ID NO:16.

In another aspect, provided is an IL-7 binding protein which protects residues as set forth in SEQ ID NO: 12 of IL-7 from deuterium exchange in HDX-MS analysis. In one embodiment, provided is an IL-7 binding protein which protects residues 67 to 81 (SEQ ID NO:1) of IL-7 from deuterium exchange in HDX-MS analysis. In some embodiments, the IL-7 binding protein binds to a sequence having at least about 50%, 60%, 70%, 80%, 90% or 95% identity to the amino acid sequence set out in SEQ ID NO:12. In some embodiments, the IL-7 binding protein binds to a sequence having at least about 50%, 60%, 70%, 80%, 90% or 95% identity to the amino acid sequence set out in SEQ ID NO:16. In some embodiments, the IL-7 binding protein binds to IL-7 at a site that sits adjacent to a IL-7Rα and γ-chain interaction sites on the folded IL-7 protein. In some embodiments, the IL-7 binding protein exhibits binding specificity for IL-7 at an epitope comprising at least 5 contiguous amino acids of a sequence set out in SEQ ID NO:12. In some embodiments, the IL-7 binding protein exhibits binding specificity for IL-7 at an epitope comprising at least 5 contiguous amino acids of a sequence set out in SEQ ID NO:16. In some embodiments, the IL-7 binding protein exhibits binding specificity for IL-7 at an epitope comprising at least 10 contiguous amino acids of a sequence set out in SEQ ID NO:12. In some embodiments, the IL-7 binding protein exhibits binding specificity for IL-7 at an epitope comprising at least 10 contiguous amino acids of a sequence set out in SEQ ID NO:16.

In some embodiments, an affinity of an IL-7 binding protein to an antigen can be determined by a competitive binding assay. In some embodiments, a competitive binding assay is an immunoassay. In some embodiments, a competitive binding assay is for example, ELISA or a radioimmunoassay.

In some embodiments, reduction or inhibition in biological activity may be partial or total. A neutralizing IL-7 binding protein disclosed herein may neutralize the activity of IL-7 by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to IL-7 activity in the absence of the IL-7 binding protein. Neutralization may be determined or measured using one or more assays known to the skilled person or as described herein.

In some embodiments, an IL-7 binding protein disclosed herein targets membrane bound IL-7 receptor a (CD127), which upon IL-7 binding forms a heterodimeric receptor with the common γ chain (CD132). In some embodiments, an IL-7 binding protein disclosed herein targets soluble IL-7 receptor a (sCD127).

Competition between the IL-7 binding protein of the invention and a reference IL-7 binding protein, e.g. a reference antibody or an IL-7 receptor, may be determined by one or more techniques known to the skilled person such as ELISA, FMAT, Surface Plasmon Resonance (SPR) or ForteBio Octet Bio-Layer Interferometry (BLI). Such techniques may also be referred to as epitope binning. There are several possible reasons for this competition: the two proteins may bind to the same or overlapping epitopes, there may be steric inhibition of binding, or binding of the first protein may induce a conformational change in the antigen that prevents or reduces binding of the second protein.

The reduction or inhibition in biological activity may be partial or total. A neutralising antigen binding protein may neutralise the activity of <target> by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to <target> activity in the absence of the antigen binding protein.

Neutralisation may be determined or measured using one or more assays known to the skilled person or as described herein.

Percent Identity

"Percent identity" between a query nucleic acid sequence and a subject nucleic acid sequence is the "Identities" value, expressed as a percentage, that is calculated using a suitable algorithm or software, such as BLASTN, FASTA, DNASTAR Lasergene, GeneDoc, Bioedit, EMBOSS needle or EMBOSS infoalign, over the entire length of the query sequence after a pair-wise global sequence alignment has been performed using a suitable algorithm or software, such as BLASTN, FASTA, ClustalW, MUSCLE, MAFFT, EMBOSS Needle, T-Coffee, and DNASTAR Lasergene. Importantly, a query nucleic acid sequence may be described by a nucleic acid sequence identified in one or more claims herein.

"Percent identity" between a query amino acid sequence and a subject amino acid sequence is the "Identities" value, expressed as a percentage, that is calculated using a suitable algorithm or software, such as BLASTP, FASTA, DNASTAR Lasergene, GeneDoc, Bioedit, EMBOSS needle or EMBOSS infoalign, over the entire length of the query sequence after a pair-wise global sequence alignment has been performed using a suitable algorithm/software such as BLASTP, FASTA, ClustalW, MUSCLE, MAFFT, EMBOSS Needle, T-Coffee, and DNASTAR Lasergene. Importantly, a query amino acid sequence may be described by an amino acid sequence identified in one or more claims herein.

The query sequence may be 100% identical to the subject sequence, or it may include up to a certain integer number of amino acid or nucleotide alterations as compared to the subject sequence such that the % identity is less than 100%. For example, the query sequence is at least 50, 60, 70, 75, 80, 85, 90, 95, 96, 97, 98, or 99% identical to the subject sequence. Such alterations include at least one amino acid deletion, substitution (including conservative and non-conservative substitution), or insertion, and wherein said alterations may occur at the amino- or carboxy-terminal positions of the query sequence or anywhere between those terminal positions, interspersed either individually among the amino acids or nucleotides in the query sequence or in one or more contiguous groups within the query sequence.

The % identity may be determined across the entire length of the query sequence, including the CDRs. Alternatively, the % identity may exclude one or more or all of the CDRs, for example all of the CDRs are 100% identical to the subject sequence and the % identity variation is in the remaining portion of the query sequence, e.g. the framework sequence, so that the CDR sequences are fixed and intact. In some embodiments, a variant sequence substantially retains the biological characteristics of the unmodified protein, such as DRSPAI-L7B.

Modifications

The skilled person will appreciate that, upon production of an IL-7 binding protein, such as an antibody in a host cell, post-translational modifications may occur. For example, this may include the cleavage of certain leader sequences, the addition of various sugar moieties in various glycosylation patterns, non-enzymatic glycation, deamidation, oxidation, disulfide bond scrambling and other cysteine variants such as free sulfhydryls, racemized disulfides, thioethers and trisulfide bonds, isomerization, C-terminal lysine clipping, and N-terminal glutamine cyclisation. The disclosure encompasses the use of IL-7 binding proteins that have been subjected to, or have undergone, one or more post-translational modifications. Thus an "IL-7 binding protein" or "antibody" of the invention includes an "IL-7 binding protein" or "antibody", respectively, as defined earlier that has undergone a post-translational modification such as described herein.

Glycation is a post-translational non-enzymatic chemical reaction between a reducing sugar, such as glucose, and a free amine group in the protein, and is typically observed at the epsilon amine of lysine side chains or at the N-Terminus of the protein. Glycation can occur during production and storage only in the presence of reducing sugars.

Deamidation can occur during production and storage, is an enzymatic reaction primarily converting asparagine (N) to iso-aspartic acid (iso-aspartate) and aspartic acid (aspartate) (D) at approximately 3:1 ratio. This deamidation reaction is therefore related to isomerization of aspartate (D) to iso-aspartate. The deamidation of asparagine and the isomerization of aspartate, both involve the intermediate succinimide. To a much lesser degree, deamidation can occur with glutamine residues in a similar manner. Deamidation can occur in a CDR, in a Fab (non-CDR region), or in the Fc region.

Oxidation can occur during production and storage (i.e. in the presence of oxidizing conditions) and results in a covalent modification of a protein, induced either directly by reactive oxygen species or indirectly by reaction with secondary by-products of oxidative stress. Oxidation happens primarily with methionine residues, but may occur at tryptophan and free cysteine residues. Oxidation can occur in a CDR, in a Fab (non-CDR region), or in the Fc region.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

The formation of a thioether and racemization of a disulphide bond can occur under basic conditions, in production or storage, through a beta elimination of disulphide bridges back to cysteine residues via a dehydroalanine and persulfide intermediate. Subsequent crosslinking of dehydroalanine and cysteine results in the formation of a thioether bond or the free cysteine residues can reform a disulphide bond with a mixture of D- and L-cysteine.

Trisulfides result from insertion of a sulfur atom into a disulphide bond (Cys-S—S—S-Cys) and are formed due to the presence of hydrogen sulphide in production cell culture.

N-terminal glutamine (Q) and glutamate (glutamic acid) (E) in the heavy chain and/or light chain is likely to form pyroglutamate (pGlu) via cyclization. Most pGlu formation happens in the production bioreactor, but it can be formed non-enzymatically, depending on pH and temperature of processing and storage conditions. Cyclization of N-terminal Q or E is commonly observed in natural human antibodies.

C-terminal lysine clipping is an enzymatic reaction catalyzed by carboxypeptidases, and is commonly observed in recombinant and natural human antibodies. Variants of this process include removal of lysine from one or both heavy chains due to cellular enzymes from the recombinant host cell. Upon administration to the human subject/patient is likely to result in the removal of any remaining C-terminal lysines.

The terms "peptide", "polypeptide" and "protein" each refers to a molecule comprising two or more amino acid residues. A peptide may be monomeric or polymeric.

In some embodiments, it may be desirable to modify the effector function of the IL-7 binding protein, for instance, to enhance ADCC or CDC, half-life, etc. The IL-7 binding protein may have a half-life of at least 6 hours, at least 1 day, at least 2 days, at least 3 days, at least 4 days, at least 5 days, at least 7 days, or at least 9 days in vivo in humans, or in a murine animal model.

Mutational changes to the Fc effector portion of the antibody can be used to change the affinity of the interaction between the FcRn and antibody to modulate antibody turnover. The half-life of the antibody can be extended in vivo. This could be beneficial to patient populations as maximal dose amounts and maximal dosing frequencies could be achieved as a result of maintaining in vivo $IC_{50}$ for longer periods of time. The Fc effector function of the antibody may be removed, in its entirety or in part, since it may not be desirable to kill those cells expressing CD127. This removal may result in an increased safety profile.

In some embodiments, an IL-7 binding protein comprising a constant region may have reduced ADCC and/or complement activation or effector functionality. The constant domain may comprise a naturally disabled constant region of IgG2 or IgG4 isotype or a mutated IgG1 constant domain. In some embodiments, the IL-7 binding proteins of the invention may be Fc disabled. Examples of suitable modifications are described in EP0307434. One way to achieve Fc disablement comprises the substitutions of alanine residues at positions 235 and 237 (EU index numbering) of the heavy chain constant region, i.e. L235A and G237A (commonly referred to as "LAGA" mutations). Another example comprises substitution with alanines at positions 234 and 235 (EU index numbering), i.e. L234A and L235A (commonly referred to as "LALA" mutations). In some embodiments, the Fc effector function of an IL-7 binding protein disclosed herein has been disabled using the LAGA mutation. Alternatively, the IL-7 binding protein may be Fc enabled and not comprise the alanine substitutions at positions 235 and 237.

Additional alterations and mutations to decrease effector function include: (with reference to IgG1 unless otherwise noted): a glycosylated N297A or N297Q or N297G; L235E; IgG4:F234A/L235A; and chimeric IgG2/IgG4. IgG2: H268Q/V309L/A330S/P331S, and IgG2: V234A/G237A/P238S/H268A/V309L/A330S/P331S can reduce FcγR and C1q binding (Wang et al. 2018 and U.S. Pat. No. 8,961,967).

Other mutations that decrease effector function include L234F/L235E/P331S; a chimeric antibody created using the CH1 and hinge region from human IgG2 and the CH2 and CH3 regions from human IgG4; IgG2m4, based on the IgG2 isotype with four key amino acid residue changes derived from IgG4 (H268Q, V309L, A330S and P331S); IgG2σ which contains V234A/G237A/P238S/H268A/V309L/A330S/P331S substitutions to eliminate affinity for Fcγ receptors and C1q complement protein; IgG2m4 (H268Q/V309L/A330S/P331S, changes to IgG4); IgG4 (S228P/L234A/L235A); huIgG1 L234A/L235A (AA); huIgG4 S228P/L234A/L235A; IgG1σ (L234A/L235A/G237A/P238S/H268A/A330S/P331S); IgG4σ1 (S228P/F234A/L235A/G237A/P238S); and IgG4σ2 (S228P/F234A/L235A/G236/G237A/P238S, wherein denotes a deletion) (Tam et al., Antibodies 2017, 6(3)).

In some embodiments, an IL-7 binding protein disclosed herein may comprise one or more modifications selected from a mutated constant domain such that the antibody has enhanced effector functions/ADCC and/or complement activation. Examples of suitable modifications are described in Shields et al. J. Biol. Chem (2001) 276:6591-6604, Lazar et al. PNAS (2006) 103:4005-4010 and U.S. Pat. No. 6,737,056, WO2004063351 and WO2004029207. The IL-7 binding protein may comprise a constant domain with an altered glycosylation profile such that the IL-7 binding protein has enhanced effector functions/ADCC and/or complement activation. Examples of suitable methodologies to produce an IL-7 binding protein with an altered glycosylation profile are described in WO2003/011878, WO2006/014679 and EP1229125.

Host and Vector

The IL-7 binding proteins may be prepared by any of a number of conventional techniques. For example, IL-7 binding proteins may be purified from cells that naturally express them (e.g., an antibody can be purified from a hybridoma that produces it), or produced in recombinant expression systems.

A number of different expression systems and purification regimes can be used to generate the IL-7 binding protein of the invention. Generally, host cells are transformed with a recombinant expression vector encoding the desired antigen binding protein. The expression vector may be maintained by the host as a separate genetic element or integrated into the host chromosome depending on the expression system.

In some embodiments, an expression vector that comprises a nucleic acid molecule is described herein. Also provided is a recombinant host cell comprising an expression vector as described herein. An IL-7 binding protein described herein may be produced in a suitable host cell. A wide range of host cells can be employed, including Prokaryotes (including Gram negative or Gram positive bacteria, for example *Escherichia coli, Bacilli* sp., *Pseudomonas* sp., *Corynebacterium* sp.), Eukaryotes including yeast (for example *Saccharomyces cerevisiae, Pichia pastoris*), fungi (for example *Aspergillus* sp.), or higher Eukaryotes including insect cells and cell lines of mammalian origin. Examples of cell lines include Chinese Hamster Ovary (CHO) cells, PER.C6, HEK293, HeLa or NSO. In some embodiments, a host cell described herein is a CHO cell, NSO myeloma cells, COS cells or SP2 cells. The host cell may be a non-human host cell. The host cell may be a non-embryonic host cell. Human cells may be used, thus enabling modified human glycosylation patterns. Alternatively, other eukaryotic cell lines may be employed. In some embodiments, selection of suitable mammalian host cells and methods for transformation, culture, amplification, screening and product production and purification are known in the art. In some embodiments, the host cell is a strain of yeast. The host cell may be cultured in a culture media, for example serum-free culture media. The IL-7 binding protein may be secreted by the host cell into the culture media. The IL-7 binding protein can be purified to at least 95% or greater (e.g. 98% or greater) with respect to the culture media containing the IL-7 binding protein.

The host cell may be an isolated host cell. The host cell is usually not part of a multicellular organism (e.g., plant or animal). The host cell may be a non-human host cell.

Appropriate cloning and expression vectors for use with bacterial, fungal, yeast, and mammalian host cells are known in the art.

A method for the production of the IL-7 binding protein as described herein may comprise the step of culturing a host cell and recovering the IL-7 binding protein. In one aspect of the invention, there is provided a method of making an IL-7 binding protein the method comprising maintaining a host cell in a medium to produce the IL-7 binding protein and isolating or purifying the IL-7 binding protein produced by the host cell.

A recombinant transformed, transfected, or transduced host cell may comprise at least one expression cassette, whereby the expression cassette comprises a polynucleotide encoding a heavy chain of the IL-7 binding protein described herein and further comprises a polynucleotide encoding a light chain of the IL-7 binding protein described herein. Alternatively, a recombinant transformed, transfected or transduced host cell may comprise at least one expression cassette, whereby a first expression cassette comprises a polynucleotide encoding a heavy chain of the IL-7 binding protein described herein and further comprise a second cassette comprising a polynucleotide encoding a light chain of the IL-7 binding protein described herein. A stably transformed host cell may comprise a vector comprising one or more expression cassettes encoding a heavy chain and/or a light chain of the IL-7 binding protein described herein or fragments thereof. For example, such host cells may comprise a first vector encoding the light chain and a second vector encoding the heavy chain.

The cells can be cultured under conditions that promote expression of the antigen binding protein using a variety of equipment such as shake flasks, spinner flasks, and bioreactors. The polypeptide is recovered by conventional protein purification procedures. Protein purification procedures typically consist of a series of unit operations comprised of various filtration and chromatographic processes developed to selectively concentrate and isolate the antigen binding protein. The purified antigen binding protein may be formulated in a pharmaceutically acceptable composition.

STATEMENT OF USE

In one aspect, an IL-7 binding protein described herein is for use in therapy. An IL-7 binding protein described herein can be used in the treatment of diseases or conditions for which an IL-7 inhibitor is indicated, for example inflammatory or autoimmune diseases. In some embodiments, IL-7 inhibition by an IL-7 binding protein described herein impacts the survival, expansion and function of autoreactive effector T cells, while sparing regulatory T lymphocytes. In some embodiments, IL-7 inhibition by an IL-7 binding protein described herein inhibits the formation of ectopic lymphoid tissue. In some embodiments, IL-7 inhibition by an IL-7 binding protein described herein may help to restore homeostasis by inhibiting innate lymphoid cell (ILC) survival.

In some embodiments, an IL-7 binding protein disclosed herein is capable of antagonizing the biological effect of IL-7 and is capable of antagonizing at least one of IL-7R-mediated $T_H17$ expansion, and IL-7R-mediated $T_H17$ survival. The term inhibit, antagonize and neutralize are used herein synonymously. No term is intended to suggest the requirement of total neutralization; partial neutralization—corresponding to a reduction but not complete abolition of the biological effect—is also contemplated.

At a molecular level, $T_H17$ expansion and/or survival can be observed by an increase in IL-17 production by a population of CD4+ T cells (or by a population of $T_H17$ cells). In an embodiment, therefore, the IL-7 binding proteins disclosed herein reduces IL-17 production by a population of CD4+ T cells. IL-7 receptor mediated $T_H17$ expansion and survival can also be observed by an increase in IFN-γ production by a population of CD4+ T cells (or by a population of $T_H17$ cells). Thus, in an embodiment, the IL-7 binding proteins disclosed herein antagonize (reduce) IFN-γ production by a population of CD4+ T cells. At a molecular level, the IL-7 binding proteins disclosed herein may inhibit IL-7 receptor mediated STAT-5 phosphorylation.

In some embodiments, at the molecular level, one can observe and measure the blocking effect of the IL-7 binding proteins described herein by assays such as IL-7-induced P-STAT5 or Bcl-2. In some embodiments, at the cellular level, one can observe and measure the blocking effect by assays such as $T_H17$ secretion of IL-17 or IFNγ. Exemplary assays are described in PCT application number PCT/US2009/053136 (WO2010/017468). In an exemplary pSTAT-5 assay, PBMCs can be stimulated with IL-7 in the presence and absence of a test agent. Cells can be subsequently assessed quantitatively for the level of pSTAT-5, e.g. by staining for pSTAT-5 (e.g. with a labelled anti-pSTAT-5 antibody, such as ALEXA FLUOR 647 Mouse Anti-Stat5 (pY694, BD [#612599])) followed by fluorescence activated cell sorting. The levels of phosphorylated STAT-5 could also be determined by ELISA. Those agents which reduce the level of phosphorylated STAT-5 may be potential therapeutic candidates for autoimmune disease.

In some embodiments, the disclosure provides a method for the treatment of an autoimmune disease in a human subject, comprising administering to the subject an IL-7 binding protein in an amount sufficient to reduce IL-7R-mediated STAT-5 phosphorylation. In some embodiments, an IL-7 binding protein disclosed herein blocks or inhibits IL-7 mediated phosphorylation of STAT5 directly downstream of IL-7R. In some embodiments, an IL-7 binding protein disclosed herein downregulates surface expression of activation markers and chemokine receptors responsible for lymphocyte trafficking to the CNS on active $T_H1$ cells.

An antagonist, such as the antigen-binding protein of the disclosure may be capable of reducing levels of phosphorylated STAT-5 by at least 20%, 50%, 75%, 80%, 85%, 90%, 95% or 100% when compared to STAT-5 levels in the absence of the antagonist, or when compared to a negative control, or untreated cells. The antagonist may have an $IC_{50}$ of 50 µg/ml, 25 µg/ml or less, 104 g/ml or less, 5 µg/ml or less, or 2 µg/ml or less. In an embodiment, the antagonist has an $IC_{50}$ of less than or equal to 1 µg/ml, less than or equal to 0.75 µg/ml, less than or equal to 0.5 µg/ml, less than or equal to 0.25 µg/ml, or less than or equal to 0.1 µg/ml. In one embodiment, the antagonist has an $IC_{50}$ of less than or equal to 50 ng/ml, less than or equal to 40 ng/ml, less than or equal to 30 ng/ml, less than or equal to 20 ng/ml or less than or equal to 10 ng/ml. In one embodiment, the antagonist has an $IC_{50}$ of 5 ng/ml.

An antagonist disclosed herein may be particularly effective in inhibiting the expansion of $T_H17$ cells. Expansion of $T_H17$ cells can be determined in a $T_H17$ expansion assay, which can comprise stimulating a population of naïve T cells to expand in the presence and absence of a test agent, followed by stimulating the cells to produce IL-17 and assessing the level of IL-17 produced by the cells in the presence and absence of the test agent. In an exemplary assay, human CD4+ T cells can be differentiated into $T_H17$ by stimulation with T cell receptor activation in the presence of IL-1, IL-6, and IL-23. After 5 days of differentiation, CCR6+ cells can be sorted out to produce an enriched $T_H17$ population. This population can then be stimulated with human IL-7 and the increase in IL-17 and IFN-γ in the supernatant can be determined. The ability of a test agent, such as an antigen binding fragment of the present disclosure, to inhibit induction of IL-7R by IL-7 can be determined as the presence of an antagonist of this interaction during the incubation period should prevent the expansion of the $T_H17$ cells leading to the reduction of IL-17 and IFN-γ production.

The IL-7 binding proteins may be capable of from 20% or more inhibition of IL-17 secretion in such an assay, versus a negative control. More typically, the IL-7 binding protein is capable of from 50%, from 75%, from 85% or from 90% or more inhibition of IL-17 secretion versus the control. The IL-7 binding protein may, in some embodiments, exhibit an $IC_{50}$ of less than or equal to 50 µg/ml in the assay. In other embodiments, the $IC_{50}$ may be less than or equal to 20 µg/ml, 10 µg/ml or 5 µg/ml. Thus, in another aspect, the disclosure provides a method for the treatment of an autoimmune disease or inflammatory disorder, comprising administering to a patient an IL-7 binding protein disclosed herein in an amount sufficient to reduce the $T_H17$ cell count in the patient.

In some embodiments, an IL-7 binding protein disclosed herein is for the treatment of a subject. The terms "individual", "subject" and "patient" are used herein interchangeably. The subject is typically a human. The subject may also be a mammal, such as a mouse, rat or primate (e.g. a marmoset or monkey). The subject can be a non-human animal. The IL-7 binding proteins may also have veterinary use. The subject to be treated may be a farm animal for example, a cow or bull, sheep, pig, ox, goat or horse or may be a domestic animal such as a dog or cat. The animal may be any age, or a mature adult animal. In some embodiments, treatment may be therapeutic, prophylactic or preventative. The subject may be one who is in need thereof. Those in need of treatment may include individuals already suffering from a medical disease in addition to those who may develop the disease in the future.

Thus, the IL-7 binding protein described herein can be used for prophylactic or preventative treatment. In this case, the IL-7 binding protein described herein is administered to an individual in order to prevent or delay the onset of one or more aspects or symptoms of a disease. The subject can be asymptomatic. The subject may have a genetic predisposition to the disease. In some embodiments, a prophylactically effective amount of the IL-7 binding protein is administered to such an individual. In some embodiments, a prophylactically effective amount is an amount which prevents or delays the onset of one or more aspects or symptoms of a disease described herein.

The IL-7 binding protein described herein may also be used in methods of therapy. The term "therapy" encompasses alleviation, reduction, or prevention of at least one aspect or symptom of a disease. For example, the IL-7 binding protein described herein may be used to ameliorate or reduce one or more aspects or symptoms of a disease described herein.

In some embodiments, an IL-7 binding protein described herein is used in an effective amount for therapeutic, prophylactic or preventative treatment. In some embodiments, a therapeutically effective amount of the IL-7 binding protein described herein is an amount effective to ameliorate or reduce one or more aspects or symptoms of the disease. In some embodiments, the IL-7 binding protein described herein may also be used to treat, prevent, or cure the disease described herein. In some embodiments, an IL-7 binding protein described herein has a generally beneficial effect on the subject's health, for example it can increase the subject's expected longevity.

The IL-7 binding protein described herein need not affect a complete cure or eradicate every symptom or manifestation of the disease to constitute a viable therapeutic treatment. As is recognized in the pertinent field, drugs employed as therapeutic agents may reduce the severity of a given disease state but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

In some embodiments, an IL-7 binding protein described herein may be used in a therapy to treat a subject having or suspected of having a disease or condition described herein. In some embodiments, an IL-7 binding protein described herein is administered to a subject having or suspected of having a disease or condition described herein. In some embodiments, an IL-7 binding protein described herein may be used in the therapy of multiple sclerosis (MS) and in other autoimmune or inflammatory diseases, particularly those in which pathogenic $T_H17$ cells are implicated. In some embodiments, an IL-7 binding protein described herein may be used in the therapy of rheumatoid arthritis, psoriasis, Behcet's disease, diabetes, for example type I diabetes and systemic lupus erythematosus (SLE).

Inhibition of IL-7-induced IL-7R-mediated signaling may be useful in the treatment of inflammatory (non-autoimmune) diseases in which elevated IL-17 or IL-2 has been implicated, such as asthma. Accordingly, inflammatory and/or autoimmune diseases that may be treated by an IL-7 binding protein disclosed herein include inflammatory skin diseases including psoriasis and atopic dermatitis; systemic scleroderma and sclerosis; inflammatory bowel disease (IBD); Crohn's disease; ulcerative colitis; ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); dermatitis; meningitis; encephalitis; uveitis; osteoarthritis; lupus nephritis; autoimmune diseases such as rheumatoid arthritis (RA), spondyloarthritis, Sjogren's syndrome, vasculitis; diseases involving leukocyte diapedesis; central nervous system (CNS) inflammatory disorder, multiple organ injury syndrome secondary to septicemia or trauma; alcoholic hepatitis; bacterial pneumonia; antigen-antibody complex mediated diseases including glomerulonephritis; sepsis; sarcoidosis; immunopathologic responses to tissue/organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; psoriatic arthritis; neuromyelitis optica, Guillain-Barre syndrome (GBS), COPD, type 1 diabetes, etc.

In particular, an IL-7 binding protein disclosed herein may be useful in the therapy of multiple sclerosis, in all its forms, including neuromyelitis optica. In some embodiment, an IL-7 binding protein disclosed herein is useful in the therapy of multiple sclerosis classified as clinically-isolated syndrome (CIS); primary-progressive (PPMS); relapsing-remitting (RRMS) and/or secondary progressive (SPMS). In some embodiments, treatment with an IL-7 binding protein disclosed herein is predicted to be most efficacious when administered in the context of active inflammatory disease, i.e. when used in the treatment of clinically isolated syndrome or relapsing forms of MS. These stages of disease can be defined clinically and/or by imaging criteria such as gadolinium enhancement or other more sensitive techniques, and/or other as yet undefined biomarkers of active disease. Particularly, an IL-7 binding protein disclosed herein can be used to treat RRMS (via intravenous, subcutaneous, oral or intramuscular delivery) when subjects are entering or are in relapse. In an embodiment, an IL-7 binding protein disclosed herein is administered to a subject at the onset of relapse, or within 1 hr, 2 hrs, 3 hrs, 6 hrs, 12 hrs, 24 hrs, 2 days, 3 days, 4 days, 5 days, 6 days, 7 days, 8 days, 9 days or 10 days from the onset of relapse.

In some embodiment, an autoimmune and/or inflammatory disease is selected from IBD, rheumatoid arthritis (RA), Sjögren's syndrome, Crohn's disease, diabetes, for example type I diabetes, systemic lupus erythematosus (SLE) and ulcerative colitis. In another embodiment, the autoimmune and/or inflammatory condition is rheumatoid arthritis (RA). In another embodiment, the autoimmune and/or inflammatory condition is Sjögren's syndrome. In another embodiment, the autoimmune and/or inflammatory condition is systemic lupus erythematosus (SLE). In another embodiment, the autoimmune and/or inflammatory condition is ulcerative colitis. In another embodiment, the autoimmune and/or inflammatory condition is diabetes, for example type I diabetes.

In some embodiments, provided herein is an IL-7 binding protein for use in the treatment of a disease or condition disclosed herein. In some embodiments, provided herein are IL-7 binding proteins for use in the treatment of an autoimmune and/or inflammatory disease. In some embodiments, provided herein are IL-7 binding proteins for use in the treatment of multiple sclerosis (MS). In some embodiments, disclosed herein is an IL-7 binding protein for use in the treatment of relapsing remitting MS, secondary progressive MS, and/or primary progressive MS. In some embodiments, provided herein is an IL-7 binding protein for use in the treatment of rheumatoid arthritis (RA). In some embodiments, provided herein is an IL-7 binding protein for use in the treatment of Sjögren's syndrome. In some embodiments, provided herein is an IL-7 binding protein for use in the treatment of systemic lupus erythematosus (SLE). In some embodiments, provided herein is an IL-7 binding protein for use in the treatment of ulcerative colitis. In some embodiments, provided herein is an IL-7 binding protein for use in the treatment of diabetes, for example type I diabetes.

In some embodiments, provided herein is the use of an IL-7 binding protein in the manufacture of a medicament for the treatment of a disease or condition disclosed herein. In some embodiments, provided herein is the use of an IL-7 binding protein in the manufacture of a medicament for the treatment of an autoimmune and/or inflammatory disease. In some embodiments, provided herein is the use of an IL-7 binding protein in the manufacture of a medicament for the treatment of multiple sclerosis. In some embodiments, provided herein is the use of an IL-7 binding protein in the manufacture of a medicament for the treatment of rheumatoid arthritis (RA). In some embodiments, provided herein is the use of an IL-7 binding protein in the manufacture of a medicament for the treatment of Sjögren's syndrome. In some embodiments, provided herein is the use of an IL-7 binding protein in the manufacture of a medicament for the treatment of systemic lupus erythematosus (SLE). In some embodiments, provided herein is the use of an IL-7 binding protein in the manufacture of a medicament for the treatment of ulcerative colitis. In some embodiments, provided herein is the use of an IL-7 binding protein in the manufacture of a medicament for the treatment of diabetes, for example type I diabetes.

Also provided is a method for treatment of an autoimmune and/or inflammatory condition in a subject in need thereof, comprising administering to the subject a therapeutically effective amount of an IL-7 binding protein disclosed herein. In some embodiments, provided is a method for treating rheumatoid arthritis (RA) in a subject in need thereof, comprising administering to said subject a therapeutically effective amount of an IL-7 binding protein disclosed herein. In some embodiments, provided is a method for treating Sjögren's syndrome in a subject in need thereof, comprising administering to said subject a therapeutically effective amount of an IL-7 binding protein disclosed herein. In some embodiments, provided is a method for treating systemic lupus erythematosus (SLE) in a subject in need thereof, comprising administering to said subject a therapeutically effective amount of an IL-7 binding protein disclosed herein. In some embodiments, provided is a method for treating ulcerative colitis in a subject in need thereof, comprising administering to said subject a therapeutically effective amount of an IL-7 binding protein disclosed herein. In some embodiments, provided herein is a method for treating multiple sclerosis in a subject in need thereof, comprising administering to said subject a therapeutically effective amount of an IL-7 binding protein disclosed herein. In some embodiments, provided herein is a method for treating diabetes, for example type I diabetes in a subject in need thereof, comprising administering to said subject a therapeutically effective amount of an IL-7 binding protein disclosed herein.

In some embodiments, disclosed herein is a method for treating multiple sclerosis in a patient comprising administering an IL-7 binding protein disclosed herein to the patient, wherein the patient is suffering from relapsing remitting multiple sclerosis. In some embodiments, disclosed herein is a method for treating an autoimmune or inflammatory disease in a human subject, comprising administering to the subject an IL-7 binding protein disclosed herein to the patient in an amount effective to reduce the ratio of $T_H17$ cells relative to $T_H1$ cells. In some embodiments, disclosed herein is a method for treating an autoimmune or inflammatory disease in a human subject, comprising administering to the subject an IL-7 binding protein disclosed herein to the patient in an amount effective to reduce the ratio of $T_H$ cells relative to (Foxp3+) $T_{reg}$ cells.

In some embodiments, a treatment may comprise further monitoring of a disease or condition of a subject. A treatment may comprise a single treatment. A treatment may comprise a recurring treatment. A treatment may comprise a recurring treatment over a remaining lifespan of a subject. A treatment may comprise a daily treatment. A treatment may comprise a biweekly treatment. In some embodiments, a treatment may be selected based on an assessment of a patient or a sample obtained from the patient.

Pharmaceutical Compositions/Routes of Administration/Dosages

IL-7 binding protein as described herein may be incorporated into pharmaceutical compositions for use in the treatment of the human diseases described herein. In one embodiment, the pharmaceutical composition comprises an IL-7 binding protein in combination with one or more pharmaceutically acceptable carriers and/or excipients.

Such compositions comprise a pharmaceutically acceptable carrier as known and called for by acceptable pharmaceutical practice. In one embodiment, the pharmaceutical composition comprises a pharmaceutically-acceptable carrier or excipient and an IL-7 binding protein that exhibits binding for IL-7 at an epitope comprising at least 5 contiguous amino acids of a sequence set out in SEQ ID NO:12 or SEQ ID NO:16

Pharmaceutical compositions of the disclosures may be used for therapeutic or prophylactic applications. In some embodiments, provided are pharmaceutical compositions comprising an IL-7 binding protein and a pharmaceutically acceptable carrier or excipient thereof. In another embodiment, provided are pharmaceutical compositions comprising 1-500 mg of an IL-7 binding protein disclosed herein. In another embodiment, provided are pharmaceutical composition comprising 20-300 mg of an IL-7 binding protein disclosed herein. In another embodiment, provided are pharmaceutical compositions comprising 50-200 mg of an IL-7 binding protein disclosed herein. In a further embodiment, provided herein are pharmaceutical compositions comprising 50-200 mg of an IL-7 binding protein which is an antibody comprising a light chain amino acid sequence as set out in SEQ ID NO:3 and a heavy chain amino acid sequence as set out in SEQ ID NO:2. In a further embodiment, provided herein are pharmaceutical compositions comprising 50-200 mg of an IL-7 binding protein which is an antibody comprising a light chain amino acid sequence as set out in SEQ ID NO:18 and a heavy chain amino acid sequence as set out in SEQ ID NO:19. In a further embodiment, provided herein are pharmaceutical compositions comprising 50-200 mg of an IL-7 binding protein which is an antibody comprising a light chain amino acid sequence as set out in SEQ ID NO:20 and a heavy chain amino acid sequence as set out in SEQ ID NO:21. In a further embodiment, provided herein are pharmaceutical compositions comprising 50-200 mg of an IL-7 binding protein which is an antibody comprising a light chain amino acid sequence as set out in SEQ ID NO:22 and a heavy chain amino acid sequence as set out in SEQ ID NO:23. In some embodiments, a pharmaceutical composition described herein contains 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, or 110 mg of an IL-7 binding protein disclosed herein.

In some embodiments, the therapeutic agent of the disclosure (IL-7 binding protein), when in a pharmaceutical preparation, is present in unit dose forms. In some embodiments, the dosage regimen will be determined by a medical profession and/or clinical factors. As is well known in the medical arts, dosages for any one patient depend upon many factors, including the patient's size, body surface area, age, the compound to be administered, sex, time and route of administration, general health, and other drugs being administered concurrently. Exemplary doses can vary according to the size and health of the individual being treated, as well as the condition being treated. For example, in some embodiments, the disclosed antibodies or functional fragments may be administered in a dose of 1-100 mg/kg. In some embodiments, the disclosed IL-7 binding proteins may be administered in a dose of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 mg/kg. In some embodiments, a pharmaceutical composition disclosed herein is administered in a volume of at greater than at most about 5 mL, 10 mL, 15 mL, 20 mL, 25 mL, 30 mL, 35 mL, 40 mL, 45 mL, 50 mL, 60 mL, 70 mL, 80 mL, 90 mL, 100 mL, 110 mL, 120 mL, 130 mL, 140 mL, 150 mL, 200 mL, 300 mL, 400 mL, or 500 mL. In some embodiments, pharmaceutical compositions disclosed herein are administered multiple times at these dosages. In some embodiments, the dosage is administered a single time or multiple times, for example daily, weekly, biweekly, or monthly, hourly, or is administered upon recurrence, relapse or progression of a disease or condition being treated. In some embodiments, administration of a dose may be by slow continuous infusion over a period of from about 2 to about 24 hours, such as from about 2 to about 12 hours, or from about 2 to about 6 hours.

In some embodiments, the pharmaceutical composition comprises a composition for parenteral, transdermal, intraluminal, intraarterial, intrathecal and/or intranasal administration or by direct injection into tissue. In some embodiments, the pharmaceutical composition is administered to a patient via infusion or injection. In one embodiment, provided are pharmaceutical compositions comprising an IL-7 binding protein for intravenous administration. In some embodiments, provided are pharmaceutical compositions comprising an IL-7 binding protein for subcutaneous administration. In some embodiment, a pharmaceutical composition described herein is administered to a subject transarterially, subcutaneously, intradermally, intratumorally, intranodally, intramedullary, intramuscularly, by intravenous (i.v.) injection, by intravenous (i.v.) infusion, or intraperitoneally. In some embodiments, the IL-7 binding protein or pharmaceutical compositions thereof are administered to a subject by intradermal or subcutaneous injection.

In some embodiments, a pharmaceutical composition is prepared by per se known methods for the preparation of pharmaceutically acceptable compositions that are administered to subjects, such that an effective quantity of an IL-7 binding protein is combined in a mixture with a pharmaceutically acceptable carrier. Suitable carriers are described, for example, in Remington's Pharmaceutical Sciences (Remington's Pharmaceutical Sciences, 20$^{th}$ ed., Mack Publishing Company, Easton, Pa., USA, 2000). On this basis, the compositions may include, albeit not exclusively, solutions of the substances in association with one or more pharmaceutically acceptable carriers or diluents, and contained in buffered solutions with a suitable pH and iso-osmotic with the physiological fluids. In some embodiments, a pharmaceutical composition disclosed herein is acidic. In some embodiments, a pharmaceutical composition disclosed herein is basic. In some embodiments, a pharmaceutical composition can have a pH of about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, or about 14.

In some embodiments, suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, N-(1(2,3-dioleyloxy)propyl)N,N,N-trimethylammonium chloride (DOTMA), diolesylphosphotidylethanolamine (DOPE), and liposomes. In some embodiments, such compositions contain a therapeutically effective amount of an IL-7 binding protein disclosed herein, together with a suitable amount of carrier so as to provide the form for direct administration to a subject.

Pharmaceutical compositions may include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, preservatives, polyols, glycerin and vegetable oils, for example. Extemporaneous injection solutions and suspensions may be prepared from sterile powders, granules, tablets, or concentrated solutions or suspensions.

A pharmaceutical composition disclosed herein may be formulated into a variety of forms and administered by a number of different means. A pharmaceutical formulation can be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. Administration includes injection or infusion, including intra-arterial, intracardiac, intracerebroventricular, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration. In some exemplary embodiments, a route of administration is via an injection such as an intramuscular, intravenous, subcutaneous, or intraperitoneal injection.

Liquid formulations may include an oral formulation, an intravenous formulation, an intranasal formulation, an ocular formulation, an optic formulation, an aerosol, and the like. In certain embodiments, a combination of various formulations is administered. In certain embodiments a composition is formulated for an extended release profile.

Pharmaceutical compositions of the disclosure can be administered in combination with other therapeutics or treatments. In some embodiments, a treatment for a subject can be a surgery, a nutrition regime, a physical activity, an immunotherapy, a pharmaceutical composition, a cell transplantation, a blood fusion, or any combination thereof.

In some embodiments, a compositions/formulation disclosed herein is a stable. In some embodiments, a "stable" formulation is one in which the IL-7 binding protein therein essentially retains its physical and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs (1991) and Jones, A. Adv. Drug Delivery Rev. 10: 29-90 (1993), for example. Stability can be measured at a selected temperature for a selected time period. In some embodiments, the formulation is stable at ambient temperature or at 40° C. for at least 1 month and/or stable at 2-8° C. for at least 1 to 2 years. In some embodiments, the formulation is stable following freezing (e.g. to −70° C.) and thawing. In some embodiments, a protein "retains its physical stability" in a formulation if it shows little to no change in aggregation, precipitation and/or denaturation as observed by visual examination of color and/or clarity, or as measured by UV light scattering (measures visible aggregates) or size exclusion chromatography (SEC). SEC measures soluble aggregates that are not necessarily a precursor for visible aggregates. In some embodiments, a protein "retains its chemical stability" in a formulation if the chemical stability at a given time is such that the protein is considered to retain its biological activity. Chemically degraded species may be biologically active and chemically unstable. Chemical stability can be assessed by detecting and quantifying chemically altered forms of the protein. Chemical alteration may involve size modification (e.g. clipping) which can be evaluated using SEC, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

In some embodiments, an IL-7 binding protein described herein is a dimer at a concentration of least about 2, 3, 4, 5 mg/ml in an acetate buffer and is monomeric at a concentration of less than about 5,4, 3, 2, 1 mg/ml. In some embodiments, an IL-7 binding protein described herein is a dimer at a concentration of about 5 mg/ml in an acetate buffer and is monomeric at a concentration of about 1 mg/ml. In some embodiments, the IL-7 binding protein is a reversible dimer. In some embodiments, the IL-7 binding protein is a dimer. In some embodiments, the IL-7 binding protein is a monomer.

In an some embodiments, an IL-7 binding protein "retains its biological activity" in a pharmaceutical formulation, if the biological activity of the IL-7 binding protein at a given time is within about 10% (within the errors of the assay) of the biological activity exhibited at the time the pharmaceutical formulation was prepared as determined in an antigen binding assay, for example.

In some embodiments, a buffer disclosed herein refers to a buffered solution that resists changes in pH by the action of its acid-base conjugate components. In some embodiments, a buffer can be phosphate, citrate and other organic acids. In some embodiments, a buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, sodium citrate, sodium borate, tris(hydroxymethyl)-aminomethan, bicine, tricine, malic acid, succinate, maleic acid, fumaric acid, tartaric acid, aspartic acid or mixtures thereof. A composition disclosed herein can comprise antioxidants including ascorbic acid and/or methionine. In some embodiments, a composition disclosed herein comprises a preservative. In some embodiments, a preservative is a compound which can be included in a formulation to essentially reduce microbial including bacterial action therein, thus facilitating the production of a multi-use formulation, for example. Examples of potential preservatives include octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some embodiments, a composition disclosed herein may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

In some embodiments, an IL-7 binding protein disclosed herein may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

In some embodiments, an IL-7 binding protein disclosed herein is prepared in a sustained-release preparation. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

In some embodiments, disclosed herein are pharmaceutical compositions comprising the IL-7 binding protein which is present in a concentration from 1 mg/ml to 500 mg/ml, and wherein the composition has a pH from 2.0 to 10.0. The composition may further comprise a buffer system, preservative(s), tonicity agent(s), chelating agent(s), stabilizers and surfactants. In some embodiments, the pharmaceutical composition is an aqueous formulation, for example, formulation comprising water. Such formulation is typically a solution or a suspension. In a further embodiment, the pharmaceutical formulation is an aqueous solution. In some embodiments, an aqueous formulation is a formulation comprising at least 50% w/w water. In some embodiments an aqueous solution is defined as a solution comprising at least 50% w/w water. In some embodiments, the pharmaceutical composition is a stable liquid aqueous pharmaceutical formulation comprising an anti-human IL-7 binding protein described herein at a concentration of 20 to 150 mg/ml, a tonicity agent, a surfactant, and a buffer system having a pH of 4.0 to 8.0.

The pharmaceutical compositions may also comprise additional stabilizing agents, that may further enhance stability of a therapeutically active IL-7 binding protein. Stabilizing agents of can include, but are not limited to, methionine and EDTA, which protect the polypeptide against methionine oxidation, and a nonionic surfactant, which protects the polypeptide against aggregation associated with freeze-thawing or mechanical shearing. In some embodiments, the composition may further comprise a surfactant. The surfactant may be selected from a detergent, ethoxylated castor oil, polyglycolyzed glycerides, acetylated monoglycerides, sorbitan fatty acid esters, polyoxypropylene-polyoxyethylene block polymers (e.g. poloxamers such as PLURONIC F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (e.g. phosphatidyl serine, phosphatidyl choline, phosphatidyl ethanolamine, phosphatidyl inositol, diphosphatidyl glycerol and sphingomyelin), derivates of phospholipids (e.g. dipalmitoyl phosphatidic acid) and lysophospholipids (e.g. palmitoyl lysophosphatidyl-L-serine and l-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (e.g. cephalins), glyceroglycolipids (e.g. galactopyransoide), sphingoglycolipids (e.g. ceramides, gangliosides), dodecylphosphocholine, hen egg lysolecithin, fusidic acid derivatives—(e.g. sodium taurodihydrofusidate etc.), long-chain fatty acids and salts thereof C6-C12 (e.g. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, Na-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (e.g. Dodecyl 1-D-glucopyranoside), poloxamines (e.g. Tetronic's), which are tetrafunctional block copolymers derived from sequential addition of propylene oxide and ethylene oxide to ethylenediamine, or the surfactant may be selected from the group of imidazoline derivatives, or mixtures thereof.

Diagnostic/Monitoring

In some embodiments, an IL-7 binding protein disclosed herein is used in a method of diagnosis or prognosis. In some embodiments, diagnosis includes determining whether a subject has a disease or condition and/or determining the severity of the disease or condition. In some embodiments, prognosis includes predicting whether or not a subject will develop a disease or condition, whether or not they will need treatment, the type of treatment the individual will need, whether or not they will respond to a treatment, whether or not and/or when they will suffer a disease episode, recurrence or relapse, and the severity or duration of a symptom or a disease episode, recurrence or relapse. In some embodiments, a method of diagnosis or prognosis may include selecting or recommending a suitable treatment for the individual, for example, based on the diagnosis or prognosis. In some embodiments, a selected or recommended treatment or combination of treatments may then be administered to the subject.

In some embodiments, an IL-7 binding protein disclosed herein is used to diagnose or use in prognosis of an autoimmune or inflammatory disease, particularly those in which pathogenic $T_H17$ cells are implicated. Such diseases are associated with high levels of IL-17 expression. Elevated levels of IL-17 have been reported in serum and CSF of MS patients (Matusevicius, D. et al.; Mult. Scler. 5, 101-104; 1999) and in the synovial fluid obtained from rheumatoid arthritis patients. IL-17 has also been implicated in psoriasis (Homey et al.; J. Immunol. 164(12):6621-32; 2000), while Hamzaoui et al reported high levels of IL-17 in Behcet's disease (Scand. J. Rhuematol.; 31:4, 205-210; 2002). Elevated IL-17 levels have also been observed in systemic lupus erythematosus (SLE) (Wong et al.; Lupus 9(8):589-93; 2000).

In some embodiments, a method disclosed herein comprises measuring a level of IL-7 in a subject or on/in a sample obtained from a subject. In some embodiments, measuring a level of IL-7 can be performed by a method and assay known in the art. In some embodiments, a level of IL-7 is compared to a reference level of IL-7. In some embodiments, a references level is indicative of a normal, non-diseases, disease, or disease stage. In some embodiments, a level of IL-7 is measured multiple times in a subject or from multiple samples obtained from a subject. In some embodiment, diagnostic or prognostic methods can be carried out in conjunction with one or more other assays or tests to refine the diagnosis or prognosis. For example, other markers may be included in the analysis.

Assaying a tissue sample of a subject may be performed at one or more time points. A separate tissue sample may be obtained from the subject for assaying at each of the one or more time points. Assaying at one or more time points may be performed on the same tissue sample. Assaying at one or more time points may provide an assessment of an effectiveness of a drug, a longitudinal course of a disease treatment regime, or a combination thereof. At each of the one or more time points, a tissue sample may be compared to a same reference. A tissue sample may be compared to a different reference at each of the one or more time points. The one or more time points may be the same. The one or more time points may be different. The one or more time points may comprise at least one time point prior to a therapeutic administration, at least one time point after a therapeutic administration, at least one time point prior to a positive disease diagnosis, at least one time point after a disease remission diagnosis, at least one time point during a disease treatment regime, or a combination thereof.

The methods as described herein may be used to monitor a subject having risk of developing a disease or condition, as a preventive measure. The methods as described herein may be used alone for diagnosis and/or monitoring efficacy of a treatment. The methods as described herein may be used in combination with other assays for diagnosis or monitoring (such as a cytological analysis or molecular profiling).

In some embodiments, an increased level of IL-7 or IL-7 receptor in a subject or sample, as compared with a reference sample or reference level, indicates a positive diagnosis relating to the presence of disease, for example that the individual has the relevant disease or condition or has more severe disease. In some embodiments, a subject having a disease or condition includes an individual suspected of having the disease or condition and/or an individual at risk of developing the disease or condition. For example, the individual may not have been formally diagnosed but may be suspected of having the disease or condition because of the presence of one or more symptoms. For example, IL-7 expression is increased in the circulation of individuals with lymphopenia and there is a strong inverse correlation between circulating IL-7 levels and the number of $CD4^+$ T cells (Mackall et al., 2011). In some embodiment, an IL-7 binding protein disclosed herein is used to detect lymphopenia.

In some embodiments, a method for predicting the responsiveness of a subject to a treatment may be carried out before administration of a therapy. The prediction may then be taken into account when selecting or recommending a suitable treatment for the individual. Alternatively, a method of predicting responsiveness to a treatment may be carried out after treatment with a therapy and used to monitor and predict the subject's response to treatment. For example, systemic levels of IL-7 may increase with the duration of disease (Khaibullin et al., 2017) and increased circulating IL-7 has been identified as a potential predictive biomarker for response to IFNβ treatment in MS. In some embodiments, circulating IL-7 increases in Chron's and ulcerative colitis patients as well as patients with SLE. In some embodiments, a disease or condition disclosed herein can be detected in a sample based on a level of IL-7 in the sample.

A sample obtained from a subject can comprise tissue, cells, cell fragments, cell organelles, nucleic acids, genes, gene fragments, expression products, gene expression products, gene expression product fragments or any combination thereof. A sample can be heterogeneous or homogenous. A sample can comprise blood, urine, cerebrospinal fluid, seminal fluid, saliva, sputum, stool, lymph fluid, tissue, mucus, or any combination thereof. A sample can be a tissue-specific sample such as a sample obtained from a reproductive tissue (such as a sperm or an egg), thyroid, skin, heart, lung, kidney, breast, pancreas, liver, muscle, smooth muscle, bladder, gall bladder, colon, intestine, brain, esophagus, prostate, or any combination thereof. In some embodiments, a sample can be a cell-free sample.

As used herein, the term "cell-free" refers to the condition of the nucleic acid sequence as it appeared in the body before the sample is obtained from the body. For example, circulating cell-free nucleic acid sequences in a sample may have originated as cell-free nucleic acid sequences circulating in the bloodstream of the human body. In contrast, nucleic acid sequences that are extracted from a solid tissue, such as a biopsy, are generally not considered to be "cell-free." In some cases, cell-free DNA may comprise fetal DNA, maternal DNA, or a combination thereof. In some cases, cell-free DNA may comprise DNA fragments released into a blood plasma. In some cases, cell-free DNA may comprise circulating DNA indicative of a tissue origin, a disease or a condition. A cell-free nucleic acid sequence may be isolated from a blood sample. A cell-free nucleic acid sequence may be isolated from a plasma sample.

A sample may be obtained from a subject by another individual or entity, such as a healthcare (or medical) professional or robot. A medical professional can include a physician, nurse, medical technician or other. In some cases, a physician may be a specialist, such as an oncologist, surgeon, or endocrinologist. A medical technician may be a specialist, such as a cytologist, phlebotomist, radiologist, pulmonologist or others. A medical professional may obtain a sample from a subject for testing or refer the subject to a testing center or laboratory for the submission of the sample. The medical professional may indicate to the testing center or laboratory the appropriate test or assay to perform on the sample, such as methods of the present disclosure including determining gene sequence data, gene expression levels, sequence variant data, or any combination thereof. In some cases, a medical professional need not be involved in the initial diagnosis of a condition or a disease or the initial sample acquisition. An individual, such as the subject, may alternatively obtain a sample through the use of an over the counter kit. The kit may contain collection unit or device for obtaining the sample as described herein, a storage unit for storing the sample ahead of sample analysis, and instructions for use of the kit.

Kits

A kit-of-parts comprising a pharmaceutical composition together with instructions for use is further provided. For convenience, the kit-of-parts may comprise reagents in predetermined amounts with instructions for use.

In some embodiments, disclosed herein are kids comprising an IL-7 binding protein disclosed herein. In some embodiments, a kit can be a diagnostic kit. In some embodiments, a kit comprises an IL-7 binding protein disclosed herein and instructions for use. In some embodiments, a kit comprises means for measuring IL-7 level in a sample and instructions for use. A kit may provide a unit or device for obtaining a sample from a subject (e.g., a device with a needle coupled to an aspirator). A kit may include a plurality of syringes, ampules, foil packets, or blister packs, each containing a single unit dose of a kit component described herein. Containers of a kit may be airtight, waterproof (e.g., impermeable to changes in moisture or evaporation), and/or light-tight. A kit may include a device suitable for administration of the component, e.g., a syringe, inhalant, pipette, forceps, measured spoon, dropper (e.g., eye dropper), swab (e.g., a cotton swab or wooden swab), or any such delivery device. In some embodiments, the device may be a medical implant device, e.g., packaged for surgical insertion. A kit disclosed herein may comprise one or more reagents or instruments which enable the method to be carried out. In some embodiments, reagents or instruments include one or more of the following: suitable buffer(s) (aqueous solutions) a support comprising wells on which quantitative reactions can be done. A kit may be a specific kit for a specific tissue sample. Further, a kit disclosed herein may comprise a control.

In addition to the above components, instructions for use may be provided in a kit. These instructions may be present in the kit in a variety of forms, such as printed information on a suitable medium or substrate (e.g., a piece or pieces of paper on which the information is printed), in the packaging of the kit, in a package insert, etc. In some embodiments, instructions for use can be provided on a computer readable medium (e.g., jump/thumb drive, CD, etc.), on which the information has been recorded or at a website address which may be used via the internet to access the information at a website.

Devices

Another aspect of the disclosure provides a pre-filled syringe or autoinjector device, comprising an IL-7 binding protein or a composition described herein. In some embodiments, a composition stored in a container, pre-filled syringe, injector or autoinjector device contains an IL-7 binding protein disclosed herein.

Arrays

Disclosed herein are supports comprising an IL-7 binding protein disclosed herein. A support can be a solid support. A support may take a variety of configurations ranging from simple to complex, depending on the intended use of the support. A support can have an overall slide or plate configuration, such as a rectangular or disc configuration. A standard microplate configuration can be used. In some embodiments, the surface may be smooth or substantially planar, or have irregularities, such as depressions or elevations. In some embodiments, a support may have a rectangular cross-sectional shape, having a length of from about 10-200 mm, 40-150 mm, or 75-125 mm; a width of from about 10-200 mm, 20-120 mm, or 25-80 mm, and a thickness of from about 0.01-5.0 mm, 0.1-2 mm, or 0.2 to 1 mm.

In some embodiments, a support can be organic or inorganic; may be metal (e.g., copper or silver) or non-metal; may be a polymer or nonpolymer; may be conducting, semiconducting or nonconducting (insulating); may be reflecting or nonreflecting; may be porous or nonporous; etc. A support as described herein can be formed of any suitable material, including metals, metal oxides, semiconductors, polymers (particularly organic polymers in any suitable form including woven, nonwoven, molded, extruded, cast, etc.), silicon, silicon oxide, and composites thereof. A support can be an array. In some embodiments, a support comprises an array. An array can comprise an ordered spatial arrangement of two or more discrete regions. An array can comprise IL-7 binding proteins located at known or unknown discrete regions. Row and column arrangements of arrays can be selected due to the relative simplicity in making such arrangements. The spatial arrangement can, however, be essentially any form selected by the user, and optionally, in a pattern. Areas of an array may be any convenient shape, including circular, ellipsoid, oval, annular, or some other analogously curved shape, where the shape may, in certain embodiments, be a result of the particular method employed to produce the array.

In some embodiments, a support can be planar. In some instances, a support can be spherical. In some instances, a support can be a bead. In some instances, a support can be magnetic. In some embodiments, a magnetic support can comprise magnetite, maghemitite, FePt, SrFe, iron, cobalt, nickel, chromium dioxide, ferrites, or mixtures thereof. In some embodiments, a support can be nonmagnetic. In some embodiments, the nonmagnetic support can comprise a polymer, metal, glass, alloy, mineral, or mixture thereof. In some instances, a nonmagnetic material can be a coating around a magnetic support. In some instances, a magnetic material may be distributed in the continuous phase of a magnetic material. In some embodiments, the support comprises magnetic and nonmagnetic materials. In some instances, a support can comprise a combination of a magnetic material and a nonmagnetic material. In some embodiments, an IL-7 binding protein disclosed herein is directly or indirectly associated with a support disclosed herein.

Computer Control Systems

The present disclosure provides computer control systems that are programmed to implement methods of the disclosure. In some embodiments, a computer system is programmed or otherwise configured to interface with an apparatus that is configured to detect IL-7 and/or binding of an IL-7 binding protein disclosed herein to moiety. The computer system can be an electronic device of a user or a computer system that is remotely located with respect to the electronic device. The electronic device can be a mobile electronic device.

In some embodiments, a computer system includes a central processing unit (CPU, also "processor" and "computer processor" herein, which can be a single core or multi core processor, or a plurality of processors for parallel processing. In some embodiments, a computer system also includes memory or memory location (e.g., random-access memory, read-only memory, flash memory), electronic storage unit (e.g., hard disk), communication interface (e.g., network adapter) for communicating with one or more other systems, and peripheral devices, such as cache, other memory, data storage and/or electronic display adapters. In some embodiments, the memory, storage unit, interface and peripheral devices are in communication with the CPU through a communication bus, such as a motherboard. In some embodiments, the storage unit can be a data storage unit (or data repository) for storing data. In some embodiments, the computer system is operatively coupled to a computer network ("network") with the aid of the communication interface. In some embodiments, the network can be the Internet, an internet and/or extranet, or an intranet and/or extranet that is in communication with the Internet. In some embodiments, the network is a telecommunication and/or data network. The network can include one or more computer servers, which can enable distributed computing, such as cloud computing. In some embodiments, the network, in some cases with the aid of the computer system can implement a peer-to-peer network, which may enable devices coupled to the computer system to behave as a client or a server. In some embodiments, the CPU executes a sequence of machine-readable instructions, which can be embodied in a program or software. The instructions may be stored in a memory location, such as the memory. The instructions can be directed to the CPU, which can subsequently program or otherwise configure the CPU to implement methods of the present disclosure. Examples of operations performed by the CPU can include fetch, decode, execute, and writeback. In some embodiments, the CPU can be part of a circuit, such as an integrated circuit. One or more other components of the system can be included in the circuit. In some cases, the circuit is an application specific integrated circuit (ASIC). In some embodiments, the storage unit can store files, such as drivers, libraries and saved programs. The storage unit can store user data, e.g., user preferences and user programs. The computer system in some cases can include one or more additional data storage units that are external to the computer system, such as located on a remote server that is in communication with the computer system through an intranet or the Internet. In some embodiments, the computer system communicates with one or more remote computer systems through the network. For instance, the computer system can communicate with a remote computer system of a user. Examples of remote computer systems include personal computers (e.g., portable PC), slate or tablet PC's telephones, Smart phones, or personal digital assistants. The user can access the computer system via the network.

Methods as described herein can be implemented by way of machine (e.g., computer processor) executable code stored on an electronic storage location of the computer system, such as, for example, on the memory or electronic storage unit. The machine executable or machine-readable code can be provided in the form of software. During use, the code can be executed by the processor. In some cases, the code can be retrieved from the storage unit and stored on the memory for ready access by the processor. In some situations, the electronic storage unit can be precluded, and machine-executable instructions are stored on memory. In some embodiments, the code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

A machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

In some embodiments, a computer system disclosed herein can include or be in communication with an electronic display that comprises a user interface (UI) for providing, for example, one or more results (immediate results or archived results from a previous experiment), one or more user inputs, reference values from a library or database, or a combination thereof. Examples of UIs include, without limitation, a graphical user interface (GUI) and web-based user interface.

Further, methods and systems of the present disclosure can be implemented by way of one or more algorithms. An algorithm can be implemented by way of software upon execution by the central processing unit. The algorithm can, for example, determine optimized conditions via supervised learning to optimize conditions such as a buffer type, a buffer concentration, a temperature, an incubation period, thresholds, diagnostic/prognostic indications for methods disclosed herein.

EXAMPLES

Example 1: DRSPAI-L7B In Cynomolgus Monkey

The study was set forth to evaluate DRSPAI-L7B in cynomolgus monkey. Part 1, three single dose IV injections at 0.1, 1 and 10 mg/kg were evaluated. In part 2, repeat dosing (four SC injections) of 30 mg/kg in the vehicle control animals from part 1. Blood samples were collected for assessment of drug PK as well as free and total IL-7 levels and pharmacodynamic activity of DRSPAI-L7B through the measurement of STAT5 phosphorylation.

Total Antibody Levels

Total antibody levels were determined using a generic antigen capture and detection method on the GYROLAB. The maximum detected peak serum concentration ($C_{max}$) and the time at which it was observed ($T_{max}$) were determined by inspection of the obtained data. In addition, the AUC, total serum clearance (CL); volume of distribution at steady-state (Vss) and terminal half-life (t½) were calculated using a non-compartmental PK model. (Table 3)

TABLE 3

Mean PK parameters for DRSPAI-L7B (IV administration) for single ascending dose part 1 and repeat dose part 2

| Part 1 | | | | | |
| --- | --- | --- | --- | --- | --- |
| Dose (mg/kg) | $C_{max}$ (ug/mL) | $AUC_{inf}$ (hr*ug/mL) | Half-Life (hr) | CL (mL/hr/Kg) | $V_{ss}$ (mL/Kg) |
| 0.1 | 3.12 (2.80-3.55) | 721 (710-733) | 350 (270-410) | 0.14 (0.14-0.14) | 82 (71-90) |
| 1.0 | 37.2 (27.8-48.4) | 8250 (7520-9060) | 470 (350-560) | 0.12 (0.11-0.13) | 71 (58-80) |
| 10.0 | 307 (262-337) | 93100 (76800-112000) | 420 (340-490) | 0.11 (0.09-0.13) | 66 (58-73) |

| Part 2 (30 mg/kg) | | |
| --- | --- | --- |
| Period | $C_{max}$ (ug/mL) | $AUC_{i0-168}$ (hr*ug/mL) |
| First dose | 320 (258-398) | 41600 (32700-47300) |
| Second dose (168 h post dose) | 463 (407-516) | N/A |
| Third dose (168 h post dose) | 556 (490-602) | N/A |
| Fourth dose | 911 (688-1270) | 119000 (94100-169000) |

No target mediated rug disposition (TMDD) was observed and as the dose increases from 0.1 to 10 mg/kg the increase in serum Cmax and AUC are dose proportional. DRSPAI-L7B is cleared slowly with a mean half-life of approximately 17±3.9 days and on repeat dosing, a 2.8-fold accumulation of drug. The data is presented in FIG. 1A, FIG. 1B, and FIG. 1C.

An acid dissociation bridging assay was used to assess the presence of anti-drug antibodies (ADA) using DRSPAI-L7B to capture. No ADA were detected during either part 1 or part 2 of the study.

A further study was carried out to determine the PK and PD of DRSPAI-L7B in cynomolgus monkeys following subcutaneous (SC) dosing. Four single dose IV injections at 0.1, 1, 3 and 10 mg/kg were evaluated. The doses were administered by SC injection once on Day 1.

The systemic exposure to DRSPAI-L7B was determined by calculating the area under the serum concentration time curve (AUC) from the start of dosing to the last quantifiable time point ($AUC_{0-t}$) using the linear up/log down trapezoidal method. The maximum observed peak serum concentration (Cmax) and the time at which it was observed (Tmax) were determined by PK SUBMIT.

TABLE 4

Serum PK parameters for DRSPAI-L7B (SC administration)

| | | Dose of DRSPAI-L7B (mg/kg) | | | |
| --- | --- | --- | --- | --- | --- |
| Parameter | | 0.1 | 1 | 3 | 10 |
| $AUC_{0-t}$ (μg · h/ml) | Mean | 943 | 6960 | 18900 | 60200 |
| | Min | 687 | 3870 | 17100 | 52700 |
| | Max | 1120 | 9130 | 21300 | 69700 |
| $C_{max}$ (μg/ml) | Mean | 2.01 | 18.1 | 34.2 | 119 |
| | Min | 1.76 | 16.9 | 29.5 | 108 |
| | Max | 2.21 | 19.0 | 39.1 | 128 |

TABLE 4-continued

Serum PK parameters for DRSPAI-L7B (SC administration)

| Parameter | | Dose of DRSPAI-L7B (mg/kg) | | | |
|---|---|---|---|---|---|
| | | 0.1 | 1 | 3 | 10 |
| $T_{max}$ (h) | Mean | 168 | 96 | 96 | 96 |
| | Min | 96 | 48 | 96 | 96 |
| | Max | 168 | 96 | 96 | 168 |

At the highest dose, 10 mg/kg, the gender averaged mean Cmax was 119 μg/mL (range from 108 to 128 μg/mL), and mean $AUC_{0-t}$ 60200 μg.h/mL (range from 52700 to 69700 μg.h/mL).

There were dose-dependent increases in total IL-7 levels at all dose levels, demonstrating target engagement of DRSPAI-L7B. There was also dose-dependent inhibition of IL-7 induced STAT phosphorylation in total Th and Tc lymphocytes at (1 mg/kg and a dose dependent decrease in Bcl-2 expression in Th lymphocytes at $M^3$ mg/kg.

Low levels of anti-DRSPAI-171B antibodies were detected in two of three monkeys given 1.0 mg/kg. In one male this resulted in reduced target engagement and a lower AUC.

Example 2: DRSPAI-L7B Binding Affinity To IL-7

The kinetics and affinities for binding of DRSPAI-7 r to human and cynomolgus monkey IL-7 were assessed at 25° C. and 37° C. by surface plasmon resonance (SPR) using a Biacore 8K instrument. The affinity of DRSPAI-L7B for human IL-7 was approximately 34 pM at 25° C. and 67 pM at 37° C. (Table 5). The affinity of DRSPAI-L7B for cynomolgus IL-7 was approximately 53 pM at 25° C. and 75 pM at 37° C. (Table 5).

TABLE 5

Binding kinetics and affinities of DRSPAI-L7B to human and cynomolgus IL-7

| Analyte | average ka (1/Ms) | average kd (1/s) | Average KD (pM) | SD (KD, pM) |
|---|---|---|---|---|
| DRSPAI-L7B at 25° C. | | | | |
| hIL-7 | 6.49E+06 | 2.06E−04 | 31 | 5 |
| hIL-7 | 4.65E+06 | 1.58E−04 | 34 | 7 |
| cynoIL-7 | 3.17E+06 | 1.70E−04 | 53 | 6 |
| DRSPAI-L7B at 37° C. | | | | |
| hIL-7 | 8.28E+06 | 5.68E−04 | 69 | 5 |
| hIL-7 | 1.47E+07 | 6.78E−04 | 46 | 8 |
| hIL-7 | 1.10E+07 | 8.26E−04 | 75 | 12 |
| hIL-7 | 5.90E+06 | 5.15E−04 | 87 | 3 |
| hIL-7: geometric mean KD (pM)* | | | 67.4 (58.4, 76.3) | |
| cynoIL-7 | 6.17E+06 | 4.62E−04 | 73 | 5 |

*geometric mean KD derived from all experiments (pM, with 85% confidence interval)

Example 3: Inhibition of IL-7 Signaling-Functional Assay

All human samples were obtained with patient informed consent in accordance with ICH GCP under a protocol approved by a national, regional or investigational center ethics committee or an Institutional Review Board (IRB) approved protocol. Disease PBMCs were supplied by an approved external human tissue supplier. PBMCs were stored frozen at −80° C. until use.

Healthy volunteer blood was provided by a Blood Donation Unit: Blood was withdrawn by venepuncture and transferred into a pot or blood bag containing sodium heparin (1 U/mL). The blood was collected and used within 1 hour, either for whole blood assays or for PBMC isolation. Different donors were used for each experiment. Cells were thawed by removing from −80° C. storage and immediately placed into a water bath at 37° C. After transferring cell suspension to a 15 mL centrifuge tube warm medium (RPMI+10% heat-inactivated FCS, 1% penicillin/streptomycin, and 1% GlutaMax) was added very slowly to decrease DMSO concentration gradually. Once volume was increased to 10 mL the cells were centrifuged and washed once more before counting and resuspending in an appropriate volume of assay medium to yield $5\times10^6$ cells per 1 mL.

All antibodies were aliquoted on arrival for long term storage at −80° C. For experimentation, antibody aliquots were thawed and stored at 4° C. for no longer than 8 weeks.

| Reagent | Supplier |
|---|---|
| AIM V Medium | Gibco |
| Recombinant human IL-7 | R&D Systems |
| BD Phosflow ™ Lyse/Fix Buffer 5x | BD Bioscience |
| BD Phosflow ™ Perm Buffer III | BD Biosciences |
| Flow cytometry staining buffer | eBioscience |
| FcR Blocking reagent | Miltenyi Biotec |
| BD Phosflow ™ PE Mouse anti-STAT5 (pY694) | BD Bioscience |
| Mouse anti-human CD8 FITC (clone: SKI) | Biolegend |
| Mouse anti-human CD4 PerCP/Cy5.5 (clone: RPA-T4) | Biolegend |
| Mouse anti-human CD3 BV510 (clone: SK7) | Biolegend |
| Anti-mouse Ig, κ/Negative Control Compensation Particles Set | BD Bioscience |
| BD FACSDiva CS&T Research Beads | BD Bioscience |

All antibody treatments and rhIL-7 stimulations were made up at 4× final assay concentration (F.A.C.) in culture medium before mixing 1:1 and incubating at room temperature for 5 minutes. In the absence of either antibody or IL-7 stimulus, culture medium was added.

For whole blood: 100 μL of the antibody:IL-7 mixture was aliquoted into FACS tubes before adding 100 μL of whole blood. Tubes were mixed gently by vortexing and incubated at 37° C. in a humidified incubator for 20 minutes. At the end of the stimulation period 2.5 mL pre-warmed PHOSFLOW lysis buffer (1×) was added and the samples were incubated for a further 10 minutes at 37° C. 2 mL PBS was added to the suspension and tubes were centrifuged to pellet the cells (300× g, 5 minutes at room temperature). Supernatant was discarded and cells were washed twice more in PBS. Following the final wash, cells were resuspended in 500 μL Perm Buffer III (pre-cooled to −20° C.) and vortexed to mix. Tubes were incubated on ice for 30 minutes before washing once in 3 mL PBS. Cells were resuspended in 100 μL PBS and transferred to 96-well, round bottom culture plate for staining.

For PBMCs treatments: 50 μL of the antibody:IL-7 mixture was added to each well of a 96-well, round bottom tissue culture plate. 50 μL PBMC suspension was added to each treatment well ($2.5\times10^5$ cells/well). Plates were mixed gently on a rotary plate shaker before incubating at 37° C. in a humidified incubator for 20 minutes. At the end of the stimulation period 250 μL pre-warmed PHOSFLOW lysis buffer (1×) was added and the samples were incubated for a further 10 minutes at 37° C. Following fixation, cells were pelleted by centrifugation (300×g, 5 minutes at room temperature) and washed twice in 200 μL PBS. Cell pellets were resuspended in 100 μL Perm Buffer III (pre-cooled to −20° C.) and pipetted up and down to mix. Cells were incubated on ice for 30 minutes before washing once in 200 μL PBS and resuspending in PBS.

For all samples: Following permeabilization, plates were centrifuged (300× g, 5 minutes at room temperature) and cell pellets were resuspended in 25 μL FcR blocking reagent diluted 1:5 in 3% BSA in PBS. Cells were incubated for 10 minutes at room temperature before adding 2.5 μL anti-CD3 (BV510), 2.5 μL anti-CD4 (PerCP/Cy5.5), 2.5 anti-CD8 (FITC), 7.5 μL anti-pSTAT5 (PE) and 35 μL flow cytometry staining buffer (50 μL total per sample). Where a stain was excluded for controls, the equivalent volume of staining buffer was added instead. Plates were mixed briefly on a rotary plate shaker and incubated on ice for 30 minutes protected from light. Cells were washed in 200 μL staining buffer and resuspended in 200 μL staining buffer for analysis on the same day on the FACS Canto II.

The performance of the instrument was checked using the Cytometer Set-up and Tracking (CST) Beads. This is a QC check for the instrument, sets the baselines and optimizes the voltages for each laser prior to use. The results of the calibration are stored within the CST software on the instrument.

Compensation for the instrument was performed using anti-mouse $IgG_{,K}$/negative control compensation beads in accordance with the manufacturer's instructions. The relevant antibodies used to stain the cells during the experiment were used to label the appropriate compensation bead type.

Compensation for the experiments were performed using the appropriately labelled beads with the automatic compensation facility available within the FACS Diva software. After analysis of the compensation samples the appropriate compensation settings were calculated and applied to each experimental staining panel. pSTAT5 FACS analysis: Acquired cells in a FSC-A vs FSC-H plot to exclude doublets. Single cells were acquired into a FSC-A vs SSC-A plot and gated around the live lymphocytes. These were acquired into AmCyan vs FSC-A plot and gated around the CD3+ population. A PerCP-Cy5.5 vs FITC plot was generated on $CD3^+$ to identify $CD4^+$ and $CD8^+$ populations. For pSTAT5 a histogram for PE fluorescence was created for each subset. Positive gates were set based on the unstimulated samples and the percent PE positive statistic was used for data analysis.

Data were analyzed using FlowJo software (version 10) and results were generated in Microsoft Excel (2010) spreadsheet format using the Batch Analysis facility within the FlowJo software. The cell populations were tabulated in an Excel spreadsheet as % of parent. This was converted into a percent response by normalizing to the unstimulated control or a percent inhibition by normalizing to the unstimulated control and subtracting this value from 100 (theoretical maximal percent response).

Where concentration response graphs have been generated, individual donor data were fitted with a non-linear logistic curve fit regression and the average (mean and median), range, SD and SEM of the $IC_{50}$ from all donors was calculated in GraphPad Prism (version 6). Where statistical testing was carried out, a 2-way ANOVA with Sidak's correction for multiple comparison was applied. A p value of <0.05 was considered as statistically significant. * denotes p<0.05;  ps≤0.01; * p≤0.001; and **** ps≤0.0001.

In a whole blood assay, STAT5 phosphorylation was assessed in $CD4^+$ T cells by flow cytometry after 20 minutes stimulation with 1 ng/ml recombinant human IL-7 (rhIL-7; 58 pM). As shown in FIG. 2A and Table 6, DRSPAI-L7B prevented IL-7 from signaling through STAT5 in a concentration-dependent manner with a median $IC_{50}$ of 34 pM (5.1 ng/mL). A1290 prevented IL-7 signalling through STAT5 in a concentration-dependent manner with a median $IC_{50}$ of 18 pM (0.00275 μg/ml). A1291 prevented IL-7 signalling through STAT5 in a concentration-dependent manner with a median $IC_{50}$ of 16 pM (0.00246 μg/ml). A1294 prevented IL-7 signalling through STAT5 in a concentration-dependent manner with a median $IC_{50}$ of 76 pM (0.0114 μg/ml). Immortalized T lymphoblast CCRF-CEM cells were stimulated with 34 μg/mL (2 pM) recombinant human IL-7 (rhIL-7) in the presence or absence of DRSPAI-L7B. STAT5 phosphorylation was assessed by MSD on cell lysates. DRSPAI-L7B potently blocked IL-7-induced pSTAT5 (Table 6; $IC_{50}$<1 pM).

TABLE 6

Summary of potency of DRSPAI-L7B in functional assays

| Assay | IL-7 | | DRSPAI-L7B $IC_{50}$ | |
|---|---|---|---|---|
| | ng/ml | pM | ng/ml | pM |
| pSTAT5 in CCRF-CEM cells | 0.034 | 2 | <0.15 | <1 |
| pSTAT5 in whole blood | 1 | 58.8 | 5.1 | 34 |
| $T_{eff}$ and $T_{mem}$ proliferation ($CD4^+$)§ | 20 | 1,176 | 78 | 520 |
| $T_{eff}$ and $T_{mem}$ proliferation ($CD4^+$)§ | 10 | 588 | 79.5 | 530 |
| IFN-γ production by PBMC | 10 | 588 | 29.4 | 195.8 |
| IL-17 production by $T_{mem}$ | 20 | 1,176 | 40.5 | 270 |

Figure 2C:
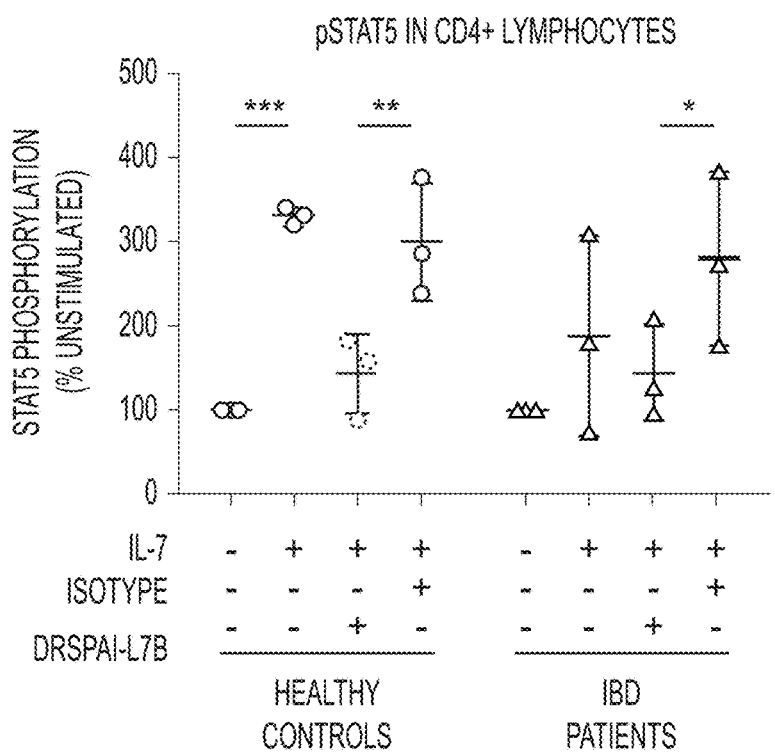
Figure 2D:
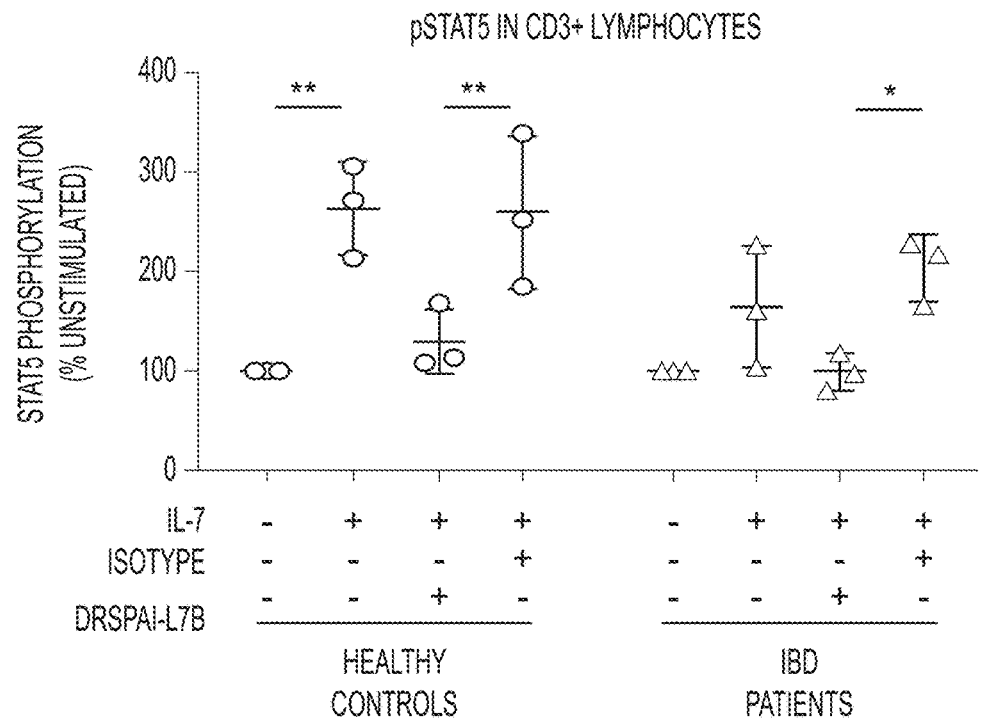

§Assays were performed using EC80 stimulation with IL-7 determined for each batch of cells IL-7 Induced STAT5 Phosphorylation in Healthy and Disease T Cells PBMCs from healthy donors or IBD patients (two Crohn's disease and one ulcerative colitis) were stimulated with rhIL-7 in the presence of DRSPAI-L7B or anti-RSV antibody (isotype control). Stimulated cells were fixed and STAT5 phosphorylation in $CD8^+$ (FIG. 2B), $CD4^+$ (FIG. 2C), and CD3' (FIG. 2D) T cells was assessed by flow cytometry. Data is shown as pSTAT5 increase relative to unstimulated condition, mean±SD, n=3. * p<0.05,  p≤0.01, * p:0.001, matched 2-way ANOVA with Sidak's multiple comparisons correction. FIG. 2B, FIG. 2C and FIG. 2D.

Example 4: Dynamic Light Scattering Assay

Dynamic Light Scattering (DLS) analysis was carried out on DRSPAI-L7B, A1290, A1291 and A1294 to characterize high order aggregate species and sample heterogeneity.

Each of the respective antibodies was concentrated to >10 mg/ml and buffer exchanged via dialysis into 50 mM sodium phosphate pH 7.5 or 50 mM sodium acetate pH 5.0 buffers followed by normalization to 10 mg/ml and filtration using a 0.22 μm syringe filter. Post filtration all the samples were stressed at a target concentration of 10 mg/ml for 2 weeks at 40° C. Samples were evaluated following incubation under stressed and unstressed conditions in the two buffers. 100 μl samples were run in triplicate at 25° C. on a Wyatt DynaPro DLS Plate reader using 96 well Corning Costar 3635 plates sealed with Corning 6575 seals.

The data was analysed using DYNAMICS v7.1.9 software. The data was distributed into the following peaks: Peak 1=0.1-1 nm, Peak 2=1-10 nm, Peak 3=10-100 nm, Peak 4=100-1000 nm, Peak 5=1000-10000 nm. The data was filtered using the following criteria: amplitude must be between 0 and 1, baseline limit 1±0.01 and sum of all squared (SOS) must be less than 100. An Rh of >8 nm and average % mass at Peak2<98% was associated with a severe aggregation risk.

A1290, A1291 and A1294 showed severe aggregation risks, all exhibiting hydrodynamic radius (Rh) values of >8 nm. DRSPAI-L7B had an Rh value of <8 nm and did not, thus, exhibit such aggregation risk.

| | |
|---|---|
| γc | Common gamma chain |
| BV510 | Brilliant Violet 510 |
| CD(X) | Cluster of differentiation (X) |
| CHO | Chinese hamster ovary cells |
| CST | Cytometer set-up and tracking |
| DMSO | Dimethylsulphoxide |
| F.A.C | Final assay concentration |
| FACS | Fluorescence-activated cell sorting |
| FcR | Fe receptor |
| FCS | Foetal calf serum |
| FITC | Fluorescem isothiocyanate |
| FSC-(A/H/W) | Forward scatter - (area/height/width) |
| HEK | Human embryonic kidney cells |
| IBD | Inflammatory bowel disease |
| $IC_{50}$ | Inhibitory concentration 50% |
| IL-7 | Interleukin 7 |
| IL-7Rα | Interleukin 7 receptor alpha |
| JAK | Janus kinase |
| (e)LNB | (Electronic) laboratory notebook |
| mAb | Monoclonal antibody |
| PBMCs | Peripheral blood mononuclear cells |
| PBS | Phosphate buffered saline |
| PE | Phycoerythrin |
| PerCP/Cy5.5 | Peridinin chlorophyll protein complex/Cyanine 5.5 |
| SD | Standard deviation |
| SEM | Standard error of the mean |
| SSC-(A/H/W) | Side scatter - (area/height/width) |
| pSTAT5 | Phosphorylated STAT5 |
| rhIL-7 | Recombinant human IL-7 |
| RPMI | Roswell Park Memorial Institute medium |
| STAT5 | Signal transducer and activator of transcription 5 |

Example 5: Impact of DRSPAI-L78 On Cytokine Production In Human PBMC

DRSPAI-L7B was used to interrogate the role that IL-7 plays in Th1 and Th17 function and differentiation. The effect of DRSPAI-L7B on cytokine secretion from healthy PBMCs stimulated with IL-7 in the presence of a CD3 agonistic antibody was assessed.

Healthy volunteer blood was provided by a Blood Donation Unit: Blood was withdrawn by venepuncture and transferred into a pot or blood bag containing sodium heparin (1 U/mL). The blood was collected and used for PBMC isolation.

The blood was diluted 2× with PBS, layered onto 15 mL ficoll in Accuspin tubes and centrifuged at 800 rcf for 20 minutes without break. The plasma was removed carefully with a pipette and the layer containing the PBMCs was carefully transferred to a 50 mL tube. The PBMCs were washed twice in 50 mL PBS (250 rcf, 10 minutes) and then resuspended in 50 mL RPMI+10% FCS+L-glutamine and counted using Vi-cell XR.

PBMCs were resuspended in culture media at $5×10^6$ cells/mL. Antibody dilutions of anti-RSV antibody (isotype control) and DRSPAI-L7B were prepared at 2.5× the required final concentration in culture media. Equal volumes of cell suspension and antibody dilutions (150 μL) were mixed and incubated for 30 min at room temperature. IL-7 was prepared at 5× the final concentration in culture medium and 20 μL added in the required wells of a 96-well U bottom polystyrene plate, which had been pre-coated with 10 μg/mL anti-CD3 at 4° C. overnight. Culture medium was added in all remaining wells. 80 μL of the mixed cell suspension/antibody dilutions (2×106 cells/well) were added to each well of the 96-well plate and left to incubate for 48 hrs at 37° C., 5% C02.

After 48 hrs the plate was centrifuged at 300 rcf for 5 minutes and the supernatants were removed without disturbing the pellets and transferred to a new 96-well U-bottom plate. Supernatants were either used for ELISA/MSD immediately after harvesting or stored at −80° C. until further use.

Anti-RSV IgG1 was at stock concentration of 2.8 mg/mL. Thawed and diluted to the appropriate concentration on day of use. DRSPAI-L7B stock concentration was 11.33 mg/mL. Thawed and diluted to the appropriate concentration on day of use. Recombinant Human IL-7 was purchased from R&D systems. The lyophilized protein was resuspended to 254 g/mL in sterile PBS+0.1% bovine serum albumin and 50 μL aliquots stored at −20° C. Thawed and diluted to the appropriate concentration on day of use. Anti-CD3 clone HIT3a. Stock was 1 mg/mL. Diluted to the appropriate concentration on day of use.

| Reagent | Company |
|---|---|
| RPMI | Gibco |
| FCS | In house |
| L-glutamine | In house |
| 96-well flat bottom type TC treated polystyrene plates | Costar |
| 96-well U bottom type TC treated polystyrene plates | Greiner |
| DPBS | Gibco |
| Aluminium Foil Lids | Beckman Coulter |
| Plate sealers | Greiner bio-one |
| U-plex Biomarker Group 1 (Human) | Mesoscale Discovery |

ECL signals were derived from the MSD instrument and converted to concentrations using the standard curve for each analyte. For graphs in which the data is normalized, the average of anti-CD3' IL-7 samples was set at 100% and all other values were normalized to that. The antibody concentrations were log transformed and plotted against cytokine concentrations. The no IL-7 (anti-CD3 only) samples are shown in each graph for comparison. For curve fitting, the following nonlinear fit from Graphpad Prism was used: log(inhibitor) vs. response (three parameters) and $IC_{50}$ values were calculated by Graphpad Prism.

DRSPAI-L7B inhibited IFN-γ (FIG. 3A) and IL-10 (FIG. 3B) secretion in a concentration-dependent manner (IFN-γ mean $IC_{50}$=195.8±101 pM; IL-10 mean $IC_{50}$=207.2±86 pM). Data represent the mean of n=6 independent donors±SEM, assessed in 3 independent experiments. FIG. 3C, FIG. 3D, FIG. 3E, FIG. 3F, FIG. 3G illustrates inhibition of IL-2 by DRSPAI-L7B in the presence of rhIL-7 and anti-CD3. There was an increase in IL-2 production following IL-7 stimulation in 5 donors. This increase was inhibited fully by DRSPAI-L7B.

Example 6: DRSPAI-L7B Inhibits Cytokine Production By Memory T Cells

To accurately determine the role of IL-7 in Th17 cell function and differentiation, a 'poised Th17' assay was used to profile the secretion of Th17-associated cytokines. $T_{mem}$ cells were isolated from healthy donors and incubated with IL-7 in the presence of DRSPAI-L7B.

Whole human blood was collected from donors in the Blood Donation Unit (BDU).Typically, 200 mL was collected by venepuncture per donor and an anti-coagulant, citrate-dextrose solution (ACD, Sigma, Cat #C3821) was added immediately to each sample. ACD was added at 15% (e.g. 30 mL ACD added to 200 mL blood). Within 2 hours of collection, and using a microbiological safety cabinet, the blood was dispensed evenly into pre-filled LEUCOSEP tubes (Greiner, Cat #227288) at 30 mL (max) per tube. The blood was centrifuged for 15 minutes at 800× g at room temperature in a swing bucket rotor with no brake applied. The PBMCs were washed in PBS (500× g, 10 minutes) and then resuspended in 10 mL PBS and counted using the NucleoCounter. The cells were centrifuged again at 500× g and the cell pellet was re-suspended in FACS buffer at a concentration of 5×10⁶cells/mL.

Human CD4⁺ memory T cells ($T_{mem}$) EasySep enrichment cocktail was added at 50 μL/mL to the cell suspension. The cells were incubated at room temperature for 10 minutes after which the EasySep magnetic particles were added at 50 μL/mL. The suspension was again incubated at room temperature for 10 minutes after which the cell suspension was placed in an EasySep magnet for 10 minutes. The cell suspension was then transferred to a fresh tube whilst still placed within the magnet to ensure a negative selection. The cells were centrifuged at 500×g for 10 minutes and resuspended in cell culture media. The cell count was determined using the NucleoCounter.

The cells were rested at 37° C. and 5% $CO_2$ overnight in culture media. The next day the cells were centrifuged and resuspended in assay media at a concentration of 2.5×10⁵ cells/mL. Recombinant hIL-7 was added to the cells at a final concentration of 20 ng/mL. The cells were then incubated in the presence of DRSPAI-L7B for 4 days at 37° C. and 5% $CO_2$ after which they were stimulated with 10 nM PMA and 1 μM Ionomycin for 16 hours at 37° C. and 5% $CO_2$.

Detection of IL-17 from the Supernatants Using MSD

After 16 hours of PMA and ionomycin stimulation, the cells were centrifuged and 40 μL of the supernatants were transferred to the MSD plates which were pre-blocked with 0.5% of Blocker B. These MSD plates were coated with an anti-IL-17A capture antibody. The samples were incubated for 2 hours at room temperature whilst shaking after which the plates were washed with PBS and 0.05% Tween-20. 10 μL of the IL-17 specific detection antibody labelled with the MSD SULFO-TAG reagent was then added and the samples were incubated for a further 2 hours at room temperature whilst shaking. The plate was washed again three times in PBS and 0.05% Tween-20 and 2× Read Buffer T was added to the samples.

The plate was read on the Sector Imager.

Detection of Other Cytokines

A U-Plex MSD Kit was designed to enable investigation of the effect of DRSPAI-L7B on the secretion of IL-6, IL-10, IFN-γ, TNF-α and CCL3. The MSD U-Plex plates were prepared by coating the plate with linker coupled capture antibodies. Each capture antibody was biotinylated and had a unique linker assigned to it. The supernatants were diluted 1 in 100 and transferred to the MSD plates. The samples were incubated for 1 hour at room temperature whilst shaking after which the plates were washed with PBS and 0.05% Tween-20. 50 μL of the specific detection antibodies labelled with the MSD SULFO-TAG reagent was then added and the samples were incubated for a further hour at room temperature whilst shaking. The plate was washed again three times in PBS and 0.05% Tween-20 and 2× Read Buffer T was added to the samples. The plate was read on the Sector Imager.

DRSPAI-L7B antibody was produced at a stock concentration of 11.33 mg/mL in 20 mM Histidine, 180 mM Trehalose, 40 mM Arginine, 8 mM Methionine, 0.05 mM EDTA, pH 6.0. The Antibody was diluted to a concentration of 20 μg/mL in assay media. A 1 in 3 serial dilution was then carried out in assay media to generate a 10 point dose response curve. The dilutions were transferred to the assay plates ensuring that the highest final assay concentration of the antibody was 10 μg/mL.

BRL-54319MM (Rapamycin) was used as the positive control in the assay at 1 μM final assay concentration in assay media.

Recombinant Human IL-7 was resuspended to 25 Mg/mL in sterile PBS and 50 μL aliquots stored at −20° C. The aliquots were thawed and diluted to the appropriate concentration on day of use.

| Reagent | Company |
|---|---|
| Pre-Filled Leucosep Tubes | Greiner |
| Human IL-17 Base Kit | MSD |
| Easy50 EasySep Magnet | Stemcell |
| Phospho buffered saline, no Ca2+/Mg2+ (PBS) | Gibco |
| IMDM | Gibco |
| 96 well Costar round bottom polystyrene, sterile plates, with lid, clear | Costar |
| Heat Inactivated Fetal Bovine Serum | Hyclone |
| Xvivo15 | Lonza |
| Penstrep | Invitrogen |
| Easysep Human Memory CD4+ T-cell enrichment Kit | Stem cell |
| L-Glutamine | Invitrogen |
| MEM Non-Essential Amino Acids | Invitrogen |
| HEPES | Invitrogen |
| PMA-Phorbol 12-myristate 13-acetate | Sigma |
| Ionomycin | Sigma |
| Sodium Pyruvate | Invitrogen |
| U-plex Biomarker Group 1 (Human) Kit | Mesoscale Discovery |
| CellTiter-Glo | Promega |

FACS Buffer: sterile PBS containing 2% heat-inactivated FBS. Cell Culture Media: 450 mL IMDM, 50 mL FBS, 5 mL Penstrep, 5 mL L-Glutamine, 5 mL Non-essential Amino Acids and 5 mL Sodium Pyruvate. Assay Media: 500 mL Xvivo 15, 5 mL Penstrep, 5 mL L-glutamine, 5 mL HEPES and 5 mL Sodium Pyruvate.

All data was normalized to the mean of 8 high and 8 low control wells on each plate. A four-parameter curve fit of the following form was then applied.

$$y = \frac{a-d}{1+(x/c)^b} + d$$

Where a is the minimum, b is the Hill slope, c is the XC50 and d is the maximum. Data was presented as the mean $IC_{50}$ with the standard deviation of the mean of n experiments.

CD4⁺ $T_{mem}$ cells, isolated from healthy donor blood, were incubated with IL-7 in the presence of DRSPAI-L7B for 4 days after which they were spiked with PMA/ionomycin for 16 hours before harvest.

Cytokine secretion into the supernatant was assessed by MSD. DRSPAI-L7B treatment resulted in a concentration-dependent inhibition of IL-17 (FIG. 4A, $IC_{50}$=270±31.59 pM), TNFα (FIG. 4B, $IC_{50}$=127.1±89.83 pM), IL-6 (FIG. 4C, $IC_{50}$=202.07±99.64 pM), IL-10 (FIG. 4D, $IC_{50}$=197.48±148.91), INFγ (FIG. 4E, $IC_{50}$=157.98±89.55) and CCL3 (FIG. 4F, $IC_{50}$=163.83±85.96) secretion. Dose dependent inhibition was also observed for IL-6, IL-10, IFNγ, TNFα and CCL3. Inhibition of the production of these cytokines was expressed as a percentage of that achieved with Rapamycin (1 pM) positive control.

Example 7: T Cell Population Analysis

Given the central role of T cells in MS, T cell populations were analysed in PBMCs from RRMS, PPMS and SPMS patients.

All human samples were obtained with patient informed consent in accordance with ICH GCP under a protocol approved by a national, regional or investigational center ethics committee or an Institutional Review Board (IRB) approved protocol.

Healthy PBMCs were isolated from BDU blood and stored frozen in liquid nitrogen until used. Disease PBMCs were supplied by an approved external human tissue supplier. Healthy control blood was withdrawn by venepuncture and transferred into a container with sodium heparin anticoagulant (1 U/mL). The blood was collected and used within 1 hour for PBMC isolation.

Healthy Control human PBMCs prepared and frozen in advance were used PBMCs were prepared by layering blood on 15 mL Ficoll. Tubes were centrifuged at 800 g for 20 minutes, with brake off. The mononuclear cell layer at the interface was transferred to 50 mL Falcon tubes, washed by topping up to 45 mL with PBS and centrifuging at 300 g for 10 minutes. The pellets were resuspended in Freezing medium A (60:40 FCS:medium), 5% of the original blood volume and then an equal volume of Freezing medium B (80:20 FCS:DMSO) was added, dropwise to reduce osmotic shock. Cells were transferred to cryovials (1 mL per vial (around $1 \times 10^7$ cells)) and frozen in a Mr Frosty freezing container at −80° C. for up to 1 week, followed by transfer to liquid nitrogen for long term storage.

PBMC Recovery

Cells were thawed by removing from liquid nitrogen storage and immediately placed in a water bath at 37° C. until thawed. After transferring cell suspension to a 50 mL centrifuge tube, medium (RPMI+10% heat-inactivated FCS, 1% penicillin/streptomycin, and 1% glutamine) was added very slowly to decrease the DMSO concentration gradually. Once the volume was increased to 30 mL the cells were centrifuged, 300 g for 10 minutes, and resuspended in 5 mL medium before counting, made up to 15 mL with medium, centrifuged as above and cells resuspended in an appropriate volume of medium to yield $5 \times 10^6$ cells/1 mL.

In each of 5 individual experiments, two healthy control (HC), two RRMS, one PPMS and one SPMS, donor PBMC sample were thawed as above and cells treated as below. Different donors were used for each experiment, HCs broadly age and gender matched with the disease patient donors used.

T Cell Phenotyping Flow Cytometry Assay

Following resuspension of PBMCs at $5 \times 10^6$/mL in medium, 100 μL cells were transferred to FACS tubes (for full stain) and an additional 50 μL of HC samples (for FMO control tubes). Cells were washed by addition of 2 mL FACS buffer, centrifuged 300 g, 5 minutes and pellet resuspended in residual volume. 5 μL human FcX Trustain block was added for 10 mins followed by addition of 100 μl antibody stain cocktail and incubated at room temperature for 30 mins. Cells were washed by addition of 2 mL FACS buffer, centrifuged 300 g, 5 minutes and pellet resuspended in residual volume. 500 μl diluted Live/Dead Fixable Aqua Dead Cell Stain was added and incubated at room temperature for 25 mins. Cells were washed by addition of 2 mL FACS buffer, centrifuged 300 g, 5 minutes and pellet resuspended in residual volume. 200 μL FACS buffer was added and samples analyzed on the same day, using a BD FACS Canto II.

The performance of the instrument was checked using the Cytometer Set-up and Tracking (CST) Beads. This is a QC check for the instrument, sets the baselines and optimizes the voltages for each laser prior to use. The results of the calibration are stored within the CST software on the instrument.

Compensation for the instrument was performed using UltraComp compensation beads in accordance with the manufacturer's instructions. The relevant antibodies used to stain the cells during the experiment were used to label the compensation beads. Compensation for the experiments were performed using the appropriately labelled beads with the automatic compensation facility available within the FACS Diva software. After analysis of the compensation samples the compensation settings were calculated and applied to each experimental staining panel.

| Reagent |
| --- |
| PBS (w/o $Ca^{2+}$ and $Mg^{2+}$) |
| RPMI 1640 |
| L-Glutamine 200 mM |
| Pen/Strep |
| Heat inactivated FCS |
| DMSO |
| FcX Trustain blocking reagent |
| BD Horizon Brilliant Stain Buffer |
| anti-human CD8 AF488 (clone; RPA-T8) |
| anti-human CD25 PE (clone: BC96) |
| anti-human CD4 PerCP/Cy5.5 (clone: RPA-T4) |
| anti-CD4SRO PE/Cy7 (clone: UCHL1) |
| anti-CCR7 AF647 (clone: G043H7) |
| anti-CD20 APC/Fire750 (clone: 2H7) |
| anti-CD127 BV421 (clone: A019D5) |
| anti-CD14 BV510 (clone: M5E2) |
| anti-CD19 BV510 (clone: SJ25C1) |
| anti-CD56 BV510 (clone: 5.1H11) |
| anti-CD16 BV510 (clone: 3G8) |
| Aqua fixable Live/Dead stain |
| UltraComp eBeads Compensation Particles Set |
| BD FACSDiva CS&T Research Beads |

| Equipment Description |
| --- |
| Muse Cell Analyser (counter) |
| BD Canto II Flow Cytometer |

Samples were acquired on a BD FACS Canto II flow cytometer using BD BioSciences FACS Diva software (v8.0.1). Resulting compensated .fcs files were analyzed with FlowJo software (v10.0.8) and results generated in Excel using the Batch Analysis facility within the software.

T cell populations were analyzed in PBMCs from RRMS, PPMS and SPMS patients. Data was generated from patients where all patients were on treatment (10/10 RRMS patients on natalizumab and all progressive MS patients were on steroids and/or symptomatic treatments), a reduction in $T_{reg}$ cells was observed. $CD4^+$ (FIG. 5A), CD8(FIG. 5B) and regulatory T cells (FIG. 5C) from healthy controls and MS patients were profiled by flow cytometry based on CD45RO, CCR7, CD127 and CD25 expression on the cell surface. No difference was seen between healthy and disease T cell populations in either $CD4_{or}$ $_{CD}8^+$ subsets. The RRMS and PPMS $T_{reg}$ population was significantly reduced compared to HC, no difference was found in $T_{reg}$ numbers in SPMS patients. ***$0<0.0001$, *$0<0.05$ as tested by One-way ANOVA with Dunnett multiple comparison test. Data presented represent the mean±SEM of n=5-10 donors per group, analyzed in 5 independent experiments. Effector memory=CD45RO$^+$CCR7$^-$ central memory=CD45RO$^+$CCR7$^-$, naïve=CD45$^-$RO-CCR7$^+$, effector=CD45RO$^-$CCR7$^-$, $T_{reg}$=CD127$^{low/-}$/CD25$^+$.

Example 8: STAT5 Phosphorylation

All human samples were obtained with patient informed consent in accordance with ICH GCP under a protocol approved by a national, regional or investigational center ethics committee or an Institutional Review Board (IRB) approved protocol.

Healthy PBMCs were isolated from BDU blood and stored frozen in liquid nitrogen until used. Disease PBMCs were supplied by an approved external human tissue supplier.

Healthy control blood was withdrawn by venepuncture and transferred into a container with sodium heparin anticoagulant (1 U/mL). The blood was collected and used within 1 hour for PBMC isolation.

Healthy Control human PBMCs prepared and frozen in advance were used PBMCs were prepared by layering blood on 15 mL Ficoll. Tubes were centrifuged at 800 g for 20 minutes, with brake off. The mononuclear cell layer at the interface was transferred to 50 mL Falcon tubes, washed by topping up to 45 mL with PBS and centrifuging at 300 g for 10 minutes. The pellets were resuspended in Freezing medium A (60:40 FCS:medium), 5% of the original blood volume and then an equal volume of Freezing medium B (80:20 FCS:DMSO) was added, dropwise to reduce osmotic shock. Cells were transferred to cryovials (1 mL per vial (around $1\times10^7$ cells)) and frozen in a Mr Frosty freezing container at $-80°$ C. for up to 1 week, followed by transfer to liquid nitrogen for long term storage.

Cells were thawed by removing from liquid nitrogen storage and immediately placed in a water bath at 37° C. until thawed. After transferring cell suspension to a 50 mL centrifuge tube, medium (RPMI+10% heat-inactivated FCS, 1% penicillin/streptomycin, and 1% glutamine) was added very slowly to decrease DMSO concentration gradually. Once the volume was increased to 30 mL, the cells were centrifuged (300 g for 10 minutes) resuspended in 5 mL medium and counted, then topped up to 15 mL with medium, centrifuged as above and cells resuspended in an appropriate volume of medium to yield $5\times10^6$ cells/mL.

In each of 5 individual experiments, two healthy control (HC), two RRMS, one PPMS and one SPMS donor PBMC sample were thawed as above and cells treated as below. Different HC donors were used for each experiment, broadly age and gender matched with the disease patient donors used.

Inhibition of IL-7 Induced pSTAT5 by DRSPAI-L7B in T Cells

Following resuspension of PBMCs at $5\times10^6$/mL in medium, 450 µL cells were transferred to 15 mL Falcon tubes and incubated with 5 mL PBS containing 5 µL Near InfraRed live/dead stain. Cells were washed by the addition of 9 mL full culture medium, centrifuged (300 g, 5 minutes) and the cell pellet resuspended in AIM V serum free culture medium at $5\times10^6$ cells/mL. All antibody treatments and rhIL-7 stimulations were made up at 4× final assay concentration in AIM V serum free culture medium before mixing 1:1, (IL-7: mAb) and incubating at room temperature for 10 minutes. In the absence of either antibody or IL-7 stimulus, culture medium was added. Final concentration of IL-7 used was 1 ng/mL (57 pM). Final concentration of mAb used: 500 ng/mL (3.33 nM).

100 µL of PBMC suspension was added to four FACS tubes per donor ($5\times10^5$ cells/test). 100 µL of the antibody: IL-7 mixture was added to the appropriate FACS tubes (medium alone, IL-7 alone, IL-7+DRSPAI-L7B or IL-7+anti-RSV isotype control antibody). Tubes were mixed gently before incubating at 37° C. in a humidified incubator for 20 minutes. At the end of the stimulation period, the cells were centrifuged at 300 g for 5 minutes, the cell pellet resuspended and 250 µL of pre-warmed PHOSFLOW fixation buffer (1×) added. The samples were incubated for a further 10 minutes at 37° C. Following fixation, cells were pelleted by centrifugation (300 g, 5 minutes) and washed in 2 mL PBS. Cell pellets were resuspended in 100 µL ice cold Perm Buffer Ill and gently vortexing to mix. Cells were incubated on ice for 30 minutes before washing once in 1 mL PBS and centrifuging (300 g, 5 minutes). Cells were washed in 2 mL PBS then centrifuged (300 g, 5 minutes).

Following permeabilization cell pellets were resuspended in 25 µL FcR blocking reagent diluted 1:5 in FACS buffer. Cells were incubated for 10 minutes at room temperature before adding the detection antibody staining cocktail: 5 µL anti-CD3 (PerCP/Cy5.5), SpL anti-CD4 (AF488), 5 µL anti-CD8 (APC), 20 µL anti-pSTAT5 (PE) and 15 µL FACS buffer (50 µL total per test). Where a stain was excluded for FMO controls, the equivalent volume of FACS buffer was added instead. Tubes were mixed briefly and incubated at room temperature (RT) for 30 minutes, protected from light. Cells were washed in 2 mL FACS buffer, centrifuged (300 g, 5 mins) and pellets resuspended in 100 µL FACS buffer for analysis on the same day using a FACS Canto II flow cytometer.

The performance of the FACS Canto II instrument was checked using the Cytometer Set-up and Tracking (CST) Beads. This is a QC check for the instrument, sets the baselines and optimizes the voltages for each laser prior to use. The results of the calibration are stored within the CST software on the instrument.

Compensation for the instrument was performed using UltraComp compensation beads in accordance with the manufacturer's instructions. The relevant antibodies used to stain the cells during the experiment were used to label the appropriate compensation bead type. For compensation of live/dead cell dye, 1 µL of undiluted dye was added to 1 drop of ArcAmine reactive beads, incubated for 30 minutes, washed and ArcAmine negative beads added immediately before running sample.

Compensation for the experiments were performed using the appropriately labelled beads with the automatic compensation facility available within the FACS Diva software. After analysis of the compensation samples the compensation settings were calculated and applied to each experimental staining panel.

Antibody and Reagents

For experimentation, antibody aliquots were thawed and stored at 4° C. for no longer than 8 weeks. DRSPAI-L7B (anti-IL-7) and anti-RSV Isotype control.

| Reagent | Supplier |
| --- | --- |
| PBS (w/o Ca$^{2+}$ and Mg$^{2+}$) | Life Technologies |
| RPMI 1640 | Life Technologies |
| L-Glutamine 200 mM | Life Technologies |

| Reagent | Supplier |
|---|---|
| Pen/Strep | Life Technologies |
| Heat inactivated FCS | Life Technologies |
| AIM V Medium | Gibco |
| Recombinant human IL-7 | R&D Systems |
| BD Phosflow ™ Lyse/Fix Buffer 5x | BD Bioscience |
| BD Phosflow ™ Perm Buffer III | BD Biosciences |
| FcX Trustain blocking reagent | BioLegend |
| BD Phosflow ™ PE Mouse anti-STAT5 (pY694) | BD Bioscience |
| Mouse anti-human CD8 APC (clone: SK1) | BioLegend |
| Mouse anti-human CD4 AF488 (clone: RPA-T4) | BioLegend |
| Mouse anti-human CD3 PerCP/Cy5.5 (clone: SK7) | BioLegend |
| Near Infra-Red fixable Live/Dead stain | Life Technologies |
| UltraComp eBeads Compensation Particles Set | Life Technologies |
| ArcAmine reactive beads | Life Technologies |
| BD FACSDiva CS&T Research Beads | BD Biosciences |

| Equipment Description |
|---|
| Muse Cell Analyser (counter) |
| BD Canto II Flow Cytometer |

Samples were acquired on a BD FACS Canto II flow cytometer using BD BioSciences FACS Diva software (v8.0.1). Resulting compensated .fcs files were analyzed with FlowJo software (v10.0.8) and results generated in Excel using the Batch Analysis facility within the software.

In order to determine the capacity for disease cells to respond to IL-7 and confirm the efficacy of DRSPAI-L7B in samples from MS patients, PBMCs isolated from either healthy controls or MS patient donors were stimulated with 1 ng/mL (58 pM) IL-7 in the presence of a non-saturating (IC90=500 ng/mL (3.3 nM)) concentration of DRSPAI-L7B or anti-RSV IgG1K isotype control antibody.

PBMCs from healthy donors or MS patients (10 Healthy, 10 RRMS, 5 PPMS and 5 SPMS) were stimulated with rhIL-7 in the presence of DRSPAI-L7B or anti-RSV antibody (isotype control). STAT5 phosphorylation in CD4$^+$ (FIG. 6A) and CD8$^+$ (FIG. 6B) T cells was assessed by flow cytometry. IL-7 stimulation induced STAT5 phosphorylation in CD4$^+$ and CD8$^+$ T cells derived from healthy donors and MS patients with a 1 ng/mL (58 pM, ~200-fold higher than reported in disease). IL-7 stimulus was almost entirely abrogated by 500 ng/mL or 3.3 nM (non-saturating concentration) of DRSPAI-L7B. Data shown is normalized to IL-7 treatment condition, mean±SEM. * p<0.05,  p≤0.01, * p≤0.001, **** p<0.0001. One-way ANOVA with Tukey's multiple comparison correction. Similar results were observed upon IL-7 stimulation of PBMCs derived from IBD patients.

Example 9: IL-7 Levels in Disease

All human samples were obtained with patient informed consent in accordance with ICH GCP under a protocol approved by a national, regional or investigational center ethics committee or an Institutional Review Board (IRB) approved protocol. Samples were stored at −80° C. until required for use.

The measurement of IL-7 was conducted following the method SOP. Briefly, the method follows the MSD kit protocol with a sample dilution of 1:2 with Diluent 43. Diluted samples were incubated on a pre-coated IL-7 MSD plate followed by detection with a ruthenylated anti-IL-7 antibody. The level of IL-7 in the plasma sample is directly proportional to the resulting ECL signal read using the MSD Sector Imager 6000 Reader. The IL-7 method uses the MSD V-PLEX human IL-7 kit (catalogue no. K151RCD).

ECL signals for standards, controls, and unknown samples were derived from the MSD instrument and exported to Softmax Pro GxP for analysis. The back-calculated concentrations for each method were interpolated using the standard curve and a 4-parameter curve fitting model with 1/y2 weighting. A summary of the IL-7 concentrations was transferred to Microsoft Excel.

All data were transferred from Microsoft Excel 2016 to GraphPad Prism v. 6 for graphing and statistical analysis. Data were copied into "Column Tables" in Prism based on sample matrix (serum) and analyte (IL-7). Column statistics tests were carried out on each set of data including Shapiro-Wilk normality test to determine whether each data set was normally distributed. If data were not normally distributed, data were transformed using the formula y=log(y) to normalize distribution. Column statistics testing was carried out again on the transformed data in order to confirm normal distribution.

For serum samples, groups were compared using one-way analysis of variance (ANOVA). Distribution of the data was tested using the Shapiro-Wilk normality test in the column statistics function. Group differences in non-normally distributed data were assessed using Kruskal-Wallis unpaired, non-parametric analysis with Dunn's multiple comparisons test to compare the mean rank of each column with one another. Data were also transformed using y=log(y) in order to normalize the distribution of the data. Following transformation, Shapiro-Wilk test was carried out using the column statistics function to confirm that transformation resulted in normal distribution of the data. Transformed, normally distributed data was then assessed for statistically significant differences using an ordinary one-way, unpaired ANOVA with Tukey's multiple comparison test to compare the mean of each column to one another.

IL-7 levels were quantified in serum samples from healthy controls (HC, n=10), Crohn's disease (n=15), ulcerative colitis (UC, n=15), systemic lupus erythematosus (SLE, n=15) and primary Sjögren's syndrome (pSS, n=15) patients. IL-7 was significantly increased in Crohn's disease, UC and SLE (7.3, 9.44 and 5.53-fold, respectively) compared to healthy controls. There was also a small increase in IL-7 in the pSS cohort (3.55-fold vs HC). Data are mean±SD.  p≤0.01, * p≤0.001, **** p≤0.0001; Serum analyzed using 1-way ANOVA with Dunn's multiple comparisons correction. FIG. 7A and FIG. 7B.

Example 10: DRSPAI-L7B Production

Cell lines were transfected with a plasmid. This plasmid contained the codon optimized DRSPAI-L7B heavy and light chain genes, each under the transcriptional control of separate human EF1a promoters. The light chain constant region is human kappa and the heavy chain constant region is human IgG1, containing the LAGA substitution. LAGA substitution corresponds to L235A/G237A. Transfected cell lines were expanded and triaged based on expression of DRSPAI-L7B.

Example 11: Epitope Binding

Instrumentation
  Waters Synapt G2-Si mass spectrometer
  Acquity M Class UPLC
  LEAP H/D-X PAL liquid-handling robot
Solutions
  Quench solution: 400 mM potassium phosphate, 6 M guanidine hydrochloride, 0.5 M TCEP pH 2.5 (after 1:1 mixing with sample-quench buffer pH-adjusted with NaOH to give this pH on mixing).
  Dilution buffer:50 mM Na phosphate 100 mM NaCl in H2O pH7.0.
Proteins:
  IL-7: Concentration: 0.68 mg/ml (33 pM) in PBS. Sequence before processing (SED ID NO: 48):

MFHVSFRYIFGLPPLILVLLPVASSDCDIEGKDGKQYESVLMVSIDQLL

DSMKEIGSNCLNNEFNFFKRHICDANKEGMFLFRAARKLRQFLKMNSTG

DFDLHLLKVSEGTTILLNCTGQVKGRKPAALGEAQPTKSLEENKSLKEQ

KKLNDLCFLKRLLQEIKTCWNKILMGTKEHHHHHH

Secretory leader (underlined above)
  DRSPAI-L7B was produced in HEK cells and used at 15 mg/ml (100 pM) in PBS.
HDX
  Dilutions buffers were:
  Non-deuterated: 50 mM Na phosphate 100 mM NaCl in H2O pH7.0
  Deuterated: 50 mM Na phosphate 100 mM NaCl in D2O pD 6.6

For initial testing, DRSPAI-L7B was tested in a single run to check for digestion quality and signal strength.

For the HDX experiment, IL7:mAb mixture was prepared as follows: "Apo" sample comprised 20 µl concentrated IL7, 15 µl PBS and 25 µl dilution buffer. "mAb" samples comprised 20 µl concentrated IL7, 15 µl DRSPAI-L7B and 25 µl dilution buffer. This gave final nominal concentrations of 50 µM for IL7 and 25 µM for DRSPAI-L7B. Samples were prepared on ice and kept at 0° C. until analysis.

For the mAb binding experiments, samples were subjected to a standard deuteration method using 10-fold dilution into deuteration buffer, performed using the LEAP H/D-X PAL robot. Protein samples were placed in the 0° C. rack. 6 µl protein sample was transferred to a vial held at 20° C., then 54 µl dilution buffer (non-deuterated for 0 time point, deuterated for other time points) was added to initiate hydrogen exchange. After incubation for the appropriate time, 50 µl of this sample was aspirated and transferred to a pre-cooled vial (0° C.) containing 50 µl quench solution (400 mM sodium phosphate, 6 M guanidine hydrochloride, 0.5M tris-carboxyethyl phosphine[pH 2.5 after mixing with sample]). After mixing and incubation for 1 min, 90 µl of this sample was re-aspirated and transferred to the HDX manager, where through a 100 µl loop it was injected onto an immobilised pepsin column (Enzymate BEH, 2.1×30 mm, Waters #186007233, held at 15° C.), at 50 µl/min. Resulting peptides were eluted in 0.2% formic acid and trapped on a Vanguard BEH C18 pre-column (2.1×5 mm; Waters #186003975). The trap column was then switched in line with an analytical reverse-phase column (BEH C18, 1×100 mM, Waters #186002346) and peptides eluted using the following gradient, where A=0.2% formic acid, 0.03% trifluoroacetic acid in water, B=0.2% formic acid in acetonitrile:

| Step | Time(min) | Flow rate(uL/min) | % A | % B | Curve |
|---|---|---|---|---|---|
| 1. | Initial | 40.000 | 88.0 | 12.0 | |
| 2. | 8.00 | 40.000 | 64.0 | 36.0 | 6 |
| 3. | 9.00 | 40.000 | 5.0 | 95.0 | 6 |
| 4. | 10.00 | 40.000 | 5.0 | 95.0 | 6 |
| 5. | 10.50 | 40.000 | 88.0 | 12.0 | 6 |
| 6. | 11.50 | 40.000 | 5.0 | 95.0 | 6 |
| 7. | 13.00 | 40.000 | 5.0 | 95.0 | 6 |
| 8. | 13.50 | 40.000 | 88.0 | 12.0 | 6 |
| 9. | 15.00 | 40.000 | 88.0 | 12.0 | 6 |

During the gradient phase, the pepsin column was washed at 25 µl/min with pepsin wash buffer (2 M guanidine-HCl, 0.8% formic acid, 5% acetonitrile 5% propan-2-ol pH2.5), 2×80 µl, and returned to 0.2% formic acid at 25 µd/min in preparation for the next sample. Eluate from the analytical column was analyzed using ESI-MS, using a Waters Synapt G2-Si mass spectrometer operating in positive, resolution mode, with continuum data collected. Lockspray data containing Leucine-enkephalin and Glu-Fib ions was also acquired. For peptide identification samples, MSe data were acquired (acquisitions alternating between low and high energy conditions in the collision cell) to provide fragmentation data to aid robust peptide identification. For HDX samples, a single low energy acquisition (plus lockspray) was acquired.

An initial sample was run in $MS^e$ mode to generate a peptide search list using ProteinLynx Global Serverv3.0.2 (Waters). HDX samples were run in duplicate with deuteration periods of 0, 0.5 and 5 min.

The peptide search list was imported into DynamX v3.0 (Waters) and filtered to give high-quality peptides to search for in HDX samples(minimum intensity>10,000; peptide score >7.0. The HDX sample data were then brought in and processed to determine deuteration for each identified peptide in each sample. Peptide and ion assignments were manually checked and refined where necessary.

To interpolate the peptide-level data to residue-level data (to enable heat maps and structural views) the algorithm used by DynamX to generate heat maps was used, where for each residue data from the shortest overlapping peptide was used (where two overlapping peptides were of the same length, the peptide nearest the N-terminus was used).

Results

Two peptides in the region of residues 67-81 (numbering from full-length, unprocessed construct) showed strong protection in the presence of mAb.

(SEQ ID NO: 12-FKRHICDANKEGMFL)

(SEQ ID NO: 16-FKRHICDANKEGMF)

Again, the region covering the residues 67-81 showed a clear protection signal. Further, the heat-map data was mapped onto an available 3D structure for IL7 (in complex with IL7Rα), and the protected region covering residues 67-81 (FKRHICDANKEGMFL (SEQ ID NO: 12)). This region was distal from the region of IL7 interacting with the receptor IL7Rα. The epitope sits adjacent to the IL7Rα and γ-chain interaction sites on the folded protein.

Embodiments

Other aspects and embodiments of the disclosure will be apparent from the exemplary embodiments that follows.

Embodiments:

1. An IL-7 binding protein that binds to one or more amino acid residue within the amino acid sequence set forth in SEQ ID NO:12 of human IL-7.

2. The IL-7 binding protein of embodiment 1, which protects residues 67 to 81 (SEQ ID NO:12) of IL-7 from deuterium exchange in HDX-MS analysis.

3. The IL-7 binding protein of embodiment 1, which protects residues 67 to 80 (SEQ ID NO:16) of IL-7 from deuterium exchange in HDX-MS analysis.

4. An IL-7 binding protein or an IL-7 binding fragment thereof that binds to human IL-7 adjacent an IL-7Rα binding site, with a KD of 100 nM or less and inhibits IL-7 binding to IL-7R as measured in an in vitro competitive binding assay.

5. The IL-7 binding protein of any one of embodiments 1-4, wherein the IL-7 binding protein comprises at least one of (a) a heavy chain CDR1 having at least 80% identity to the amino acid sequence set out in SEQ ID NO:6, (b) a heavy chain CDR2 having at least 80% identity to the amino acid sequence set out in SEQ ID NO:7 or (c) a heavy chain CDR3 having at least 80% identity to the amino acid sequence set out in SEQ ID NO:8.

6. The IL-7 binding protein according to any one of embodiments 1-5, wherein the IL-7 binding protein comprises at least one of (a) a light chain CDR1 having at least 80% identity to the amino acid sequence set out in SEQ ID NO:9, (b) a light chain CDR2 having at least 80% identity to the amino acid sequence set out in SEQ ID NO:10 or (c) a light chain CDR3 having at least 80% identity to the amino acid sequence set out in SEQ ID NO:11.

7. The IL-7 binding protein according to any one of embodiments 1-6, wherein the IL-7 binding protein comprises a variable region light chain having at least 80% identity to the amino acid sequence set out in SEQ ID NO:5.

8. An IL-7 binding protein or an IL-7 binding fragment thereof comprising a variable region light chain having at least 95% identity to the amino acid sequence set out in SEQ ID NO:5.

9. The IL-7 binding protein according to embodiment 8, wherein the IL-7 binding protein comprises at least one of (a) a heavy chain CDR1 having at least 80% identity to the amino acid sequence set out in SEQ ID NO:6, (b) a heavy chain CDR2 having at least 80% identity to the amino acid sequence set out in SEQ ID NO:7 or (c) a heavy chain CDR3 having at least 80% identity to the amino acid sequence set out in SEQ ID NO:8.

10. An IL-7 binding protein or an IL-7 binding fragment thereof comprising a heavy chain CDR1 having at least 80% identity to the amino acid sequence set out in SEQ ID NO:6, a heavy chain CDR2 having at least 80% identity to the amino acid sequence set out in SEQ ID NO:7 and a heavy chain CDR3 having at least 80% identity to the amino acid sequence set out in SEQ ID NO:8.

11. An IL-7 binding protein or an IL-7 binding fragment thereof comprising a light chain CDR1 having at least 80% identity to the amino acid sequence set out in SEQ ID NO:9, a light chain CDR2 having at least 80% identity to the amino acid sequence set out in SEQ ID NO:10 and a light chain CDR3 having at least 80% identity to the amino acid sequence set out in SEQ ID NO:11.

12. The IL-7 binding protein according to any one of embodiments 10-11, wherein the IL-7 binding protein comprises a variable region light chain having at least 80% identity to the amino acid sequence set out in SEQ ID NO:5.

13. The IL-7 binding protein according to any one of the preceding embodiments, wherein the IL-7 binding protein comprises a variable region light chain having the amino acid sequence set out in SEQ ID NO:5.

14. The IL-7 binding protein according to any one of the preceding embodiments, wherein the IL-7 binding protein comprises a heavy chain CDR1 comprising the amino acid sequence set out in SEQ ID NO:6, a heavy chain CDR2 comprising the amino acid sequence set out in SEQ ID NO:7 and a heavy chain CDR3 comprising the amino acid sequence set out in SEQ ID NO:8.

15. The IL-7 binding protein according to any one of the preceding embodiments, wherein the IL-7 binding protein comprises a light chain CDR1 comprising the amino acid sequence set out in SEQ ID NO:9, a light chain CDR2 comprising the amino acid sequence set out in SEQ ID NO:10 and a light chain CDR3 the amino acid sequence set out in SEQ ID NO:11.

16. The IL-7 binding protein according to any one of the preceding embodiments, wherein the IL-7 binding protein comprises a variable region heavy chain having at least 80% identity to the amino acid sequence set out in SEQ ID N0:4.

17. The IL-7 binding protein according to any one of the preceding embodiments, wherein the IL-7 binding protein comprises a variable region heavy chain comprising the amino acid sequence set out in SEQ ID NO:4.

18. The IL-7 binding protein according to any one of the preceding embodiments, wherein the IL-7 binding protein comprises a light chain having at least 80% identity to the amino acid set sequence out in SEQ ID NO:3.

19. The IL-7 binding protein according to any one of the preceding embodiments, wherein the IL-7 binding protein comprises a light chain comprising the amino acid sequence set out in SEQ ID NO:3.

20. The IL-7 binding protein according to any one of the preceding embodiments, wherein the IL-7 binding protein comprises a constant region such that the IL-7 binding protein has reduced ADCC and/or complement activation or effector functionality.

21. The IL-7 binding protein according to embodiment 20, wherein the IL-7 binding protein comprises a heavy chain Fc domain having an alanine residue at position 235 and position 237 according to EU numbering.

22. The IL-7 binding protein according to any one of the preceding embodiments, wherein the IL-7 binding protein comprises a heavy chain having at least 80% identity to the amino acid sequence set out in SEQ ID NO:2.

23. The IL-7 binding protein according to any one of the preceding embodiments, wherein the IL-7 binding protein comprises a heavy chain comprising the amino acid sequence set out in SEQ ID NO:2.

24. The IL-7 binding protein according to any one of the preceding embodiments, wherein the IL-7 binding protein comprises a heavy chain comprising the amino acid sequence set out in SEQ ID NO:2 and a light chain comprising the amino acid sequence set out in SEQ ID NO:3.

25. The IL-7 binding protein according to any one of the preceding embodiments, wherein the IL-7 binding protein is an antibody or an antigen binding portion thereof.

26. The IL-7 binding protein according to embodiment 25, wherein the antibody is a monoclonal antibody.

27. The IL-7 binding protein according to embodiment 26, wherein the monoclonal antibody is an IgG1.

28. The IL-7 binding protein according to any one of the preceding embodiments, wherein the IL-7 binding protein is human, humanized or chimeric.

29. The IL-7 binding protein according to embodiment 28, wherein the IL-7 binding protein is humanized.

30. The IL-7 binding protein according to embodiment 28, wherein the IL-7 binding protein is human.

31. The IL-7 binding protein according to any one of the preceding embodiments, wherein the IL-7 binding protein binds to and neutralizes IL-7.

32. The IL-7 binding protein according to any one of the preceding embodiments, wherein the IL-7 binding protein binds to native IL-7.

33. The IL-7 binding protein according to any one of the preceding embodiments, wherein the IL-7 binding protein binds to circulating IL-7.

34. The IL-7 binding protein according to any one of the preceding embodiments, wherein the IL-7 binding protein is an isolated IL-7 binding protein.

35. The IL-7 binding protein according to any one of the preceding embodiments, wherein the IL-7 binding protein binds to IL-7 and inhibits IL-7 depending IFN-γ or IL-10 secretion from peripheral blood mononuclear cells with an IC50 of 1 nM or less.

36. The IL-7 binding protein according to any one of the preceding embodiments, wherein the IL-7 binding protein binds to IL-7 and inhibits IL-7 depending STAT5 phosphorylation in CD4+ T cells with an IC50 of 1 nM or less.

37. The IL-7 binding protein according to any one of the preceding embodiments, wherein the IL-7 binding protein is a reversible dimer.

38. The IL-7 binding protein according to any one of the preceding embodiments, wherein the IL-7 binding protein inhibits signaling, activation, cytokine production and proliferation of CD4+ T cells and/or CD8+ T cells.

39. A nucleic acid encoding the IL-7 binding protein according to any one of the preceding embodiments.

40. The nucleic acid of embodiment 39, wherein the nucleic acid comprises a sequence having at least 80% identity to the nucleic acid sequence set out in SEQ ID NO:13 encoding the light chain.

41. The nucleic acid of embodiment 39 or 40, wherein the nucleic acid comprises the nucleic acid sequence set out in SEQ ID NO:13 encoding the light chain.

42. The nucleic acid of embodiment any one of embodiments 39-41, wherein the nucleic acid comprises a sequence having at least 80% identity to the nucleic acid sequence set out in SEQ ID NO:14 encoding the heavy chain.

43. The nucleic acid of any one of embodiments 39-42, wherein the nucleic acid comprises the nucleic acid sequence set out in SEQ ID NO:14 encoding the heavy chain.

44. The nucleic acid of any one of embodiments 39-43, wherein the nucleic acid further comprises a sequence having at least 80% identity to the nucleic acid sequence set out in SEQ ID NO:15 encoding a signal peptide.

45. A vector comprising a nucleic acid according to any one of embodiments 39-44.

46. The vector of embodiment 45, further comprising a promoter functional in a mammalian cell.

47. A host cell comprising the nucleic acid according to any one of embodiments 39-44, or the vector according to embodiment 45 or 46.

48. A host cell according to embodiment 47, wherein the host cell is a CHO cell.

49. A method of making the IL-7 binding protein according to any one of embodiments 1-38, the method comprising maintaining the host cell according to embodiment 47 or 48 in a medium to produce the IL-7 binding protein and isolating or purifying the IL-7 binding protein produced by the host cell.

50. An IL-7 binding protein produced by the method of embodiment 49.

51. An IL-7 binding protein that competes for binding to IL-7 with the IL-7 binding protein of any one of embodiments 1-38.

52. A pharmaceutical composition, comprising a pharmaceutically-acceptable carrier and an IL-7 binding protein or an IL-7 binding fragment thereof that exhibits binding for IL-7 at an epitope comprising at least 5 contiguous amino acids of a sequence set out in SEQ ID NO:12.

53. The pharmaceutical composition of embodiment 52, wherein the IL-7 binding protein is according to any one of embodiments 1-38.

54. A pharmaceutical composition comprising the IL-7 binding protein according to any one of embodiments 1-38 and a pharmaceutically acceptable carrier or excipient.

55. The pharmaceutical composition according to any one of embodiments 52-54, wherein the pharmaceutical composition further comprises at least one additional therapeutic agent.

56. The pharmaceutical composition according to any one of embodiments 52-55, wherein the pharmaceutical composition has a pH of 4.5-7.0.

57. The pharmaceutical composition according to any one of embodiments 52-56, wherein the pharmaceutical composition has a pH of 5.5, 6.0, 6.2 or 6.5.

58. The IL-7 binding protein according to any one of embodiments 1-38, for use in therapy.

59. A method for treatment of an autoimmune and/or inflammatory condition in a subject in need thereof, comprising administering to the subject a therapeutically effective amount of the IL-7 binding protein according to any one of embodiments 1-38 or the pharmaceutical composition of embodiment 52-57.

60. The method according to embodiment 59, wherein the administering is transarterially, subcutaneously, intradermally, intratumorally, intranodally, intramedullary, intramuscularly, intravenously or intraperitoneally.

61. The method according to embodiment 60, wherein the administering is subcutaneously.

62. The method according to any one of embodiments 59-61, wherein the therapeutically effective amount is at least about 0.1 mg/kg, 0.5 mg/kg, 1 mg/kg, 3 mg/kg, 5 mg/kg, 10 mg/kg, 20 mg/kg, 30 mg/kg, or 40 mg/kg.

63. The method according to any one of embodiments 59-62, wherein the therapeutically effective amount is about 3 mg/kg.

64. The method according to any one of embodiments 59-63, wherein the therapeutically effective amount is administered to the subject at least about once every 1-60 days.

65. The method according to any one of embodiments 59-64, wherein the therapeutically effective amount is administered to the subject once every 4 weeks.

66. The method according to any one of embodiments 59-65, wherein the autoimmune and/or inflammatory condition is Sjögren's syndrome.

67. The method according to any one of embodiments 59-65, wherein the autoimmune and/or inflammatory condition is rheumatoid arthritis.

68. The method according to any one of embodiments 59-65, wherein the autoimmune and/or inflammatory condition is multiple sclerosis.

69. The method according to embodiment 68, wherein the multiple sclerosis is clinically isolated syndrome, relapsing-remitting, primary progressive or secondary progressive.

70. The method according to any one of embodiments 59-65, wherein the autoimmune and/or inflammatory condition is Crohn's disease.

71. The method according to any one of embodiments 59-65, wherein the autoimmune and/or inflammatory condition is ulcerative colitis.

72. The method according to any one of embodiments 59-65, wherein the autoimmune and/or inflammatory condition is lupus erythematosus.

73. The use of the IL-7 binding protein according to any one of embodiments 1-38, in the manufacture of a medicament for treatment of an autoimmune and/or inflammatory condition.

74. The use according to embodiment 73, wherein the autoimmune and/or inflammatory condition is Sjögren's syndrome.

75. The use according to embodiment 73, wherein the autoimmune and/or inflammatory condition is rheumatoid arthritis.

76. The use according to embodiment 73, wherein the autoimmune and/or inflammatory condition is multiple sclerosis.

77. The use according to embodiment 76, wherein the multiple sclerosis is clinically isolated syndrome, relapsing remitting, primary progressive or secondary progressive.

78. The use according to embodiment 73, wherein the autoimmune and/or inflammatory condition is Crohn's disease.

79. The use according to embodiment 73, wherein the autoimmune and/or inflammatory condition is ulcerative colitis.

80. The use according to embodiment 73, wherein the autoimmune and/or inflammatory condition is lupus erythematosus.

81. An IL-7 binding protein of any one of embodiments 1-38, for use in treatment of an autoimmune and/or inflammatory condition.

82. The IL-7 binding protein for use according to embodiment 81, wherein the autoimmune and/or inflammatory condition is Sjögren's syndrome.

83. The IL-7 binding protein for use according to embodiment 81, wherein the autoimmune and/or inflammatory condition is rheumatoid arthritis.

84. The IL-7 binding protein for use according to embodiment 81, wherein the autoimmune and/or inflammatory condition is multiple sclerosis.

85. The IL-7 binding protein for use according to embodiment 84, wherein the multiple sclerosis is clinically isolated syndrome, relapsing remitting, primary progressive or secondary progressive.

86. The IL-7 binding protein for use according to embodiment 81, wherein the autoimmune and/or inflammatory condition is Crohn's disease.

87. The IL-7 binding protein for use according to embodiment 81, wherein the autoimmune and/or inflammatory condition is ulcerative colitis.

88. The IL-7 binding protein for use according to embodiment 81, wherein the autoimmune and/or inflammatory condition is lupus erythematosus.

89. Use of the IL-7 binding protein according to any one of embodiments 1-38 or 50-51, for diagnosis of a disease or condition.

90. A composition comprising the IL-7 binding protein according to any one of embodiments 1-38 or 50-51, bound to a moiety or an antigenic fragment thereof.

91. The composition of embodiment 90, wherein the moiety is IL-7 or a fragment thereof.

92. A solid support comprising the IL-7 binding protein according to any one of embodiments 1-38 or 50-51.

93. The solid support of embodiment 92, wherein the solid support is an array.

94. A device that comprises:
a. the solid support according to embodiment 92 or 93, and
b. a processor for detecting a signal, wherein the signal is indicative of a binding of a moiety to the IL-7 binding protein according to any one of embodiments 1-38 or 50-51.

95. A pre-filled syringe or autoinjector device, comprising the IL-7 binding protein according to any one of embodiments 1-38, 50-51 or the pharmaceutical composition according to any one of embodiments 52-57.

96. A kit comprising the IL-7 binding protein according to any one of embodiments 1-38 or 50-51 and instructions for use.

97. An IL-7 binding protein comprising a light chain having at least 80% identity to the amino acid sequence set out in SEQ ID NO:18, SEQ ID NO:20, or SEQ ID NO:22.

98. An IL-7 binding protein of embodiment 97, comprising at least 80% identity to a CDR of SEQ ID NO:18, SEQ ID NO:20, or SEQ ID NO:22.

99. An IL-7 binding protein comprising a heavy chain having at least 80% identity to the amino acid sequence set out in SEQ ID NO:19, SEQ ID NO:21, or SEQ ID NO:23.

100. An IL-7 binding protein of embodiment 99, comprising at least 80% identity to a CDR of SEQ ID NO:19, SEQ ID NO:21, or SEQ ID NO:23.

101. An IL-7 binding protein comprising a light chain having the amino acid sequence set out in SEQ ID NO:18, SEQ ID NO:20, or SEQ ID NO:22 and a heavy chain having the amino acid sequence set out in SEQ ID NO:19, SEQ ID NO:21, or SEQ ID NO:23.

102. An IL-7 binding protein comprising a CDR of SEQ ID NO:18, SEQ ID NO:20, or SEQ ID NO:22 and a CDR of SEQ ID NO:19, SEQ ID NO:21, or SEQ ID NO:23.

103. An IL-7 binding protein comprising a light chain having the amino acid sequence set out in SEQ ID NO:18 and a heavy chain having the amino acid sequence set out in SEQ ID NO:19.

104. An IL-7 binding protein comprising a light chain having the amino acid sequence set out in SEQ ID NO:20 and a heavy chain having the amino acid sequence set out in SEQ ID NO:21.

105. An IL-7 binding protein comprising a light chain having the amino acid sequence set out in SEQ ID NO:22 and a heavy chain having the amino acid sequence set out in SEQ ID NO:23.

106. A composition comprising the IL-7 binding protein of any one of embodiments 97-105.

107. An IL-7 binding protein of any one of embodiments 97-105, for use in treatment of an autoimmune and/or inflammatory condition, wherein the autoimmune and/or inflammatory condition comprises Sjögren's syndrome, rheumatoid arthritis, multiple sclerosis (clinically isolated syndrome, relapsing remitting, primary progressive or secondary progressive), Crohn's disease, ulcerative colitis, or lupus erythematosus.

108. A method for treatment of an autoimmune and/or inflammatory condition comprising administering to a subject the composition of embodiment 106.

109. The method of embodiment 108, wherein the autoimmune and/or inflammatory condition comprises Sjögren's syndrome, rheumatoid arthritis, multiple sclerosis (clinically isolated syndrome, relapsing remitting, primary progressive or secondary progressive), Crohn's disease, ulcerative colitis, or lupus erythematosus.

110. The use of the IL-7 binding protein according to any one of embodiments 97-105, in the manufacture of a medicament for treatment of an autoimmune and/or inflammatory condition.

111. The use of embodiment 110, wherein the autoimmune and/or inflammatory condition comprises Sjögren's syndrome, rheumatoid arthritis, multiple sclerosis (clinically isolated syndrome, relapsing remitting, primary progressive or secondary progressive), Crohn's disease, ulcerative colitis, or lupus erythematosus.

112. A kit comprising the IL-7 binding protein according to any one of embodiments 97-105, and instructions for use.

```
                              Sequences

SEQ ID NO 1: human IL-7 Sequence with leader sequence
MFHVSFRYIFGLPPLILVLLPVASSDCDIEGKDGKQYESVLMVSIDQLLDSMKEIGSNCLNNEFNFFKRHICDANKEGMFL
FRAARKLRQFLKMNSTGDFDLHLLKVSEGTTILLNCTGQVKGRKPAALGEAQPTKSLEENKSLKEQKKLNDLCFLKRLLQ
EIKTCWNKILMGTKEH SEQ ID NO 2: DRSPAI-L7B heavy chain
QVQLVESGGGVVQPGRSLRLSCAASGFTFSSYGVHWVRQAPGKGLEWLAAIWTGGSTDYNSAFSSRFTISRDNSKNT
LYLQMNSLRAEDTAVYYCARNGYGESFAYWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSCDKTHTCPPCPAPELAG
APSVFLFPPKPKDTLMISRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLTCLVKGFYPSDIAVEWESNGQPENNYKTT
PPVLDSDGSFFLYSKLTVDKSRWQQ GNVFSCSVMHEALHNHYTQKSLSLSPGK SEQ ID NO 3: DRSPAI-L7B light chain
DIQMTQSPSSLSASVGDRVTITCKASESLDHDGDSYINWYQQKPGKAPKLLIYMGSNVEFGVPARFSGSGSGTDFTLTIS
SLQPEDFATYYCQQSNVDPLTFGGGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC SEQ ID NO 4: DRSPAI-L7B $V_H$
QVQLVESGGGVVQPGRSLRLSCAASGFTFSSYGVHWVRQAPGKGLEWLAAIWTGGSTDYNSAFSSRFTISRDNSKNT
LYLQMNSLRAEDTAVYYCARNGYGESFAYWGQGTLVTVSS SEQ ID NO 5: DRSPAI-L7B $V_L$
DIQMTQSPSSLSASVGDRVTITCKASESLDHDGDSYINWYQQKPGKAPKLLIYMGSNVEFGVPARFSGSGSGTDFTLTIS
SLQPEDFATYYCQQSNVDPLTFGGGTKVEIK

SEQ ID NO 6: DRSPAI-L7B CDRH1
SYGVH

SEQ ID NO 7: DRSPAI-L7B CDRH2
AIWTGGSTDYNSAFSS

SEQ ID NO 8: DRSPAI-L7B CDRH3
NGYGESFAY

SEQ ID NO 9: DRSPAI-L7B CDRL1
KASESLDHDGDSYIN

SEQ ID NO 10: DRSPAI-L7B CDRL2
MGSNVEF

SEQ ID NO 11: DRSPAI-L7B CDRL3
QQSNVDPLT

SEQ ID NO 12: DRSPAI-L7B $1^{st}$ protected site
FKRHICDANKEGMFL

SEQ ID NO 13: Nucleic acid sequence encoding DRSPAI-L7B light chain
GACATCCAGATGACCCAGAGCCCTAGCAGCCTGAGCGCCAGCGTGGGAGACAGGGTGACCATCACCTGCAAGGC
CAGCGAGTCCCTGGACCACGACGGCGACAGCTACATCAACTGGTACCAGCAGAAGCCCGGCAAGGCCCCCAAGCT
GCTGATCTACATGGGCAGCAACGTGGAGTTCGGCGTGCCCGCCAGGTTTAGCGGCAGCGGCAGCGGCACCGACT
TCACCCTGACCATCAGCAGCCTCCAGCCCGAGGACTTCGCCACCTACTACTGCCAGCAGAGCAACGTGGACCCCT
GACTTTCGGCGGCGGCACCAAGGTGGAGATTAAGCGTACGGTGGCCGCCCCCAGCGTGTTCATCTTCCCCCCCAG
CGATGAGCAGCTGAAGAGCGGCACCGCCAGCGTGGTGTGTCTGCTGAACAACTTCTACCCCCGGGAGGCCAAGG
TGCAGTGGAAGGTGGACAATGCCCTGCAGAGCGGCAACAGCCAGGAGAGCGTGACCGAGCAGGACAGCAAGGA
CTCCACCTACAGCCTGAGCAGCACCCTGACCCTGAGCAAGGCCGACTACGAGAAGCACAAGGTGTACGCCTGTGA
GGTGACCCACCAGGGCCTGTCCAGCCCCGTGACCAAGAGCTTCAACCGGGGCGAGTGC SEQ ID NO 14: Nucleic acid sequence encoding DRSPAI-L7B heavy chain
CAGGTGCAGCTGGTGGAGAGCGGCGGCGGCGTGGTCCAGCCCGGAAGGAGCCTGAGGCTGAGCTGCGCCGCCA
GCGGCTTCACCTTCAGCAGCTACGGGGTCCACTGGGTGAGGCAGGCCCCCGGAAAGGGCCTGGAGTGGCTGGCC
GCCATCTGGACCGGCGGCTCCACCGACTACAACAGCGCCTTCAGCAGCAGGTTCACCATCAGCAGGGACAACTCC
AAGAACACCCTGTACCTGCAGATGAACAGCCTCAGGGCCGAGGACACCGCCGTGTACTATTGCGCAAGGAACGG
```

| Sequences |
|---|
| CTACGGCGAGAGCTTCGCCTACTGGGCCAGGGCACCCTGGTGACCGTGAGCAGCGCCAGCACCAAGGGCCCCA
GCGTGTTCCCCCTGGCCCCCAGCAGCAAGAGCACCAGCGGCGGCACAGCCGCCCTGGGCTGCCTGGTGAAGGAC
TACTTCCCCGAGCCCGTGACCGTGTCCTGGAACAGCGGAGCCCTGACCAGCGGCGTGCACACCTTCCCCGCCGTGC
TGCAGAGCAGCGGCCTGTACAGCCTGAGCAGCGTGGTGACCGTGCCCAGCAGCAGCCTGGGCACCCAGACCTAC
ATCTGTAACGTGAACCACAAGCCCAGCAACACCAAGGTGGACAAGAAGGTGGAGCCCAAGAGCTGTGACAAGAC
CCACACCTGCCCCCCCTGCCCTGCCCCCGAGCTGGCCGGAGCCCCCAGCGTGTTCCTGTTCCCCCCCAAGCCTAAG
GACACCCTGATGATCAGCAGAACCCCCGAGGTGACCTGTGTGGTGGTGGATGTGAGCCACGAGGACCCTGAGGT
GAAGTTCAACTGGTACGTGGACGGCGTGGAGGTGCACAATGCCAAGACCAAGCCCAGGGAGGAGCAGTACAACA
GCACCTACCGGGTGGTGTCCGTGCTGACCGTGCTGCACCAGGATTGGCTGAACGGCAAGGAGTACAAGTGTAAG
GTGTCCAACAAGGCCCTGCCTGCCCCTATCGAGAAAACCATCAGCAAGGCCAAGGGCCAGCCCAGAGAGCCCCAG
GTGTACACCCTGCCCCCTAGCAGAGATGAGCTGACCAAGAACCAGGTGTCCCTGACCTGCCTGGTGAAGGGCTTC
TACCCCAGCGACATCGCCGTGGAGTGGGAGAGCAACGGCCAGCCCGAGAACAACTACAAGACCACCCCCCCTGTG
CTGGACAGCGATGGCAGCTTCTTCCTGTACAGCAAGCTGACCGTGGACAAGAGCAGATGGCAGCAGGGCAACGT
GTTCAGCTGCTCCGTGATGCACGAGGCCCTGCACAATCACTACACCCAGAAGAGCCTGAGCCTGTCCCCTGGCAA
G |

SEQ ID NO 15: Nucleic acid sequence encoding signaling peptide
ATGGGCTGGTCCTGCATCATCCTGTTTCTGGTGGCCACCGCCACCGGTGTGCACAGC SEQ ID NO: 16: DRSPAI-L7B 2$^{nd}$ protected site
FKRHICDANKEGMF SEQ ID NO 17: Human IL-7 Sequence (without secretory leader)
DCDIEGKDGKQYESVLMVSIDQLLDSMKEIGSNCLNNEFNFFKRHICDANKEGMFLFRAARKLRQFLKMNSTGDFDLH
LLKVSEGTTILLLNCTGQVKGRKPAALGEAQPTKSLEENKSLKEQKKLNDLCFLKRLLQEIKTCWNKILMGTKEH SEQ ID NO 18: A1290 light chain
DIQMTQSPSSLSASVGDRVTITCKASQSVDDDGDSFINWYQQKPGKAPKLLIYVASNLESGVPARFSGSGSGTDFTLTIS
SLQPEDFATYYCQQSNEDPLTFGGGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC SEQ ID NO 19: A1290 heavy chain
QVQLVESGGGVVQPGRSLRLSCAASGFTFSSYGLHWVRQAPGKGLEWLAAIWTGGSTDYNAAFISRFTISRDNSKNTL
YLQMNSLRAEDTAVYYCARNGYGESFAYWGQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPELAGA
PSVFLFPPKPKDTLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK SEQ ID NO 20: A1291 light chain
DIQMTQSPSSLSASVGDRVTITCKASHSVDDDGDSYMNWYQQKPGKAPKLLIYMASNLESGVPARFSGSGSGTDFTLT
ISSLQPEDFATYYCQQSNEDPLTFGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC SEQ ID NO 21: A1291 heavy chain
QVQLVESGGGVVQPGRSLRLSCAASGFTFSSYGLHWVRQAPGKGLEWLAAIWTGGSTDYNAEFSSRFTISRDNSKNTL
YLQMNSLRAEDTAVYYCARNGYGESFAYWGQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPELAGA
PSVFLFPPKPKDTLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK SEQ ID NO 22: A1294 light chain
DIQMTQSPSSLSASVGDRVTITCKASQSVDDDGDSYMNWYQQKPGKAPKLLIYMASNLESGVPARFSGSGSGTDFTLT
ISSLQPEDFATYYCQQSNEDPLTFGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC SEQ ID NO 23: A1294 heavy chain
QVQLVESGGGVVQPGRSLRLSCAASGFTFSTYGVHWVRQAPGKGLEWLAAIWSGGSTDYNVAFSSRFTISRDNSKNTL
YLQMNSLRAEDTAVYYCARNGYGESFAYWGQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPELAGA
PSVFLFPPKPKDTLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK SEQ ID NO 24: A1290 $V_L$
DIQMTQSPSSLSASVGDRVTITCKASQSVDDDGDSFINWYQQKPGKAPKLLIYVASNLESGVPARFSGSGSGTDFTLTIS
SLQPEDFATYYCQQSNEDPLTFGGGTKVEIK SEQ ID NO 25: A1290 $V_H$
QVQLVESGGGVVQPGRSLRLSCAASGFTFSSYGLHWVRQAPGKGLEWLAAIWTGGSTDYNAAFISRFTISRDNSKNTL
YLQMNSLRAEDTAVYYCARNGYGESFAYWGQGTLVTVSS

SEQ ID NO 26: A1290 CDRH1
SYGLH

-continued

| Sequences |
|---|

SEQ ID NO 27: A1290 CDRH2
AIWTGGSTDYNAAFIS

SEQ ID NO 28: A1290 CDRH3
NGYGESFAY

SEQ ID NO 29: A1290 CDRL1
KASQSVDDDGDSFIN

SEQ ID NO 30: A1290 CDRL2
VASNLES

SEQ ID NO 31: A1290 CDRL3
QQSNEDPLT

SEQ ID NO 32: A1291 $V_L$
DIQMTQSPSSLSASVGDRVTITCKASHSVDDDGDSYMNWYQQKPGKAPKLLIYMASNLESGVPARFSGSGSGTDFTLT
ISSLQPEDFATYYCQQSNEDPLTFGGGTKVEIK

SEQ ID NO 33: A1291 $V_H$
QVQLVESGGGVVQPGRSLRLSCAASGFTFSSYGLHWVRQAPGKGLEWLAAIWTGGSTDYNAEFSSRFTISRDNSKNTL
YLQMNSLRAEDTAVYYCARNGYGESFAYWGQGTLVTSS

SEQ ID NO 34: A1291 CDRH1
SYGLH

SEQ ID NO 35: A1291 CDRH2
AIWTGGSTDYNAEFSS

SEQ ID NO 36: A1291 CDRH3
NGYGESFAY

SEQ ID NO 37: A1291 CDRL1
KASHSVDDDGDSYMN

SEQ ID NO 38: A1291 CDRL2
MASNLES

SEQ ID NO 39: A1291 CDRL3
QQSNEDPLT

SEQ ID NO 40: A1294 $V_L$
DIQMTQSPSSLSASVGDRVTITCKASQSVDDDGDSYMNWYQQKPGKAPKLLIYMASNLESGVPARFSGSGSGTDFTLT
ISSLQPEDFATYYCQQSNEDPLTFGGGTKVEIK

SEQ ID NO 41: A1294 $V_H$
QVQLVESGGGVVQPGRSLRLSCAASGFTFSTYGVHWVRQAPGKGLEWLAAIWSGGSTDYNVAFSSRFTISRDNSKNTL
YLQMNSLRAEDTAVYYCARNGYGESFAYWGQGTLVTSS

SEQ ID NO 42: A1294 CDRH1
TYGVH

SEQ ID NO 43: A1294 CDRH2
AIWSGGSTDYNVAFSS

SEQ ID NO 44: A1294 CDRH3
NGYGESFAY

SEQ ID NO 45: A1294 CDRL1
KASQSVDDDGDSYMN

SEQ ID NO 46: A1294 CDRL2
MASNLES

SEQ ID NO 47: A1294 CDRL3
QQSNEDPLT

SEQUENCE LISTING

Sequence total quantity: 48
SEQ ID NO: 1          moltype = AA   length = 177
FEATURE               Location/Qualifiers
REGION                1..177

```
                         note = human IL-7 Sequence with leader sequence
source                   1..177
                         mol_type = protein
                         organism = synthetic construct
SEQUENCE: 1
MFHVSFRYIF GLPPLILVLL PVASSDCDIE GKDGKQYESV LMVSIDQLLD SMKEIGSNCL   60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEH     177

SEQ ID NO: 2             moltype = AA   length = 447
FEATURE                  Location/Qualifiers
REGION                   1..447
                         note = DRSPAI-L7B heavy chain
source                   1..447
                         mol_type = protein
                         organism = synthetic construct
SEQUENCE: 2
QVQLVESGGG VVQPGRSLRL SCAASGFTFS SYGVHWVRQA PGKGLEWLAA IWTGGSTDYN   60
SAFSSRFTIS RDNSKNTLYL QMNSLRAEDT AVYYCARNGY GESFAYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELAGAPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 3             moltype = AA   length = 218
FEATURE                  Location/Qualifiers
REGION                   1..218
                         note = DRSPAI-L7B light chain
source                   1..218
                         mol_type = protein
                         organism = synthetic construct
SEQUENCE: 3
DIQMTQSPSS LSASVGDRVT ITCKASESLD HDGSYINWY QQKPGKAPKL LIYMGSNVEF    60
GVPARFSGSG SGTDFTLTIS SLQPEDFATY YCQQSNVDPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 4             moltype = AA   length = 117
FEATURE                  Location/Qualifiers
REGION                   1..117
                         note = DRSPAI-L7B Vh
source                   1..117
                         mol_type = protein
                         organism = synthetic construct
SEQUENCE: 4
QVQLVESGGG VVQPGRSLRL SCAASGFTFS SYGVHWVRQA PGKGLEWLAA IWTGGSTDYN   60
SAFSSRFTIS RDNSKNTLYL QMNSLRAEDT AVYYCARNGY GESFAYWGQG TLVTVSS    117

SEQ ID NO: 5             moltype = AA   length = 111
FEATURE                  Location/Qualifiers
REGION                   1..111
                         note = DRSPAI-L7B Vl
source                   1..111
                         mol_type = protein
                         organism = synthetic construct
SEQUENCE: 5
DIQMTQSPSS LSASVGDRVT ITCKASESLD HDGSYINWY QQKPGKAPKL LIYMGSNVEF    60
GVPARFSGSG SGTDFTLTIS SLQPEDFATY YCQQSNVDPL TFGGGTKVEI K           111

SEQ ID NO: 6             moltype = AA   length = 5
FEATURE                  Location/Qualifiers
REGION                   1..5
                         note = DRSPAI-L7B CDRH1
source                   1..5
                         mol_type = protein
                         organism = synthetic construct
SEQUENCE: 6
SYGVH                                                               5

SEQ ID NO: 7             moltype = AA   length = 16
FEATURE                  Location/Qualifiers
REGION                   1..16
                         note = DRSPAI-L7B CDRH2
source                   1..16
                         mol_type = protein
                         organism = synthetic construct
SEQUENCE: 7
```

```
AIWTGGSTDY NSAFSS                                                             16

SEQ ID NO: 8              moltype = AA  length = 9
FEATURE                   Location/Qualifiers
REGION                    1..9
                          note = DRSPAI-L7B CDRH3
source                    1..9
                          mol_type = protein
                          organism = synthetic construct
SEQUENCE: 8
NGYGESFAY                                                                      9

SEQ ID NO: 9              moltype = AA  length = 15
FEATURE                   Location/Qualifiers
REGION                    1..15
                          note = DRSPAI-L7B CDRL1
source                    1..15
                          mol_type = protein
                          organism = synthetic construct
SEQUENCE: 9
KASESLDHDG DSYIN                                                              15

SEQ ID NO: 10             moltype = AA  length = 7
FEATURE                   Location/Qualifiers
REGION                    1..7
                          note = DRSPAI-L7B CDRL2
source                    1..7
                          mol_type = protein
                          organism = synthetic construct
SEQUENCE: 10
MGSNVEF                                                                        7

SEQ ID NO: 11             moltype = AA  length = 9
FEATURE                   Location/Qualifiers
REGION                    1..9
                          note = DRSPAI-L7B CDRL3
source                    1..9
                          mol_type = protein
                          organism = synthetic construct
SEQUENCE: 11
QQSNVDPLT                                                                      9

SEQ ID NO: 12             moltype = AA  length = 15
FEATURE                   Location/Qualifiers
REGION                    1..15
                          note = DRSPAI-L7B 1st protected site
source                    1..15
                          mol_type = protein
                          organism = synthetic construct
SEQUENCE: 12
FKRHICDANK EGMFL                                                              15

SEQ ID NO: 13             moltype = DNA  length = 654
FEATURE                   Location/Qualifiers
misc_feature              1..654
                          note = Nucleic acid sequence encoding DRSPAI-L7B light chain
source                    1..654
                          mol_type = other DNA
                          organism = synthetic construct
SEQUENCE: 13
gacatccaga tgacccagag ccctagcagc ctgagcgcca gcgtgggaga cagggtgacc              60
atcacctgca aggccagcga gtccctggac cacgacggcg acagctacat caactggtac             120
cagcagaagc ccggcaaggc ccccaagctg ctgatctaca tgggcagcaa cgtggagttc             180
ggcgtgcccg ccaggtttag cggcagcggc agcggcaccg acttcaccct gaccatcagc             240
agcctccagc ccgaggactt cgccacctac tactgccagc agagcaacgt ggaccccctg             300
actttcggcg gcggcaccaa ggtggagatt aagcgtacgg tggccgcccc cagcgtgttc             360
atcttccccc ccagcgatga gcagctgaag agcggcaccg ccagcgtggt gtgtctgctg             420
aacaacttct accccgggga ggccaaggtg cagtggaagg tggacaatgc cctgcagagc             480
ggcaacagcc aggagagcgt gaccgagcag gacagcaagg actccaccta cagcctgagc             540
agcaccctga ccctgagcaa ggccgactac gagaagcaca aggtgtacgc ctgtgaggtg             600
acccaccagg gcctgtccag ccccgtgacc aagagcttca ccggggcga gtgc                    654

SEQ ID NO: 14             moltype = DNA  length = 1341
FEATURE                   Location/Qualifiers
misc_feature              1..1341
                          note = Nucleic acid sequence encoding DRSPAI-L7B heavy chain
source                    1..1341
                          mol_type = other DNA
                          organism = synthetic construct
```

-continued

```
SEQUENCE: 14
caggtgcagc tggtggagag cggcggcggc gtggtccagc ccggaaggag cctgaggctg    60
agctgcgccg ccagcggctt caccttcagc agctacgggg tccactgggt gaggcaggcc   120
cccgaaagg gcctggagtg gctggccgcc atctggaccg cggctccac cgactacaac    180
agcgccttca gcagcaggtt caccatcagc agggacaact ccaagaacac cctgtacctg   240
cagatgaaca gcctcaggc cgaggacacc gccgtgtact attgcgcaag aacggctac    300
ggcgagagct tcgcctactg gggccagggc accctggtga ccgtgagcag cgccagcacc   360
aagggcccca gcgtgttccc cctggccccc agcagcaaga gcaccagcgg cggcacagcc   420
gccctgggct gcctggtgaa ggactacttc cccgagcccg tgaccgtgtc ctggaacagc   480
ggagccctga ccagcggcgt gcacaccttc ccggccgtgc tgcagagcag cggcctgtac   540
agcctgagca gcgtggtgac cgtgcccagc agcagcctgg gcacccagac ctacatctgt   600
aacgtgaacc acaagcccag caacaccaag gtggacaaga aggtggagcc caagagctgt   660
gacaagaccc acacctgccc ccctgccct gcccccgagc tggccggagc cccagcgtg    720
ttcctgttcc ccccaagcc taaggacacc ctgatgatca gcagaacccc cgaggtgacc   780
tgtgtggtgg tggatgtgag ccacgaggac cctgaggtga agttcaactg gtacgtggac   840
ggcgtggagg tgcacaatgc caagaccaag cccagggagg agcagtacaa cagcacctac   900
cgggtggtgt ccgtgctgac cgtgctgcac caggattggc tgaacggcaa ggagtacaag   960
tgtaaggtgt ccaacaaggc cctgcctgcc cctatcgaaa aaaccatcag caaggccaaa  1020
ggccagccca gagagcccca ggtgtacacc ctgcccccta gcagagatga gctgaccaag  1080
aaccaggtgt ccctgacctg cctggtgaag ggcttctacc ccagcgacat cgccgtggag  1140
tgggagagca acggccagcc cgagaacaac tacaagacca ccccccctgt gctggacagc  1200
gatggcagct tcttcctgta cagcaagctg accgtggaca gagcagatg gcagcagggc  1260
aacgtgttca gctgctccgt gatgcacgag gccctgcaca atcactacac ccagaagagc  1320
ctgagcctgt cccctggcaa g                                          1341

SEQ ID NO: 15         moltype = DNA  length = 57
FEATURE               Location/Qualifiers
misc_feature          1..57
                      note = Nucleic acid sequence encoding signaling peptide
source                1..57
                      mol_type = other DNA
                      organism = synthetic construct
SEQUENCE: 15
atgggctggt cctgcatcat cctgtttctg gtggccaccg ccaccggtgt gcacagc      57

SEQ ID NO: 16         moltype = AA  length = 14
FEATURE               Location/Qualifiers
REGION                1..14
                      note = DRSPAI-L7B 2nd protected site
source                1..14
                      mol_type = protein
                      organism = synthetic construct
SEQUENCE: 16
FKRHICDANK EGMF                                                     14

SEQ ID NO: 17         moltype = AA  length = 152
FEATURE               Location/Qualifiers
REGION                1..152
                      note = Human IL-7 Sequence (without secretory leader)
source                1..152
                      mol_type = protein
                      organism = synthetic construct
SEQUENCE: 17
DCDIEGKDGK QYESVLMVSI DQLLDSMKEI GSNCLNNEFN FFKRHICDAN KEGMFLFRAA    60
RKLRQFLKMN STGDFDLHLL KVSEGTTILL NCTGQVKGRK PAALGEAQPT KSLEENKSLK   120
EQKKLNDLCF LKRLLQEIKT CWNKILMGTK EH                                 152

SEQ ID NO: 18         moltype = AA  length = 218
FEATURE               Location/Qualifiers
REGION                1..218
                      note = A1290 light chain
source                1..218
                      mol_type = protein
                      organism = synthetic construct
SEQUENCE: 18
DIQMTQSPSS LSASVGDRVT ITCKASQSVD DDGDSFINWY QQKPGKAPKL LIYVASNLES    60
GVPARFSGSG SGTDFTLTIS SLQPEDFATY YCQQSNEDPL TFGGGTKVEI KRTVAAPSVF   120
IPPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 19         moltype = AA  length = 447
FEATURE               Location/Qualifiers
REGION                1..447
                      note = A1290 heavy chain
source                1..447
                      mol_type = protein
                      organism = synthetic construct
SEQUENCE: 19
QVQLVESGGG VVQPGRSLRL SCAASGFTFS SYGLHWVRQA PGKGLEWLAA IWTGGSTDYN    60
```

```
AAFISRFTIS RDNSKNTLYL QMNSLRAEDT AVYYCARNGY GESFAYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELAGAPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447

SEQ ID NO: 20              moltype = AA   length = 218
FEATURE                    Location/Qualifiers
REGION                     1..218
                           note = A1291 light chain
source                     1..218
                           mol_type = protein
                           organism = synthetic construct
SEQUENCE: 20
DIQMTQSPSS LSASVGDRVT ITCKASHSVD DDGDSYMNWY QQKPGKAPKL LIYMASNLES    60
GVPARFSGSG SGTDFTLTIS SLQPEDFATY YCQQSNEDPL TFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 21              moltype = AA   length = 447
FEATURE                    Location/Qualifiers
REGION                     1..447
                           note = A1291 heavy chain
source                     1..447
                           mol_type = protein
                           organism = synthetic construct
SEQUENCE: 21
QVQLVESGGG VVQPGRSLRL SCAASGFTFS SYGLHWVRQA PGKGLEWLAA IWTGGSTDYN    60
AEFSSRFTIS RDNSKNTLYL QMNSLRAEDT AVYYCARNGY GESFAYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELAGAPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447

SEQ ID NO: 22              moltype = AA   length = 218
FEATURE                    Location/Qualifiers
REGION                     1..218
                           note = A1294 light chain
source                     1..218
                           mol_type = protein
                           organism = synthetic construct
SEQUENCE: 22
DIQMTQSPSS LSASVGDRVT ITCKASQSVD DDGDSYMNWY QQKPGKAPKL LIYMASNLES    60
GVPARFSGSG SGTDFTLTIS SLQPEDFATY YCQQSNEDPL TFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 23              moltype = AA   length = 447
FEATURE                    Location/Qualifiers
REGION                     1..447
                           note = A1294 heavy chain
source                     1..447
                           mol_type = protein
                           organism = synthetic construct
SEQUENCE: 23
QVQLVESGGG VVQPGRSLRL SCAASGFTFS TYGVHWVRQA PGKGLEWLAA IWSGGSTDYN    60
VAFSSRFTIS RDNSKNTLYL QMNSLRAEDT AVYYCARNGY GESFAYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELAGAPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447

SEQ ID NO: 24              moltype = AA   length = 111
FEATURE                    Location/Qualifiers
REGION                     1..111
                           note = A1290 light chain
source                     1..111
                           mol_type = protein
                           organism = synthetic construct
SEQUENCE: 24
DIQMTQSPSS LSASVGDRVT ITCKASQSVD DDGDSFINWY QQKPGKAPKL LIYVASNLES    60
GVPARFSGSG SGTDFTLTIS SLQPEDFATY YCQQSNEDPL TFGGGTKVEI K              111
```

```
SEQ ID NO: 25              moltype = AA   length = 117
FEATURE                    Location/Qualifiers
REGION                     1..117
                           note = A1290 Heavy chain
source                     1..117
                           mol_type = protein
                           organism = synthetic construct
SEQUENCE: 25
QVQLVESGGG VVQPGRSLRL SCAASGFTFS SYGLHWVRQA PGKGLEWLAA IWTGGSTDYN    60
AAFISRFTIS RDNSKNTLYL QMNSLRAEDT AVYYCARNGY GESFAYWGQG TLVTVSS      117

SEQ ID NO: 26              moltype = AA   length = 5
FEATURE                    Location/Qualifiers
REGION                     1..5
                           note = A1290 CDRH1
source                     1..5
                           mol_type = protein
                           organism = synthetic construct
SEQUENCE: 26
SYGLH                                                                 5

SEQ ID NO: 27              moltype = AA   length = 16
FEATURE                    Location/Qualifiers
REGION                     1..16
                           note = A1290 CDRH2
source                     1..16
                           mol_type = protein
                           organism = synthetic construct
SEQUENCE: 27
AIWTGGSTDY NAAFIS                                                    16

SEQ ID NO: 28              moltype = AA   length = 9
FEATURE                    Location/Qualifiers
REGION                     1..9
                           note = A1290 CDRH3
source                     1..9
                           mol_type = protein
                           organism = synthetic construct
SEQUENCE: 28
NGYGESFAY                                                             9

SEQ ID NO: 29              moltype = AA   length = 15
FEATURE                    Location/Qualifiers
REGION                     1..15
                           note = A1290 CDRL1
source                     1..15
                           mol_type = protein
                           organism = synthetic construct
SEQUENCE: 29
KASQSVDDDG DSFIN                                                     15

SEQ ID NO: 30              moltype = AA   length = 7
FEATURE                    Location/Qualifiers
REGION                     1..7
                           note = A1290 CDRL2
source                     1..7
                           mol_type = protein
                           organism = synthetic construct
SEQUENCE: 30
VASNLES                                                               7

SEQ ID NO: 31              moltype = AA   length = 9
FEATURE                    Location/Qualifiers
REGION                     1..9
                           note = A1290 CDRL3
source                     1..9
                           mol_type = protein
                           organism = synthetic construct
SEQUENCE: 31
QQSNEDPLT                                                             9

SEQ ID NO: 32              moltype = AA   length = 111
FEATURE                    Location/Qualifiers
REGION                     1..111
                           note = A1291 light chain
source                     1..111
                           mol_type = protein
                           organism = synthetic construct
SEQUENCE: 32
```

```
DIQMTQSPSS LSASVGDRVT ITCKASHSVD DDGDSYMNWY QQKPGKAPKL LIYMASNLES    60
GVPARFSGSG SGTDFTLTIS SLQPEDFATY YCQQSNEDPL TFGGGTKVEI K            111

SEQ ID NO: 33            moltype = AA   length = 117
FEATURE                  Location/Qualifiers
REGION                   1..117
                         note = A1291 heavy chain
source                   1..117
                         mol_type = protein
                         organism = synthetic construct
SEQUENCE: 33
QVQLVESGGG VVQPGRSLRL SCAASGFTFS SYGLHWVRQA PGKGLEWLAA IWTGGSTDYN    60
AEFSSRFTIS RDNSKNTLYL QMNSLRAEDT AVYYCARNGY GESFAYWGQG TLVTVSS      117

SEQ ID NO: 34            moltype = AA   length = 5
FEATURE                  Location/Qualifiers
REGION                   1..5
                         note = A1291 CDRH1
source                   1..5
                         mol_type = protein
                         organism = synthetic construct
SEQUENCE: 34
SYGLH                                                                5

SEQ ID NO: 35            moltype = AA   length = 16
FEATURE                  Location/Qualifiers
REGION                   1..16
                         note = A1291 CDRH2
source                   1..16
                         mol_type = protein
                         organism = synthetic construct
SEQUENCE: 35
AIWTGGSTDY NAEFSS                                                   16

SEQ ID NO: 36            moltype = AA   length = 9
FEATURE                  Location/Qualifiers
REGION                   1..9
                         note = A1291 CDRH3
source                   1..9
                         mol_type = protein
                         organism = synthetic construct
SEQUENCE: 36
NGYGESFAY                                                            9

SEQ ID NO: 37            moltype = AA   length = 15
FEATURE                  Location/Qualifiers
REGION                   1..15
                         note = A1291 CDRL1
source                   1..15
                         mol_type = protein
                         organism = synthetic construct
SEQUENCE: 37
KASHSVDDDG DSYMN                                                    15

SEQ ID NO: 38            moltype = AA   length = 7
FEATURE                  Location/Qualifiers
REGION                   1..7
                         note = A1291 CDRL2
source                   1..7
                         mol_type = protein
                         organism = synthetic construct
SEQUENCE: 38
MASNLES                                                              7

SEQ ID NO: 39            moltype = AA   length = 9
FEATURE                  Location/Qualifiers
REGION                   1..9
                         note = A1291 CDRL3
source                   1..9
                         mol_type = protein
                         organism = synthetic construct
SEQUENCE: 39
QQSNEDPLT                                                            9

SEQ ID NO: 40            moltype = AA   length = 111
FEATURE                  Location/Qualifiers
REGION                   1..111
                         note = A1294 light chain
source                   1..111
```

```
                         mol_type = protein
                         organism = synthetic construct
SEQUENCE: 40
DIQMTQSPSS LSASVGDRVT ITCKASQSVD DDGDSYMNWY QQKPGKAPKL LIYMASNLES    60
GVPARFSGSG SGTDFTLTIS SLQPEDFATY YCQQSNEDPL TFGGGTKVEI K            111

SEQ ID NO: 41            moltype = AA  length = 117
FEATURE                  Location/Qualifiers
REGION                   1..117
                         note = A1294 heavy chain
source                   1..117
                         mol_type = protein
                         organism = synthetic construct
SEQUENCE: 41
QVQLVESGGG VVQPGRSLRL SCAASGFTFS TYGVHWVRQA PGKGLEWLAA IWSGGSTDYN    60
VAFSSRFTIS RDNSKNTLYL QMNSLRAEDT AVYYCARNGY GESFAYWGQG TLVTVSS      117

SEQ ID NO: 42            moltype = AA  length = 5
FEATURE                  Location/Qualifiers
REGION                   1..5
                         note = A1294 CDRH1
source                   1..5
                         mol_type = protein
                         organism = synthetic construct
SEQUENCE: 42
TYGVH                                                                5

SEQ ID NO: 43            moltype = AA  length = 16
FEATURE                  Location/Qualifiers
REGION                   1..16
                         note = A1294 CDRH2
source                   1..16
                         mol_type = protein
                         organism = synthetic construct
SEQUENCE: 43
AIWSGGSTDY NVAFSS                                                    16

SEQ ID NO: 44            moltype = AA  length = 9
FEATURE                  Location/Qualifiers
REGION                   1..9
                         note = A1294 CDRH3
source                   1..9
                         mol_type = protein
                         organism = synthetic construct
SEQUENCE: 44
NGYGESFAY                                                            9

SEQ ID NO: 45            moltype = AA  length = 15
FEATURE                  Location/Qualifiers
REGION                   1..15
                         note = A1294 CDRL1
source                   1..15
                         mol_type = protein
                         organism = synthetic construct
SEQUENCE: 45
KASQSVDDDG DSYMN                                                     15

SEQ ID NO: 46            moltype = AA  length = 7
FEATURE                  Location/Qualifiers
REGION                   1..7
                         note = A1294 CDRL2
source                   1..7
                         mol_type = protein
                         organism = synthetic construct
SEQUENCE: 46
MASNLES                                                              7

SEQ ID NO: 47            moltype = AA  length = 9
FEATURE                  Location/Qualifiers
REGION                   1..9
                         note = A1294 CDRL3
source                   1..9
                         mol_type = protein
                         organism = synthetic construct
SEQUENCE: 47
QQSNEDPLT                                                            9

SEQ ID NO: 48            moltype = AA  length = 182
FEATURE                  Location/Qualifiers
```

```
source          1..182
                mol_type = protein
                organism = synthetic construct
SEQUENCE: 48
MFHVSFRYIF GLPPLILVLL PVASSDCDIE GKDGKQYESV LMVSIDQLLD SMKEIGSNCL   60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEHHHH  180
HH                                                                 182
```

The invention claimed is:

1. A method for the treatment of an autoimmune and/or inflammatory condition in a subject in need thereof, the method comprising administering to the subject a therapeutically effective amount of an interleukin 7 (IL-7) binding protein or IL-7 binding fragment thereof comprising:
   (i) a heavy chain variable region CDR1 comprising the amino acid sequence of SEQ ID NO: 6;
   (ii) a heavy chain variable region CDR2 comprising the amino acid sequence of SEQ ID NO: 7;
   (iii) a heavy chain variable region CDR3 comprising the amino acid sequence of SEQ ID NO: 8;
   (iv) a light chain variable region CDR1 comprising the amino acid sequence of SEQ ID NO: 9;
   (v) a light chain variable region CDR2 comprising the amino acid sequence of SEQ ID NO: 10; and
   (vi) a light chain variable region CDR3 comprising the amino acid sequence of SEQ ID NO: 11.

2. The method of claim 1, wherein the IL-7 binding protein or IL-7 binding fragment thereof comprises a heavy chain variable region having a sequence at least 90% identical to the amino acid sequence of SEQ ID NO: 4 and a light chain variable region having a sequence at least 90% identical to the amino acid sequence of SEQ ID NO: 5.

3. The method of claim 2, wherein the IL-7 binding protein or IL-7 binding fragment thereof comprises a heavy chain variable region comprising the amino acid sequence of SEQ ID NO: 4 and a light chain variable region comprising the amino acid sequence of SEQ ID NO: 5.

4. The method of claim 1, wherein the IL-7 binding protein or IL-7 binding fragment thereof comprises a heavy chain having a sequence at least 80% identical to the amino acid sequence of SEQ ID NO: 2 and a light chain having a sequence at least 80% identical to the amino acid sequence of SEQ ID NO: 3.

5. The method of claim 4, wherein the IL-7 binding protein or IL-7 binding fragment thereof comprises a heavy chain comprising the amino acid sequence of SEQ ID NO: 2 and a light chain comprising the amino acid sequence of SEQ ID NO: 3.

6. The method of claim 1, wherein the IL-7 binding protein or IL-7 binding fragment thereof is an antibody.

7. The method of claim 6, wherein the antibody comprises an IgG1 or IgG4 Fc region.

8. The method of claim 7, wherein the antibody comprises a human IgG1 heavy chain constant region.

9. The method of claim 8, wherein the antibody comprises a human IgG1 heavy chain constant region having an alanine residue at position 235 and position 237 according to EU numbering.

10. The method of claim 1, wherein the autoimmune and/or inflammatory condition is multiple sclerosis, Sjögren's syndrome, rheumatoid arthritis, inflammatory bowel disease, Crohn's disease, ulcerative colitis, systemic lupus erythematosus, or type I diabetes.

11. The method of claim 10, wherein the multiple sclerosis is clinically isolated syndrome, relapsed remitting, primary progressive or secondary progressive.

12. The method of claim 10, wherein the autoimmune and/or inflammatory condition is systemic lupus erythematosus.

13. The method of claim 10, wherein the autoimmune and/or inflammatory condition is inflammatory bowel disease.

14. The method of claim 10, wherein the autoimmune and/or inflammatory condition is type 1 diabetes.

15. The method of claim 3, wherein the autoimmune and/or inflammatory condition is multiple sclerosis, Sjögren's syndrome, rheumatoid arthritis, inflammatory bowel disease, Crohn's disease, ulcerative colitis, systemic lupus erythematosus, or type I diabetes.

16. The method of claim 15, wherein the multiple sclerosis is clinically isolated syndrome, relapsed remitting, primary progressive or secondary progressive.

17. The method of claim 15, wherein the autoimmune and/or inflammatory condition is systemic lupus erythematosus, inflammatory bowel disease, or type I diabetes.

18. The method of claim 5, wherein the autoimmune and/or inflammatory condition is multiple sclerosis, Sjögren's syndrome, rheumatoid arthritis, inflammatory bowel disease, Crohn's disease, ulcerative colitis, systemic lupus erythematosus, or type I diabetes.

19. The method of claim 18, wherein the multiple sclerosis is clinically isolated syndrome, relapsed remitting, primary progressive or secondary progressive.

20. The method of claim 18, wherein the autoimmune and/or inflammatory condition is systemic lupus erythematosus, inflammatory bowel disease, or type I diabetes.

* * * * *